US012735473B2

(12) United States Patent
Yednock et al.

(10) Patent No.: US 12,735,473 B2
(45) Date of Patent: Sep. 15, 2026

(54) METHOD OF TREATING A BLOOD DISORDER ASSOCIATED WITH C1q-MEDIATED ACTIVATION OF THE CLASSICAL COMPLEMENT PATHWAY BY ADMINISTERING AN ANTI-C1q ANTIBODY

(71) Applicant: Annexon, Inc., Brisbane, CA (US)

(72) Inventors: Ted Yednock, Forest Knolls, CA (US); Sethu Sankaranarayanan, Fremont, CA (US)

(73) Assignee: Annexon, Inc., Brisbane, CA (US)

( * ) Notice: Subject to any disclaimer, the term of this patent is extended or adjusted under 35 U.S.C. 154(b) by 582 days.

(21) Appl. No.: 18/032,084

(22) PCT Filed: Oct. 15, 2021

(86) PCT No.: PCT/US2021/055216

§ 371 (c)(1),
(2) Date: Apr. 14, 2023

(87) PCT Pub. No.: WO2022/081997

PCT Pub. Date: Apr. 21, 2022

(65) Prior Publication Data

US 2023/0391858 A1 Dec. 7, 2023

Related U.S. Application Data

(60) Provisional application No. 63/093,029, filed on Oct. 16, 2020.

(51) Int. Cl.
*C07K 16/18* (2006.01)
*A61K 39/00* (2006.01)
*A61P 7/06* (2006.01)

(52) U.S. Cl.
CPC ................ *C07K 16/18* (2013.01); *A61P 7/06* (2018.01); *A61K 2039/54* (2013.01); *A61K 2039/545* (2013.01)

(58) Field of Classification Search
CPC ....... C07K 16/18; C07K 2317/76; A61P 7/06; A61P 7/04; A61P 7/00; A61K 2039/54; A61K 2039/545; A61K 2039/505
See application file for complete search history.

(56) References Cited

U.S. PATENT DOCUMENTS

| | | | |
|---|---|---|---|
| 10,227,398 B2 * | 3/2019 | Rosenthal ................ | A61P 3/10 |
| 2016/0145336 A1 | 5/2016 | Francis et al. | |
| 2016/0159890 A1 | 6/2016 | Rosenthal et al. | |
| 2016/0326231 A1 | 11/2016 | Hu et al. | |
| 2016/0355574 A1 | 12/2016 | Rosenthal et al. | |
| 2017/0152309 A1 | 6/2017 | Yednock et al. | |
| 2024/0109957 A1 | 4/2024 | Yednock et al. | |

FOREIGN PATENT DOCUMENTS

| | | |
|---|---|---|
| CN | 103596576 A | 2/2014 |
| WO | WO-2009/077483 A1 | 6/2009 |
| WO | WO-2013/082563 A1 | 6/2013 |
| WO | WO-2013/192240 A2 | 12/2013 |
| WO | WO-2015/006504 A1 | 1/2015 |
| WO | WO-2016/073685 A1 | 5/2016 |
| WO | WO-2017/091719 A1 | 6/2017 |
| WO | WO-2021/076991 A1 | 4/2021 |
| WO | WO-2022/081997 A1 | 4/2022 |

OTHER PUBLICATIONS

CognitiveVitality.org (Alzheimer's Drug Discovery Foundation). "Anti-C1q" (Apr. 1, 2019). pp. 1-16.*

Synapse by patsnap. "What are C1q inhibitors and how do theywork?" (Jun. 21, 2024). 3 pages.*

Phuan P-W, et al. (Jun. 2013) Acta Neuropathol. 125(6):829-840. (doi:10.1007/s00401-013-1128-3).*

Gertz MA, et al. (Dec. 2, 2016) Blood. 128(22):1265. (http://doi.org/10.1182/blood.V128.22.1265.1265).*

Wat et al., "Molecular actions of heparin and their implications in preventing pre-eclampsia." Journal of Thrombosis and Haemostasis 16 (2018): 1510-1522.

Dunkelberger et al., "Complement and its role in innate and adaptive immune responses." Cell Research 20 (2010): 34-50.

Hom et al., "Complement Inhibitors for Treatment of Geographic Atrophy and Advanced Non-exudative AMD." Retinal Physician 16 (2019): 28-31.

Pickering et al., "Canonical and noncanonical functions of complement in systemic lupus erythematosus." European Journal of Immunology 54 (2024): 2350918.

Schulz et al., "C1q as a target molecule to treat human disease: What do mouse studies teach us?. " Frontiers in Immunology 13 (2022): 958273.

Walport, "Complement and systemic lupus erythematosus." Arthritis Research & Therapy 4.Suppl 3 (2002): S279.

(Continued)

*Primary Examiner* — Robert S Landsman
(74) *Attorney, Agent, or Firm* — Foley Hoag LLP; David P. Halstead; Erin M. Foley

(57) ABSTRACT

The present disclosure relates generally to methods of preventing, reducing risk of developing, or treating a blood disorder (e.g., cold agglutinin hemolytic anemia (cold agglutinin disease), cold antibody hemolytic anemia, ABO incompatible acute hemolytic reactions, warm agglutinin hemolytic anemia, warm antibody hemolytic anemia, warm antibody autoimmune hemolytic anemia (WAIHA)), autoimmune hemolytic anemia (AIHA), autoimmune thrombocytopenia, paroxysmal cold hemoglobinuria (PCH), antiphospholipid syndrome (APS), Evans syndrome, red blood cell alloimmunization, Felty's syndrome, neonatal alloimmune thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, systemic lupus erythematosus (SLE), glomerulonephritis, anti-phospholipid antibody syndrome (APS), an infection, or a drug-induced hematologic disorder), comprising administering to a subject an inhibitor of the complement pathway.

21 Claims, 13 Drawing Sheets

Specification includes a Sequence Listing.

(56) References Cited

OTHER PUBLICATIONS

Broome et al. "Safety and efficacy of classical complement pathway inhibition with sutimlimab in chronic immune thrombocytopenia." Blood Advances 7.6 (2023): 987996.

De Boer et al., "C1-inhibitor treatment in patients with severe complement mediated autoimmune hemolytic anemia," Blood Advances 7.13 (2023): 3128-3139.

Extended European Search Report for EP Application No. 20877082.6 dated Apr. 28, 2023.

International Search Report and Written Opinion for International Application No. PCT/US20/56121 mailed Feb. 2, 2021.

Janeway et al., "The Complement System and Innate Immunity," Immunobiology: The Immune System in Health and Disease (2001): 15 pages.

Janeway et al., "The Interaction of the Antibody Molecule with Specific Antigen," Immunobiology: The Immune System in Health and Disease (2001): 5 pages.

Mehta et al., "Hemophilia," StatPearls, Jun. 5, 2023.

Nayak et al., "Complement and noncomplement activating functions of Clq: a prototypical innate immune molecule." Innate Immunity 18.2 (2012): 350-363.

Extended European Search Report for EP Application No. 21881186.7 dated Feb. 24, 2025.

International Search Report and Written Opinion for International Application No. PCT/US2021/055216 mailed Jan. 12, 2022.

* cited by examiner

METHOD OF TREATING A BLOOD DISORDER ASSOCIATED WITH C1q-MEDIATED ACTIVATION OF THE CLASSICAL COMPLEMENT PATHWAY BY ADMINISTERING AN ANTI-C1q ANTIBODY

RELATED APPLICATIONS

This patent application is the U.S. National Stage of International Patent Application No. PCT/US21/55216, filed Oct. 15, 2021, which claims priority to U.S. Provisional Patent Application No. 63/093,029, filed Oct. 16, 2020. The entire contents of these applications are hereby incorporated by this reference in their entireties.

REFERENCE TO A SEQUENCE LISTING

The instant application contains a Sequence Listing which has been submitted electronically in ASCII format and is hereby incorporated by reference in its entirety. Said ASCII copy, created on May 24, 2022, is named ANH-02525_SL.txt and is 36,348 bytes in size.

BACKGROUND

Blood disorders affect millions of people worldwide each year, cutting across the boundaries of age, race, sex, and socioeconomic status. Men, women, and children of all backgrounds live with the complications associated with these conditions, many of which are potentially life-threatening. Blood disorders, commonly referred to as hematologic disorders, are challenging to treat and are also a growing health concern, both in terms of mortality and the cost of care for the afflicted. Complications from deep vein thrombosis (DVT) are estimated to kill more people each year than breast cancer, motor vehicle accidents, and HIV combined.

Blood disorders may affect any of the three main components of blood: red blood cells, white blood cells, or platelets. Blood disorders can also affect the liquid portion of blood, known as plasma. Some blood disorders cause the number of cells in the blood to decrease. For example, individuals affected with leukopenia have a decrease in the number of white blood cells and are more susceptible to infections. New therapies are needed to treat blood disorders.

Currently, there is no cure for blood disorders. The molecular mechanisms of blood cell homeostasis and the pathology of blood disorders are unclear. Thus, there is a need for new therapies to prevent, reduce the risk of developing, and treat blood disorders.

SUMMARY

The present disclosure is generally directed to methods of preventing, reducing risk of developing, or treating a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, *mycoplasma*, mononucleosis, Hepatitis C, human immunodeficiency virus (HIV), coronavirus, e.g., SARS-CoV-2 (COVID)), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin), comprising administering to a subject an inhibitor of the complement pathway.

Blood disorders may be referred to as hematologic disorders. Although there are varied etiologies among hematologic disorders, several might be caused by mutations and/or autoantibodies that inactivate complement regulatory proteins, as well as mutations that directly activate the complement cascade. For example, complement mutations typically trigger uninhibited complement activation to occur on platelets, neutrophils, monocytes, and aggregates thereof, as well as on red blood cells and endothelial cells. Complement activation on these cells leads to the shedding of cell derived-microvesicles that may express complement and tissue factor, thus promoting inflammation. Complement deposition on red blood cells triggers hemolysis and the release of red blood cell-derived microvesicles that are prothrombotic. Complement deposition may also occur on cells within the vasculature, such as endothelial cells, or within highly vascularized tissues, such capillary beds, glomeruli, alveoli, etc., which can result in vascular damage in many organs. Complement activation may be prevented by inhibitors that block activation of the complement cascade. Such inhibitors can block the expression of specific complement proteins in blood cells, or in related cells and vascularized tissues, interfere with signaling molecules that induce complement activation, upregulate expression of complement inhibitors in blood cells, or in related cells and vascularized tissues, or otherwise interfere with the role of complement in a blood disorder or hematologic disorder.

Accordingly, inhibition of complement activation pathways may be a promising therapeutic strategy for preventing, reducing risk of developing, or treating a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus, e.g., SARS-CoV-2 (COVID)), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin), using antibodies to inhibit the early stages of complement activation, including the complement activation pathway. Specifically, anti-C1q, anti-C1r, and anti-C1s antibodies may prevent autoantibodies from triggering complement activation.

The present disclosure is generally directed to methods of preventing, reducing risk of developing, or treating a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus, e.g., SARS-CoV-2 (COVID)), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin), by inhibiting classical complement activation, e.g., by inhibiting complement factor C1q, C1r, or C1s, e.g., through the administration of antibodies, such as monoclonal, chimeric, humanized antibodies, human antibody, antibody fragments, antibody derivative, etc., which bind to one or more of these complement factors. In some embodiments, the antibody is humanized antibody. In some embodiments, the antibody is antibody fragment, such as a Fab fragment In some embodiments, the activity of complement factors such as C1q, C1r, or C1s is inhibited to block activation of the classical complement pathway, and slow or prevent a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus, e.g., SARS-CoV-2 (COVID)), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin). Inhibition of the classical complement pathway leaves the lectin and alternative complement pathways intact to perform their normal immune function. Methods related to neutralizing complement factors such as C1q, C1r, or C1s in a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus, e.g., SARS-CoV-2 (COVID)), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin) are disclosed herein.

In certain aspects, disclosed herein is a method of preventing, reducing risk of developing, or treating a blood disorder (e.g., cold agglutinin hemolytic anemia (cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus, e.g., SARS-CoV-2 (COVID)), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin), comprising administering to a subject an inhibitor of the complement pathway.

Disclosed herein is a method of inhibiting complement activation in a blood disorder, comprising administering to a patient suffering from adverse complement activation an antibody, such as an anti-C1q antibody, an anti-C1r antibody, or an anti-C1s antibody. The method may further comprise administration of a therapeutic agent. In certain preferred embodiments, the antibody binds to C1q, C1r, or C1s and inhibits complement activation.

In some aspects, methods of preventing, reducing risk of developing, or treating a blood disorder are disclosed. Such methods include administering to a subject a C1q inhibitor. Numerous embodiments are further provided that can be applied to any aspect of the present invention described herein. For example, in some embodiments, the C1q inhibitor is an antibody, an aptamer, an antisense nucleic acid or a gene editing agent. In some embodiments, the inhibitor is an anti-C1q antibody. The anti-C1q antibody may inhibit the interaction between C1q and an autoantibody or between C1q and C1r, or between C1q and C1s, or may promote clearance of C1q from circulation or a tissue. In some embodiments, the anti-C1q antibody has a dissociation constant ($K_D$) that ranges from 100 nM to 0.005 nM or less than 0.005 nM. In some embodiments, the anti-C1q antibody binds C1q with a binding stoichiometry that ranges from 20:1 to 1.0:1 or less than 1.0:1, a binding stoichiometry that ranges from 6:1 to 1.0:1 or less than 1.0:1, or a binding stoichiometry that ranges from 2.5:1 to 1.0:1 or less than 1.0:1. The antibody may specifically bind to and neutralize a biological activity of C1q, such as (1) C1q binding to an autoantibody, (2) C1q binding to C1r, (3) C1q binding to C1s, (4) C1q binding to IgM, (5) C1q binding to phosphatidylserine, (6) C1q binding to pentraxin-3, (7) C1q binding to C-reactive protein (CRP), (8) C1q binding to globular C1q receptor (gC1qR), (9) C1q binding to complement receptor 1 (CR1), (10) C1q binding to beta-amyloid, (11) C1q binding to calreticulin, (12) C1q binding to apoptotic cells, or (13) C1q binding to B cells, or (1) activation of the classical complement activation pathway, (2) reduction in lysis and/or reduction in C3 deposition, (3) activation of antibody and complement dependent cytotoxicity, (4) CH50 hemolysis, (5) a reduction in red blood cell lysis, (6) a reduction in red blood cell phagocytosis, (7) a reduction in dendritic cell infiltration, (8) inhibition of complement-mediated red blood cell lysis, (9) a reduction in lymphocyte infiltration, (10) a reduction in macrophage infiltration, (11) a reduction in antibody deposition, (12) a reduction in neutrophil infiltration, (13) a reduction in platelet phagocytosis, (14) a reduction in platelet lysis, (15) an improvement in transplant graft survival, (16) a reduction in macrophage mediated phagocytosis, (17) a reduction in autoantibody mediated complement activation, (18) a reduction in red blood cell destruction due to transfusion reactions, (19) a reduction in red blood cell lysis due to alloantibodies, (20) a reduction in hemolysis due to transfusion reactions, (21) a reduction in alloantibody mediated platelet lysis, (22) an improvement in anemia, (23) a reduction in eosinophilia, (24) a reduction in C3 deposition on red blood cells (e.g., a reduction of deposition of C3b, iC3b, etc., on RBCs), (25) a reduction in C3 deposition on platelets (e.g., a reduction of deposition of C3b, iC3b, etc., on platelets), (26) reduction in anaphylatoxin production, (27) a reduction in autoantibody mediated blister formation, (28) a reduction in autoantibody induced erythematosus, (29) a reduction in red blood cell destruction due to transfusion reactions, (30) a reduction in platelet lysis due to transfusion reactions, (31) a reduction in mast cell activation, (32) a reduction in mast cell histamine release, (33) a reduction in vascular permeability, (34) a reduction in complement deposition on transplant graft endothelium, (35) B-cell antibody production, (36) dendritic cell maturation, (37) T-cell proliferation, (38) cytokine production, (39) microglia activation, (40) Arthus reaction, (41) a reduction of anaphylatoxin generation in transplant graft endothelium, or (42) activation of complement receptor 3 (CR3/C3) expressing cells. In some embodiments, CH50 hemolysis comprises human CH50 hemolysis. The antibody may be capable of neutralizing from at least about 50%, to about 100% of human CH50 hemolysis. The antibody may be capable of neutralizing about 50%, about 60%, about 70%, about 80%, about 90%, about 100% of human CH50 hemolysis. The antibody may be capable of neutralizing at least 50% of CH50 hemolysis at a dose of less than 150 ng/ml, less than 100 ng/ml, less than 50 ng/ml, or less than 20 ng/ml.

In some embodiments, the antibody is a monoclonal antibody, a polyclonal antibody, a recombinant antibody, a humanized antibody, a human antibody, a chimeric antibody, a monovalent antibody, a multispecific antibody, or an antibody fragment, or antibody derivative thereof. In some embodiments, the antibody is humanized antibody. In some embodiments, the antibody is antibody fragment, such as a Fab fragment. Examples of an antibody fragment are a Fab fragment, a Fab' fragment, a F(ab')2 fragment, a Fv fragment, a diabody, and a single chain antibody molecule. In some embodiments, the antibody comprises a light chain variable domain comprising an HVR-L1 having the amino acid sequence of SEQ ID NO: 5, an HVR-L2 having the amino acid of SEQ ID NO: 6, and an HVR-L3 having the amino acid of SEQ ID NO: 7. In some embodiments, the antibody comprises a heavy chain variable domain comprising an HVR-H1 having the amino acid sequence of SEQ ID NO: 9, an HVR-H2 having the amino acid of SEQ ID NO: 10, and an HVR-H3 having the amino acid of SEQ ID NO: 11. In some embodiments, the antibody comprises a light chain variable domain comprising an amino acid sequence with at least about 95% homology to the amino acid sequence selected from SEQ ID NO: 4 and 35-38 and wherein the light chain variable domain comprises an HVR-L1 having the amino acid sequence of SEQ ID NO: 5, an HVR-L2 having the amino acid of SEQ ID NO: 6, and an HVR-L3 having the amino acid of SEQ ID NO: 7. In some embodiments, the light chain variable domain comprising an amino acid sequence selected from SEQ ID NO: 4 and 35-38. In some embodiments, the antibody comprises a heavy chain variable domain comprising an amino acid sequence with at least about 95% homology to the amino acid sequence selected from SEQ ID NO: 8 and 31-34 and wherein the heavy chain variable domain comprises an HVR-H1 having the amino acid sequence of SEQ ID NO: 9, an HVR-H2 having the amino acid of SEQ ID NO: 10, and an HVR-H3 having the amino acid of SEQ ID NO: 11. In some embodiments, the heavy chain variable domain comprising an amino acid sequence selected from SEQ ID NO: 8 and 31-34. In some embodiments, the antibody is an antibody fragment comprising a heavy chain Fab fragment of SEQ ID NO: 39 and a light chain Fab fragment of SEQ ID NO: 40. The antibody may be administered by parenteral injection or infusion, such as a subcutaneous or intramuscular injection, or an intravenous injection or infusion.

In some embodiments, the antibody is a full-length antibody. In some embodiments, the antibody is administered to the subject by intravenous injection or infusion at a dose between 10 mg/kg and 150 mg/kg. In some embodiments, the antibody is administered to the subject by intravenous injection or infusion at a dose between 10 mg/kg and 20 mg/kg, 20 mg/kg and 30 mg/kg, 30 mg/kg and 40 mg/kg, 40 mg/kg and 50 mg/kg, 50 mg/kg and 60 mg/kg, 60 mg/kg and 70 mg/kg, 70 mg/kg and 80 mg/kg, 80 mg/kg and 90 mg/kg, 90 mg/kg and 100 mg/kg, 100 mg/kg and 110 mg/kg, 110 mg/kg and 120 mg/kg, 120 mg/kg and 130 mg/kg, 130 mg/kg and 140 mg/kg, or 140 mg/kg and 150 mg/kg. In some embodiments, the antibody is administered to the subject by intravenous injection or infusion at a dose between 75 mg/kg and 100 mg/kg. In some embodiments, the antibody is administered to the subject by intravenous injection or infusion at a dose of 10 mg/kg, 20 mg/kg, 30 mg/kg, 40 mg/kg, 50 mg/kg, 60 mg/kg, 70 mg/kg, 75 mg/kg, 80 mg/kg, 90 mg/kg, 100 mg/kg, 110 mg/kg, 120 mg/kg, 130 mg/kg, 140 mg/kg, or 150 mg/kg. In some embodiments, the antibody is administered to the subject by intravenous injection or infusion at a dose of 75 mg/kg. In some embodiments, the antibody is administered to the subject by intravenous injection or infusion at a dose of 100 mg/kg. The antibody may be administered, once a week, once every other week, or once a month. In some embodiments, the antibody is administered to the subject by intravenous injection or infusion at a dose of 75 mg/kg. In some embodiments, the antibody is administered to the subject by intravenous injection or infusion at a dose of 100 mg/kg. The antibody may be administered, once a week, once every other week, once every three weeks, or once a month. In some embodiments, the antibody is administered to the subject by intravenous injection or infusion at a dose of 75 mg/kg once a week. In some embodiments, the antibody is administered to the subject by intravenous injection or infusion at a dose of 75 mg/kg once every two weeks. In some embodiments, the antibody is administered to the subject by intravenous injection or infusion at a dose of 75 mg/kg once every three weeks. In some embodiments, the antibody is administered to the subject by intravenous injection or infusion at a dose of 75 mg/kg once a month. In some embodiments, the antibody is administered to the subject by intravenous injection or infusion at a dose of 100 mg/kg once a week. In some embodiments, the antibody is administered to the subject by intravenous injection or infusion at a dose of 100 mg/kg every two weeks. In some embodiments, the antibody is administered to the subject by intravenous injection or infusion at a dose of 100 mg/kg once every three weeks. In some embodiments, the antibody is administered to the subject by intravenous injection or infusion at a dose of 100 mg/kg once a month. In some embodiments, the antibody is administered to the subject by subcutaneous or intramuscular injection at a dose between 1 mg/kg and 10 mg/kg. In some embodiments, the antibody is administered to the subject by subcutaneous or intramuscular injection at a dose between 1 mg/kg and 3 mg/kg, 3 mg/kg and 5 mg/kg, 5 mg/kg and 7 mg/kg, or 7 mg/kg and 10 mg/kg. In some embodiments, the antibody is administered daily, once every other day, once a week, once every other week, once every three weeks, or once a month.

In some embodiments, the antibody is an antibody fragment. In some embodiments, the antibody fragment is administered to the subject by intravenous injection or infusion, by intramuscular injection, or by subcutaneous injection. In some embodiments, the antibody fragment is administered at a dose between 0.1 mg/kg and 50 mg/kg. In some embodiments, the antibody fragment is administered at a dose between 0.1 mg/kg and 1 mg/kg, 1 mg/kg and 5 mg/kg, 5 mg/kg and 10 mg/kg, 10 mg/kg and 15 mg/kg, 15 mg/kg and 20 mg/kg, 20 mg/kg and 25 mg/kg, 25 mg/kg and 30 mg/kg, 30 mg/kg and 35 mg/kg, 35 mg/kg and 40 mg/kg, 40 mg/kg and 45 mg/kg, or 45 mg/kg and 50 mg/kg. In some embodiments, the antibody fragment is administered at a dose between 0.3 mg/kg and 10 mg/kg. In some embodiments, the antibody fragment is administered daily, once every other day, once a week, once every other week, or once a month. In some embodiments, the antibody fragment is administered at an initial predose that is higher than the daily, once every other day, once a week, once every other week, or once a month dose. In some embodiments, the initial predose is between 3 mg/kg and 50 mg/kg. In some embodiments, the initial predose is between 3 mg/kg and 5 mg/kg, 5 mg/kg and 10 mg/kg, 10 mg/kg and 15 mg/kg, 15 mg/kg and 20 mg/kg, 20 mg/kg and 25 mg/kg, 25 mg/kg and 30 mg/kg, 30 mg/kg and 35 mg/kg, 35 mg/kg and 40 mg/kg, 40 mg/kg and 45 mg/kg, or 45 mg/kg and 50 mg/kg. In some embodiments, the initial predose is between 3 mg/kg and 20 mg/kg. In some embodiments, the antibody fragment has a shorter half-life as compared to its corresponding full-length antibody, such as the antibody fragment is rapidly cleared, thereby sparing C1q activity outside the subject's blood space, or the antibody selectively inhibits C1q within the subject's blood space, thereby sparing C1q activity outside the subject's blood space. In some embodiments, the blood space is confined within a blood vessel, such as an artery, an arteriole, a capillary, a venule, or a vein. The blood space may comprise serum, platelets, endothelial cells, blood cells, or hematopoietic cells. In some embodiments, inhibiting C1q within the subject's blood space reduces tissue damage in a highly vascularized tissue. Examples of highly vascularized tissues are kidney, alveoli, capillary bed, or glomerulus.

In some embodiments, the blood disorder is a complement-mediated blood disorder. In some embodiments, the blood disorder is cold agglutinin hemolytic anemia (cold agglutinin disease), cold antibody hemolytic anemia, ABO incompatible acute hemolytic reactions, warm agglutinin hemolytic anemia, warm antibody hemolytic anemia, warm autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, systemic lupus erythematosus (SLE), glomerulonephritis, anti-phospholipid antibody syndrome (APS), an infection, or a drug-induced hematologic disorder. The infection may be pneumonia, mycoplasma, mononucleosis, hepatitis C, human immunodeficiency virus (MV), or coronavirus. Examples of the coronavirus are selected from SARS-CoV, MERS-CoV, HCoV, HKU1, and SARS-CoV-2. In some embodiments, the coronavirus is SARS-CoV-2. In some embodiments, the subject has SARS-CoV-2 infection, which has been confirmed by reverse-transcription polymerase chain reaction (RT-PCR) from respiratory tract or blood specimens. The blood disorder may be cold agglutinin hemolytic anemia (cold agglutinin disease), warm autoimmune hemolytic anemia (WAIHA), paroxysmal cold hemoglobinuria (PCH), lupus nephritis, heparin-induced thrombocytopenia (HIT), heparin-induced thrombocytopenia and thrombosis (HITT), or immune thrombocytopenic purpura (ITP). Examples of the drug-induced hematologic disorder are aplastic anemia, agranulocytosis, megaloblastic anemia, hemolytic anemia, and thrombocytopenia.

In some aspects, methods of preventing, reducing risk of developing, or treating a blood disorder are disclosed. Such methods include administering to a subject an inhibitor of the classical complement pathway, wherein the subject comprises blood space; and the inhibitor selectively inhibits the classical complement pathway within the subject's blood space, thereby sparing complement activity within tissues. Numerous embodiments are further provided that can be applied to any aspect of the present invention described herein.

DESCRIPTION OF THE FIGURES

FIG. 1A shows that anti-C1q antibody inhibits C1q, C4d, and C3b binding/activation on the RBC surface in the presence of sera from patients with CAD to prevent extravascular lysis. FIG. 1B shows that anti-C1q antibody blocks C5-C9-mediated lysis of red blood cells initiated by sera from CAD patients to prevent intravascular lysis.

FIG. 2A shows that both anti-C1q antibody and TNT009 inhibit antibody/complement-induced lysis of red blood cells. FIG. 2B shows that only anti-C1q antibody inhibits upstream binding of C1q to target cells. C1q binding to RBC is not affected by TNT009. C1q is one of the three major opsonins/immune cell ligands deposited on red blood cells.

FIG. 6A shows effect of Mab2. FIG. 6B shows effect of FabA.

FIG. 7A is a graph showing complement activation in different incubation conditions. Plasma from a healthy donor was incubated with EDTA (10 mM) or EGTA (10 mM)±MgCl2 (10 mM) or with buffer before incubating with PF4/heparin and complement activation was measured by the antigen~C3e capture ELISA assay. *p<0.0001. Results are shown from a representative experiment involving three donors tested on three different occasions. FIG. 7B is a graph showing the complement activation in different incubation conditions. Plasma from a healthy donor was incubated with or without C1-inhibitor (10 and 20 IU/mL) before incubating with PF4/heparin and complement activation by PF4/heparin was determined by antigen-C3c capture ELISA assay. *p<0 0001. FIG. 7C is a histogram showing the binding of anti-PF4/heparin (KKO) to B cells in various incubation conditions. The overlapping peaks represent buffer control (striped lines), followed by PF4, PF4/heparin+EDTA, PF4/heparin+EGTA+MgCl2, and PF4/heparin+EGTA. Peak 1 represents PF4/heparin. FIG. 7D is a histogram showing the binding of anti-C3e to B cells in various incubation conditions. The overlapping peaks represent PF4/heparin+EDTA, PF4/heparin+EGTA, PF4/heparin+EGTA+MgCl2, and buffer control (striped lines), and PF4. Peak 1 represents PF4/heparin. FIG. 7E is a graph showing complement activation in presence of various antibodies. Plasma from a healthy donor was incubated with various concentration of anti-C1q antibody, anti-MBL antibody or control antibody (0-100 ug/mL) before adding PF4/heparin and complement activation by PF4/heparin was determined by the antigen-C3c capture ELISA assay. *p<0.05, p<0.001, *p<0.0001, compared to with no antibody added condition. Results are shown from a representative experiment involving three donors tested on three different occasions. FIG. 7F is a histogram showing the binding of anti-PF4/heparin to B cells in various incubation conditions. The peaks represent the buffer control (striped line), anti-C1q+PF4/heparin (peak 1), anti-MBL+PF4/heparin (peak 2), PF4/heparin (peak 3), and MS IgG 1+PF4/heparin (peak 4). FIG. 7G is a histogram showing the binding of anti-C3c to B cells in various incubation conditions. The peaks represent the buffer control (striped line), anti-C1q+PF4/heparin (peak 1), anti-MBL+PF4/heparin (peak 2), PF4/heparin (peak 3), and MS IgG 1+PF4/heparin (peak 4).

FIG. 8 is a graph showing the PF4/heparin induced C' activation by different donors (determined by ELISA based antigen capture assay) and their plasma IgM levels (quantified by proteomic analysis). For each point on the x-axis, the left bar represents C3e and the right bar represents IgM.

FIG. 12A shows that Mab1 15 mpk IV results in peak serum Free Mab1 levels of 250,000 ng/mL. Free drug levels stay elevated until day 4 and clears to levels below detection on day 5. FIG. 12B shows that FabA 10 mpk IV results in peak drug levels of 12000 ng/mL and clears very rapidly with drug levels falling below limit of detection by 8 hours. Estimated half-life of the Fab molecule is 2-3 hrs. FIG. 12C shows that FabA 3 mpk SC showed a very gradual increase in free drug levels and measurable at 24 hrs after a single dose.

DETAILED DESCRIPTION

General

Figure 1A:
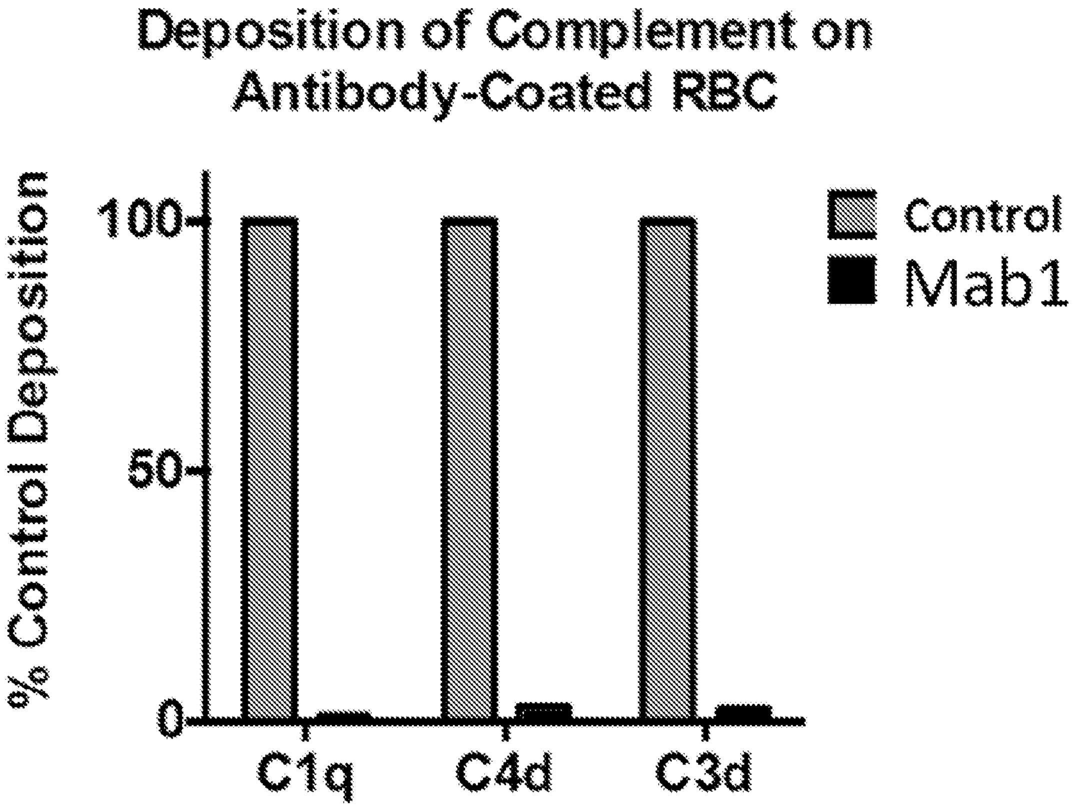
FIGS. 1A-1B show anti-C1q antibody (Mab1) effectively arrests processes associated with both intravascular and extravascular RBC lysis in CAD.

The present disclosure relates generally to methods of preventing, reducing risk of developing, or treating a blood disorder (e.g., cold agglutinin hemolytic anemia (cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus, e.g., SARS-CoV-2 (COVID)), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin), comprising administering to a subject an inhibitor of the complement pathway.

There are varied etiologies among the blood disorders of the present invention; however, the blood disorders of the present invention are generally characterized by uninhibited complement activation on blood components and cells, as well as related cells within the vasculature and within highly vascularized tissues. Complement activation on these cells leads deposition of complement components that can lead to immune cell recruitment an attack. It can also lead to the shedding of cell derived-microvesicles that may express complement and tissue factor, thus promoting inflammation. Complement deposition on red blood cells can trigger intravascular or extravascular hemolysis and/or the release of red blood cell-derived microvesicles that are prothrombotic. Complement deposition also may occur on cells within the vasculature, such as endothelial cells, or within highly vascularized tissues, such capillary beds, glomeruli, alveoli, etc., which can result in vascular damage in many organs. Complement deposition on red blood cells can also result in enhanced extravascular clearance. Complement activation may be prevented by inhibitors that block activation of the complement cascade. Such inhibitors can block the expression of specific complement proteins in blood cells, or in related cells of the vasculature and highly vascularized tissues, interfere with signaling molecules that induce complement activation, upregulate expression of complement inhibitors in blood cells, or in related cells and vascularized tissues, or otherwise interfere with the role of complement in a blood disorder or hematologic disorder.

Figure 1B:
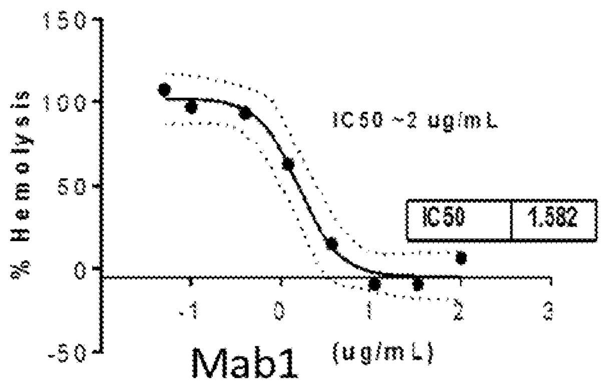
Figure 2A:
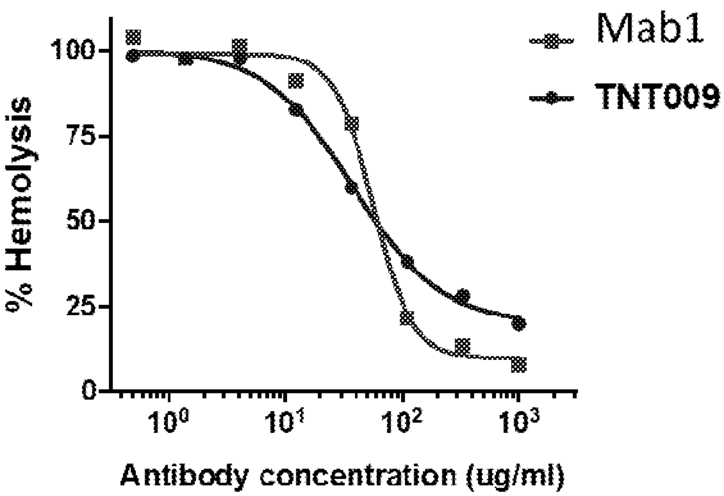
FIGS. 2A-2B show that anti-C1q antibody (e.g., Mab1) and anti-C1s (e.g., TNT009) antibodies inhibit complement-mediated hemolysis.

For example, chronic hemolytic disease patients often manifest severe anemia. In Cold Agglutinin Disease (CAD) and Warm Autoimmune Hemolytic Anemia (wAIHA), autoreactive antibodies against red blood cells (RBC's) trigger C1q binding and classical complement activation. Complement activation causes RBC clearance resulting in chronic anemia. Complement-mediated red blood cell damage follows when C1q recognizes autoantibodies bound to red blood cells, triggers the classical pathway to coat red blood cells with activated complement components—C1q, C4b, C3b—and complement-coated RBCs are removed from circulation, resulting in anemia. In CAD and wAIHA, RBCs become coated with the three major classical complement "opsonins", C1q, C4b and C3b, that drive RBC clearance via "extravascular lysis". C1q, C4b and C3b are recognized in the spleen and liver by the reticuloendothelial system for RBC removal. Also in CAD and wAIHA, RBCs become coated with C5b to initiate membrane-attack complex (MAC)-mediated lysis of red blood cells, causing direct intravascular RBC lysis. Anti-C1q effectively arrests both intravascular and extravascular processes associated with RBC lysis in CAD (FIG. 1A-FIG. 1B). Anti-C1q antibodies can inhibit deposition of the major "opsonins"/immune cell ligands (C1q, C4b & C3b) of the complement cascade. Anti-C1q (e.g., Mab1 antibody comprising heavy chain variable domain of SEQ ID NO: 3 and light chain variable domain of SEQ ID NO: 7) and anti-C1s (e.g., TNT009) antibodies both inhibit direct complement-mediated hemolysis—consistent with inhibition of intravascular lysis (FIG. 2A), while only anti-C1q antibody inhibits upstream binding of C1q to target cells (FIG. 2B), which is an opsonin involved in extravascular lysis. Anti-C1s antibody does not block C1q binding, while anti-C3 would not block C1q or C4b binding to RBC and anti-C5 would not inhibit C1q, C4b or C3b binding to RBC's. Only anti-C1q inhibits the coating of RBC's with all three opsonins involved in extravascular hemolysis.

Inhibiting the complement pathway (e.g., by anti-C1q antibodies) stops complement deposition on cells within the vasculature or within highly vascularized tissue. In a blood disorder, C1q binds to damaged tissue or to components exposed by damaged tissue, causing complement activation with C1q, C4b and C3b deposition on the cell surface and further damage. By blocking C1q binding to cells within the blood space or within highly vascularized tissues, it stops further complement-mediated damage to the tissues or organs. For example, lupus nephritis may be treated by blocking C1q activation on the surface of cells within the highly vascularized components of the kidney—where blood filtration occurs.

Figure 3:
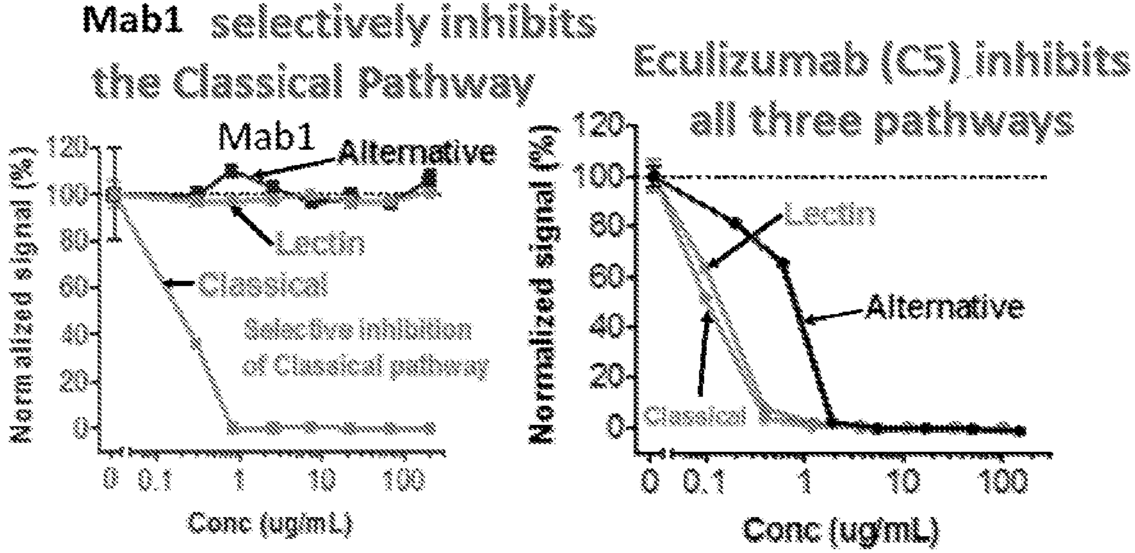
FIG. 3 shows anti-C1q antibody (e.g., Mab1) selectively inhibits the classical complement cascade, and unlike anti-C5, leaves the lectin and alternative pathways intact to perform normal immune function.
Figure 4:
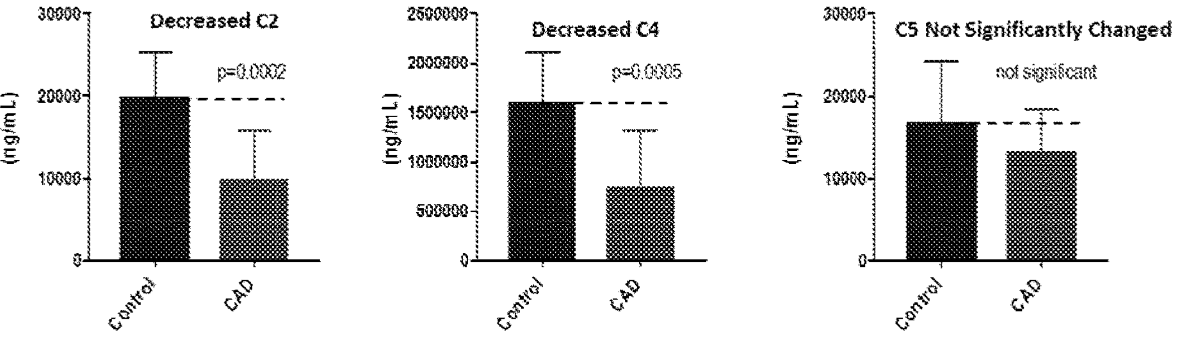
FIG. 4 shows serum biomarkers of complement depletion/consumption in CAD patients. Decrease in C4 and C2, but not C5, shows over-activation of early complement cascade with consumption of early complement components.
Figure 5:
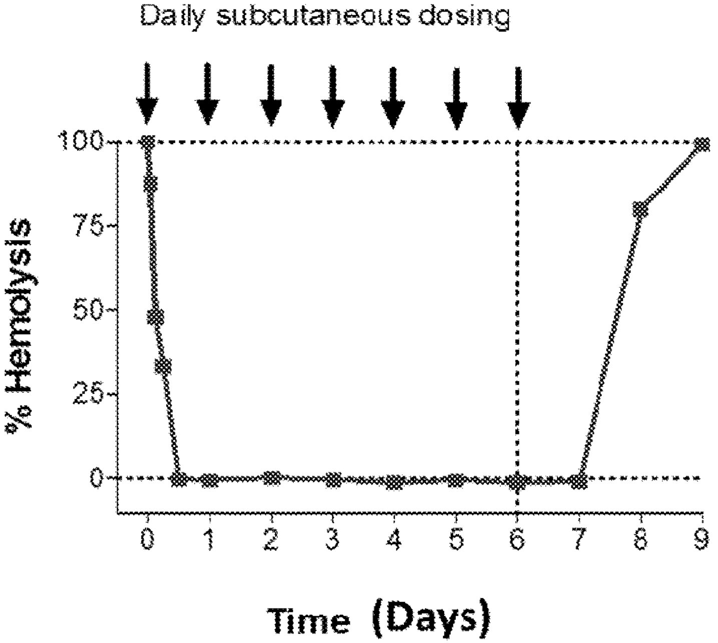
FIG. 5 shows inhibition of RBC lysis with subcutaneous administration of anti-C1q antibody fragment (e.g., FabA) in primates.

Anti-C1q antibody (e.g., Mab1 antibody comprising heavy chain variable domain of SEQ ID NO: 3 and light chain variable domain of SEQ ID NO: 7) selectively inhibits the Classical Pathway to preserve normal immune function of Lectin and Alternative pathways (FIG. 3). In contrast anti-C5 inhibits the hemolytic activity of all three pathways (FIG. 3) as would anti-C3. Unlike anti-C3 and anti-C5 antibodies, anti-C1q antibodies leave lectin and alternative pathways to perform normal immune function. Serum biomarkers of complement depletion/consumption in CAD patients provide additional assessments. Decrease in C4 and C2, but not C5, is consistent with chronic over-activation of the early complement cascade, with consumption of early complement components (FIG. 4). CAD can be treated by subcutaneous administration of anti-C1q antibody (e.g., FabA, an anti-C1q Fab comprising heavy chain Fab fragment of SEQ ID NO: 39 and light chain Fab fragment of SEQ ID NO: 40) to inhibit RBC lysis in primates (FIG. 5).

A distinction between administration of the Fab vs. whole antibody against C1q is the degree of systemic C1q inhibition. Given the full-length antibody's long half-life, the antibody stays in the blood space for a long time (e.g., a few days) after administration of the full-length antibody. This allows the antibody to penetrate into tissues blocking C1q activity throughout the body. For example, 10 mg/kg of full-length antibody would last for a few days in the blood space and would have time to penetrate into tissues blocking C1q throughout the body. In some circumstances, there may be preference to limit C1q inhibition to the vascular compartment for the treatment of vascular disease—essentially "local treatment" for the disease while allowing C1q function elsewhere. For this purpose, Fab fragments with high affinity and shorter half-lives are administered subcutaneously or intravenously. For example, when 10 mg/kg (or 0.3 mg/Kg-20 mg/Kg) of Fab is given IV, free drug is cleared rapidly (≤8 hrs)—however, drug bound to C1q in the circulation persists, so C1q remains inhibited for about 24 hours until it is replaced.

In one such application, CAD is a chronic, but generally non-life threatening disease, that largely occurs in elderly individuals. In such a case, there may be safety advantages for selectively inhibiting C1q in the vascular space to protect RBC, while allow C1q to perform its normal immune functions elsewhere in the body. This objective could be achieved by subcutaneous self-administration of anti-C1q monovalent Fab (e.g., anti-C1q antibody Fab fragment ("FabA") comprising heavy chain Fab fragment of SEQ ID NO: 39 and light chain Fab fragment of SEQ ID NO: 40). With extremely high affinity of the monovalent Fab (10 pM), drug remains tightly bound to C1q as C1q travels in the circulation. Free drug (not bound to C1q) is rapidly cleared from the circulation and does not enter tissues. Circulating C1q function returns with C1q turnover in blood (24-48 hours) (FIG. 5). The anti-C1q monovalent Fab can be dosed subcutaneously, e.g., daily. The anti-C1q monovalent Fab can be dosed 0.3-10 mg/kg subcutaneously every 24 hours (or, depending upon how quickly the Fab construct is absorbed from the skin, once every other day, once a week, once every other week, or once a month) to fully inhibit complement activation on the RBC surface within the circulation, thereby preventing both intravascular and extravascular RBC lysis (in CAD, "extravascular" lysis occurs in the liver by Kupfer cell capture of circulating RBC that are coated with complement). However, after administration, the anti-C1q monovalent Fab (e.g., anti-C1q antibody Fab fragment comprising heavy chain Fab fragment of SEQ ID NO: 39 and light chain Fab fragment of SEQ ID NO: 40) selectively inhibits C1q in the blood space—thereby preventing complement deposition on circulating RBC's, while allowing tissue C1q to retain normal immune function.

A Fab fragment of a high affinity antibody against C1q, with a short circulating half-life, can fully suppress activity of C1q in the blood space for 24 hours with daily subcutaneous administration. Its short circulating half-life would limit the extent of systemic inhibition (i.e., inhibition of C1q in tissues), thereby preserving C1q function outside of the blood space.

Neutralizing the activity of complement factors such as C1q, C1r, or C1s inhibits classical complement activity, and slows or prevents complement-mediated disorders of the vascular compartment (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus, e.g. SARS-CoV-2 (COVID)), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin). Inhibition of the classical complement pathway leaves the lectin and alternative complement pathways intact to perform their normal immune function. Methods related to neutralizing complement factors such as C1q, C1r, or C1s in a blood disorder (e.g., cold agglutinin hemolytic anemia (cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin) are disclosed herein.

All sequences mentioned in the present disclosure are incorporated by reference from U.S. patent application Ser. No. 14/933,517, U.S. patent application Ser. No. 14/890,811, U.S. Pat. Nos. 8,877,197, 9,708,394, U.S. patent application Ser. No. 15/360,549, U.S. Pat. Nos. 9,562,106, 10,450,382, 10,457,745, International Patent Application No. PCT/US2018/022462 each of which is hereby incorporated by reference for the antibodies and related compositions that it discloses.

In certain aspects, disclosed herein is a method of preventing, reducing risk of developing, or treating a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin), comprising administering to a subject an inhibitor of the complement pathway.

Full-length antibodies may be prepared by the use of recombinant DNA engineering techniques. Such engineered versions include those created, for example, from natural antibody variable regions by insertions, deletions or changes in or to the amino acid sequences of the natural antibodies. Particular examples of this type include those engineered variable region domains containing at least one CDR and optionally one or more framework amino acids from one antibody and the remainder of the variable region domain from a second antibody. The DNA encoding the antibody may be prepared by deleting all but the desired portion of the DNA that encodes the full length antibody. DNA encoding chimerized antibodies may be prepared by recombining DNA substantially or exclusively encoding human constant regions and DNA encoding variable regions derived substantially or exclusively from the sequence of the variable region of a mammal other than a human. DNA encoding humanized antibodies may be prepared by recombining DNA encoding constant regions and variable regions other than the complementarity determining regions (CDRs) derived substantially or exclusively from the corresponding human antibody regions and DNA encoding CDRs derived substantially or exclusively from a mammal other than a human.

Suitable sources of DNA molecules that encode antibodies include cells, such as hybridomas, that express the full-length antibody. For example, the antibody may be isolated from a host cell that expresses an expression vector that encodes the heavy and/or light chain of the antibody.

Antibody fragments and/or antibody derivatives may also be prepared by the use of recombinant DNA engineering techniques involving the manipulation and re-expression of DNA encoding antibody variable and constant regions. Standard molecular biology techniques may be used to modify, add or delete further amino acids or domains as desired. Any alterations to the variable or constant regions are still encompassed by the terms 'variable' and 'constant' regions as used herein. In some instances, PCR is used to generate an antibody fragment by introducing a stop codon immediately following the codon encoding the interchain cysteine of $C_H1$, such that translation of the $C_H1$ domain stops at the interchain cysteine. Methods for designing suitable PCR primers are well known in the art and the sequences of antibody $C_H1$ domains are readily available. In some embodiments, stop codons may be introduced using site-directed mutagenesis techniques.

An antibody of the present disclosure may be derived from any antibody isotype ("class") including for example IgG, IgM, IgA, IgD and IgE and subclasses thereof, including for example IgG1, IgG2, IgG3 and IgG4. In certain preferred embodiments, the heavy and light chains of the antibody are from IgG. The heavy and/or light chains of the antibody may be from murine IgG or human IgG. In certain other preferred embodiments, the heavy and/or light chains of the antibody are from human IgG1. In still other preferred embodiments, the heavy and/or light chains of the antibody are from human IgG4.

In some embodiments, the inhibitor is an antibody, such as an anti-C1q antibody, an anti-C1r antibody, or an anti-C1s antibody. The anti-C1q antibody may inhibit the interaction between C1q and an autoantibody, or between C1q and C1r, or between C1q and C1s. The anti-C1r antibody may inhibit the interaction between C1r and C1q, or between C1r and C1s. The anti-C1r antibody may inhibit the catalytic activity of C1r, or the anti-C1r antibody may inhibit the processing of pro-C1r to an active protease. The anti-C1s antibody may inhibit the interaction between C1s and C1q, or between C1s and C1r, or between C1s and C2 or C4, or the anti-C1s antibody may inhibit the catalytic activity of C1s, or it may inhibit the processing of pro-C1s to an active protease. In some instances, the anti-C1q, anti-C1r, or anti-C1s antibody causes clearance of C1q, C1r or C1s from the circulation or a tissue.

The antibody disclosed herein may be a monoclonal antibody, e.g., that binds mammalian C1q, C1r, or C1s, preferably human C1q, C1r, or C1s. The antibody may be a mouse antibody, a human antibody, a humanized antibody, a chimeric antibody, an antibody fragment, or an antibody derivative thereof. In some embodiments, the antibody is humanized antibody. In some embodiments, the antibody is antibody fragment, such as a Fab fragment. The antibody can be a chimeric antibody with sufficient human sequence that is suitable for administration to a human. The antibody can be glycosylated or nonglycosylated; in some embodiments, the antibody is glycosylated, e.g., in a glycosylation pattern produced by post-translational modification in a CHO cell. In some embodiments, the antibodies are produced in *E. coli.*

The antibodies of the present disclosure may also be covalently linked to a therapeutic agent, such as an anti-inflammatory protein, neurotherapeutic agent, anti-viral, anti-parasitic, anti-bacterial, endocrine drug, metabolic drug, mitotoxin, chemotherapy drug, or siRNA.

In some embodiments, an anti-C1q, anti-C1r, or anti-C1s antibody of the present disclosure reduces C3 deposition onto red blood cells; for example, in some embodiments, an anti-C1q, anti-C1r, or anti-C1s antibody of the present disclosure reduces deposition of C3b, iC3b, etc., onto RBCs. In some embodiments, an anti-C1q, anti-C1r, or anti-C1s antibody of the present disclosure inhibits complement-mediated red blood cell lysis. The antibodies disclosed herein may reduce C3 deposition onto platelets; for example, in some embodiments, an anti-C1q, anti-C1r, or anti-C1s antibody of the present disclosure reduces deposition of C3b, iC3b, etc., onto platelets.

An antibody of the present disclosure may bind to and inhibit a biological activity of C1q, C1r, or C1s. For example, (1) C1q binding to an autoantibody, (2) C1q binding to C1r, (3) C1q binding to C1s, (4) C1q binding to phosphatidylserine, (5) C1q binding to pentraxin-3, (6) C1q binding to C-reactive protein (CRP), (7) C1q binding to globular C1q receptor (gC1qR), (8) C1q binding to complement receptor 1 (CR1), (9) C1q binding to B-amyloid, or (10) C1q binding to calreticulin. In other embodiments, the biological activity of C1q is (1) activation of the classical complement activation pathway, (2) reduction in lysis and/or reduction in C3 deposition, (3) activation of antibody and complement dependent cytotoxicity, (4) CH50 hemolysis, (5) a reduction in red blood cell lysis, (6) a reduction in red blood cell phagocytosis, (7) a reduction in dendritic cell infiltration, (8) inhibition of complement-mediated red blood cell lysis, (9) a reduction in lymphocyte infiltration, (10) a reduction in macrophage infiltration, (11) a reduction in antibody deposition, (12) a reduction in neutrophil infiltration, (13) a reduction in platelet phagocytosis, (14) a reduction in platelet lysis, (15) an improvement in transplant graft survival, (16) a reduction in macrophage mediated phagocytosis, (17) a reduction in autoantibody mediated complement activation, (18) a reduction in red blood cell destruction due to transfusion reactions, (19) a reduction in red blood cell lysis due to alloantibodies, (20) a reduction in hemolysis due to transfusion reactions, (21) a reduction in alloantibody mediated platelet lysis, (22) an improvement in anemia, (23) a reduction in eosinophilia, (24) a reduction in C3 deposition on red blood cells (e.g., a reduction of deposition of C3b, iC3b, etc., on RBCs), (25) a reduction in C3 deposition on platelets (e.g., a reduction of deposition of C3b, iC3b, etc., on platelets), (26) reduction in anaphylatoxin production, (27) a reduction in autoantibody mediated blister formation, (28) a reduction in autoantibody induced erythematosus, (29) a reduction in red blood cell destruction due to transfusion reactions, (30) a reduction in platelet lysis due to transfusion reactions, (31) a reduction in mast cell activation, (32) a reduction in mast cell histamine release, (33) a reduction in vascular permeability, (34) a reduction in complement deposition on transplant graft endothelium, (35) B-cell antibody production, (36) dendritic cell maturation, (37) T-cell proliferation, (38) cytokine production, (39) microglia activation, (40) Arthus reaction, (41) a reduction of anaphylatoxin generation in transplant graft endothelium, or (42) activation of complement receptor 3 (CR3/C3) expressing cells.

In some embodiments, CH50 hemolysis comprises human, mouse, and/or rat CH50 hemolysis. In some embodiments, the antibody is capable of neutralizing from at least about 50%, to at least about 95% of CH50 hemolysis. In some embodiments, the antibody is capable of neutralizing 50%, 60%, 70%, 80, 90%, or 100% of CH50 hemolysis. The antibody may also be capable of neutralizing at least 50% of CH50 hemolysis at a dose of less than 150 ng/ml, less than 100 ng/ml, less than 50 ng/ml, or less than 20 ng/ml.

Other in vitro assays to measure complement activity include ELISA assays for the measurement of split products of complement components or complexes that form during complement activation. Complement activation via the classical pathway can be measured by following the levels of C4d and C4 in the serum. Activation of the alternative pathway can be measured in an ELISA by assessing the levels of Bb or C3bBbP complexes in circulation. An in vitro antibody-mediated complement activation assay may also be used to evaluate inhibition of C3a production.

An antibody of the present disclosure may be a monoclonal antibody, a polyclonal antibody, a recombinant antibody, a humanized antibody, a human antibody, a chimeric antibody, a multispecific antibody, an antibody fragment thereof, or a derivative thereof. In some embodiments, the antibody is humanized antibody. In some embodiments, the antibody is antibody fragment, such as a Fab fragment.

The antibodies of the present disclosure may also be an antibody fragment, such as a Fab fragment, a Fab' fragment, a F(ab')2 fragment, a Fv fragment, a diabody, or a single chain antibody molecule.

Disclosed herein are methods of administering to the subject a second agent, such as a second antibody or a second inhibitor. The antibody may be an anti-C1q antibody, an anti-C1r antibody, or an anti-C1s antibody. The inhibitor may be an inhibitor of antibody-dependent cellular cytotoxicity, alternative complement activation pathway; and/or an inhibitor of the interaction between the autoantibody and an autoantigen.

In some embodiments, a method is provided of determining a subject's risk of developing a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin), comprising: (a) administering an antibody to the subject (i.e. an anti-C1q, anti-C1r, or anti-C1s antibody), wherein the antibody is coupled to a detectable label; (b) detecting the detectable label to measure the amount or location of C1q, C1r, or C1s in the subject; and (c) comparing the amount or location of one or more of C1q, C1r, or C1s to a reference, wherein the risk of developing a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin) is characterized based on a the comparison of the amount or location of one or more of C1q, C1r, or C1s to the reference. The detectable label may comprise a nucleic acid, oligonucleotide, enzyme, radioactive isotope, biotin or a fluorescent label. In some instances, the antibody may be labeled with a coenzyme such as biotin using the process of biotinylation. When biotin is used as a label, the detection of the antibody is accomplished by addition of a protein such as avidin or its bacterial counterpart streptavidin, either of which can be bound to a detectable marker such as the aforementioned dye, a fluorescent marker such as fluorescein, a radioactive isotope or an enzyme such as peroxidase. In some embodiments, the antibody is an antibody fragment (e.g., Fab, Fab'-SH, Fv, scFv, or $F(ab')_2$ fragments) or an antibody derivative thereof.

The antibodies disclosed herein may also be coupled to a labeling group, e.g., an radioisotope, radionuclide, an enzymatic group, biotinyl group, a nucleic acid, oligonucleotide, enzyme, or a fluorescent label. A labeling group may be coupled to the antibody via a spacer arm of any suitable length to reduce potential steric hindrance. Various methods for labeling proteins are known in the art and can be used to prepare such labeled antibodies.

Various routes of administration are contemplated. Such methods of administration include but are not limited to, topical, parenteral, subcutaneous, intraperitoneal, intrapulmonary, intrathecal, intranasal, and intralesional administration. Parenteral infusions include intramuscular, intravenous, intraarterial, intraperitoneal, or subcutaneous administration. Suitable antibodies include antibodies that bind to complement component C1q, C1r, or C1s. Such antibodies include monoclonal antibodies, human antibodies, chimeric antibodies, humanized antibodies, antibody fragments, and/or antibody derivatives thereof. In some embodiments, the antibody is humanized antibody. In some embodiments, the antibody is antibody fragment, such as a Fab fragment.

In some embodiments, antibodies are human monoclonal antibodies which may be prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline and/or non-germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

In some embodiments, antibodies are humanized and/or chimeric monoclonal antibodies, which can be raised by immunizing rodents (e.g., mice, rats, hamsters and guinea pigs) with either (1) the native complement component (e.g., C1q, C1r, or C1s) derived from enzymatic digestion of a purified complement component from human plasma or serum, or (2) a recombinant complement component, or its derived fragment, expressed by either eukaryotic or prokaryotic systems. Other animals can be used for immunization, e.g., non-human primates, transgenic mice expressing human immunoglobulins, and severe combined immunodeficient (SCID) mice transplanted with human B-lymphocytes.

Polyclonal and monoclonal antibodies are naturally generated as immunoglobulin (Ig) molecules in the immune system's response to a pathogen. A dominating format with a concentration of 8 mg/ml in human serum, the ~150-kDa IgG1 molecule is composed of two identical ~50-kDa heavy chains and two identical ~25-kDa light chains.

Hybridomas can be generated by conventional procedures by fusing B-lymphocytes from the immunized animals with myeloma cells. In addition, anti-C1q, -C1r, or -C1s antibodies can be generated by screening recombinant single-chain Fv or Fab libraries from human B-lymphocytes in a phage-display system. The specificity of the MAbs to human C1q, C1r, or C1s can be tested by enzyme linked immunosorbent assay (ELISA), Western immunoblotting, or other immunochemical techniques.

The inhibitory activity on complement activation of antibodies identified in the screening process can be assessed by hemolytic assays using either unsensitized rabbit or guinea pig RBCs for the alternative complement pathway, or sensitized chicken or sheep RBCs for the classical complement pathway. Those hybridomas that exhibit an inhibitory activity specific for the classical complement pathway are cloned by limiting dilution. The antibodies are purified for characterization for specificity to human C1q, C1r, or C1s by the assays described above.

Based on the molecular structures of the variable regions of the anti-C1q, -C1r, or -C1s antibodies, molecular modeling and rational molecular design may be used to generate and screen small molecules that mimic the molecular structures of the binding region of the antibodies and inhibit the activities of C1q, C1r, or C1s. These small molecules can be peptides, peptidomimetics, oligonucleotides, or organic compounds. The mimicking molecules can be used as inhibitors of complement activation in inflammatory indications and autoimmune diseases. Alternatively, one can use large-scale screening procedures commonly used in the field to isolate suitable small molecules from libraries of combinatorial compounds.

A suitable dosage can be determined by the skilled artisan using a variety of well-known methodologies, including the use of animal models as well as clinical trials and then following the conventional methodology for determining optimal dosages, i.e., administering various dosages and determining which doses provide suitable efficacy without undesirable side-effects.

Before the advent of recombinant DNA technology, proteolytic enzymes (proteases) that cleave polypeptide sequences were used to dissect the structure of antibody molecules and to determine which parts of the molecule are responsible for its various functions. Limited digestion with the protease papain cleaves antibody molecules into three fragments. Two fragments, known as Fab fragments, are identical and contain the antigen-binding activity. The Fab fragments correspond to the two identical arms of the antibody molecule, each of which consists of a complete light chain paired with the $V_H$ and $C_H1$ domains of a heavy chain. The other fragment contains no antigen binding activity but was originally observed to crystallize readily, and for this reason was named the Fc fragment (Fragment crystallizable).

A Fab molecule is an artificial ~50-kDa fragment of the Ig molecule with a heavy chain lacking constant domains $C_H2$ and $C_H3$. Two heterophilic ($V_L$-$V_H$ and $C_L$-$C_H1$) domain interactions underlie the two-chain structure of the Fab molecule, which is further stabilized by a disulfide bridge between $C_L$ and $C_H1$. Fab and IgG have identical antigen binding sites formed by six complementarity-determining regions (CDRs), three each from $V_L$ and $V_H$ (LCDR1, LCDR2, LCDR3 and HCDR1, HCDR2, HCDR3). The CDRs define the hypervariable antigen binding site of antibodies. The highest sequence variation is found in LCDR3 and HCDR3, which in natural immune systems are generated by the rearrangement of $V_L$ and $J_L$ genes or $V_H$, $D_H$ and $J_H$ genes, respectively. LCDR3 and HCDR3 typically form the core of the antigen binding site. The conserved regions that connect and display the six CDRs are referred to as framework regions. In the three-dimensional structure of the variable domain, the framework regions form a sandwich of two opposing antiparallel β-sheets that are linked by hypervariable CDR loops on the outside and by a conserved disulfide bridge on the inside.

Methods are disclosed herein for protecting or treating an individual suffering from a blood disorder, such as cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin. Complement activation on blood and endothelial cells activates platelets, monocytes, neutrophils, red blood cells as well as endothelial cells promoting thrombotic and inflammatory damage. These findings have broad implications for a variety of clinical conditions, particularly blood disorders where complement activation is involved. Complement activation is inhibited by contacting complement proteins with inhibitors or antagonists of the complement pathway. For example, inhibitors can block activation of the complement cascade, can block the expression of specific complement proteins in blood cells, can interfere with signaling molecules that induce complement activation, can upregulate expression of complement inhibitors in blood cells, and otherwise interfere with the role of complement in a blood disorder. The ability to prevent complement activation has important implications for maintaining normal blood function in a variety of blood disorders.

The present disclosure also provides a method of detecting complement activation in an individual, by a) administering an antibody from any of the embodiments to the subject, wherein the antibody is coupled to a detectable label; (b) detecting the detectable label to measure the amount or location of the antibody in the subject; and (c) comparing the amount or location of the antibody to a reference, wherein the risk of developing a blood disorder associated with complement activation is characterized based on the comparison of the amount of antibody as compared to the reference. For example, the detectable label may comprise a nucleic acid, oligonucleotide, enzyme, radioactive isotope, biotin, or a fluorescent label (e.g., fluorescein, rhodamine, cyanine dyes or BODIPY). The detectable label may be detected using an imaging agent for x-ray, CT, MRI, ultrasound, PET and SPECT.

It is to be understood that one, some, or all of the properties of the various embodiments described herein may be combined to form other embodiments of the compositions and methods provided herein. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein. These and other aspects of the compositions and methods provided herein will become apparent to one of skill in the art.

The publications discussed herein are provided solely for their disclosure prior to the filing date of the present application. Nothing herein is to be construed as an admission that the present invention is not entitled to antedate such publication by virtue of prior invention. Further, the dates of publication provided can be different from the actual publication dates, which may need to be independently confirmed.

Anti-Complement C1q Antibodies

The anti-C1q antibodies disclosed herein are potent inhibitors of C1q and can be dosed for continuous inhibition of C1q function over any period, and then optionally withdrawn to allow for return of normal C1q function at times when its activity may be important. Results obtained with anti-C1q antibodies disclosed herein in animal studies can be readily carried forward into the clinic with humanized or human antibodies, as well as with fragments and/or derivatives thereof.

C1q is a large multimeric protein of 460 kDa consisting of 18 polypeptide chains (6 C1q A chains, 6 C1q B chains, and 6 C1q C chains). C1r and C1s complement proteins bind to the C1q tail region to form the C1 complex ($C1qr_2s_2$).

The antibodies of this disclosure specifically recognize complement factor C1q and/or C1q in the C1 complex of the classical complement activation pathway. The bound complement factor may be derived, without limitation, from any organism having a complement system, including any mammalian organism such as human, mouse, rat, rabbit, monkey, dog, cat, cow, horse, camel, sheep, goat, or pig.

As used herein "C1 complex" refers to a protein complex that may include, without limitation, one C1q protein, two C1r proteins, and two C1s proteins (e.g., $C1qr^2s^2$).

Anti-C1q antibodies disclosed herein may inhibit C1 complex formation.

As used herein "complement factor C1q" refers to both wild type sequences and naturally occurring variant sequences.

A non-limiting example of a complement factor C1q recognized by antibodies of this disclosure is human C1q, including the three polypeptide chains A, B, and C:

C1q, chain A (I), Accession No. Protein Data Base: NP_057075.1; GenBank No.: NM_015991: >gi|7705753|ref|NP_057075.1|complement C1q subcomponent subunit A precursor [*Homo sapiens*]

(SEQ ID NO: 1)

MEGPRGWLVLCVLAISLASMVTEDLCRAPDGKKGEAGRPGRRGRPGLKGEQGEPGAPG

IRTGIQGLKGDQGEPGPSGNPGKVGYPGPSGPLGARGIPGIKGTKGSPGNIKDQPRPAFSA

IRRNPPMGGNVVIFDTVITNQEEPYQNHSGRFVCTVPGYYYFTFQVLSQWEICLSIVSSSR

GQVRRSLGFCDTTNKGLFQVVSGGMVLQLQQGDQVWVEKDPKKGHIYQGSEADSVFS

GFLIFPSA.

C1q, chain B (*homo sapiens*), Accession No. Protein Data Base: NP_000482.3; GenBank No.: NM_000491.3: >gi|87298828|ref|NP_000482.3|complement C1q subcomponent subunit B precursor [*Homo sapiens*]

(SEQ ID NO: 2)

MMMKIPWGSIPVLMLLLLLGLIDISQAQLSCTGPPAIPGIPGIPGTPGPDGQPGTPGIKGEK

GLPGLAGDHGEFGEKGDPGIPGNPGKVGPKGPMGPKGGPGAPGAPGPKGESGDYKATQ

KIAFSATRTINVPLRRDQTIRFDHVITNMNNNYEPRSGKFTCKVPGLYYFTYHASSRGNL

CVNLMRGRERAQKVVTFCDYAYNTFQVTTGGMVLKLEQGENVFLQATDKNSLLGME

GANSIFSGFLLFPDMEA.

C1q, chain C (*homo sapiens*), Accession No. Protein Data Base: NP_001107573.1; GenBank No.: NM_001114101.1: >gi|166235903|ref|NP_001107573.1|complement C1q subcomponent subunit C precursor [*Homo sapiens*]

(SEQ ID NO: 3)

MDVGPSSLPHLGLKLLLLLLLLPLRGQANTGCYGIPGMPGLPGAPGKDGYDGLPGPKGE

PGIPAIPGIRGPKGQKGEPGLPGHPGKNGPMGPPGMPGVPGPMGIPGEPGEEGRYKQKF

QSVFTVTRQTHQPPAPNSLIRFNAVLTNPQGDYDTSTGKFTCKVPGLYYFVYHASHTAN

LCVLLYRSGVKVVTFCGHTSKTNQVNSGGVLLRLQVGEEVWLAVNDYYDMVGIQGSD

SVFSGFLLFPD.

Accordingly, an anti-C1q antibody of the present disclosure may bind to polypeptide chain A, polypeptide chain B, and/or polypeptide chain C of a C1q protein. In some embodiments, an anti-C1q antibody of the present disclosure binds to polypeptide chain A, polypeptide chain B, and/or polypeptide chain C of human C1q or a homolog thereof, such as mouse, rat, rabbit, monkey, dog, cat, cow, horse, camel, sheep, goat, or pig C1q. In some embodiments, the anti-C1q antibody is a human antibody, a humanized antibody, a chimeric antibody, or a fragment thereof or a derivative thereof. In some embodiments, the antibody is humanized antibody. In some embodiments, the antibody is antibody fragment, such as a Fab fragment.

Suitable antibodies include an antibody that binds complement C1q protein (i.e., an anti-complement C1q antibody, also referred to herein as an anti-C1q antibody and a C1q antibody) and a nucleic acid molecule that encodes such an antibody for a method of preventing, reducing risk of developing, or treating a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin).

All sequences mentioned in the following twenty paragraphs are incorporated by reference from U.S. Pat. No. 9,708,394, which is hereby incorporated by reference for the antibodies and related compositions that it discloses.

Light Chain and Heavy Chain Variable Domain Sequences of Antibody M1 (Mab2)

Using standard techniques, the nucleic acid and amino acid sequences encoding the light chain variable and the heavy chain variable domain of antibody M1 were determined. The amino acid sequence of the light chain variable domain of antibody M1 is:

(SEQ ID NO: 4)
DVQITQSPSYLAASPGETITINCRASKSINKYLAWYQEKPGKTNKLLIY
SGSTLQSGIPSRFSGSGSGTDFTLTISSLEPEDFAMYYCQQHNEYPLTF
GAGTKLELK

The hyper variable regions (HVRs) of the light chain variable domain are depicted in bolded and underlined text. In some embodiments, the HVR-L1 of the M1 light chain variable domain has the sequence RASKSINKYLA (SEQ ID NO:5), the HVR-L2 of the M1 light chain variable domain has the sequence SGSTLQS (SEQ ID NO:6), and the HVR-L3 of the M1 light chain variable domain has the sequence QQHNEYPLT (SEQ ID NO:7).

The amino acid sequence of the heavy chain variable domain of antibody M1 is:

(SEQ ID NO: 8)
QVQLQQPGAELVKPGASVKLSCKSSGYHFTSYWMHWVKQRPGQGLEWIG
VIHPNSGSINYNEKFESKATLTVDKSSSTAYMQLSSLTSEDSAVYYCAG
ERDSTEVLPMDYWGQGTSVTVSS

The hyper variable regions (HVRs) of the heavy chain variable domain are depicted in bolded and underlined text. In some embodiments, the HVR-H1 of the M1 heavy chain variable domain has the sequence GYHFTSYWVNM (SEQ ID NO:9), the HVR-H2 of the M1 heavy chain variable domain has the sequence VIHPNSGSINYNEKFES (SEQ ID NO: 10), and the HVR-H3 of the M1 heavy chain variable domain has the sequence ERDSTEVLPMDY (SEQ ID NO: 11).

The nucleic acid sequence encoding the light chain variable domain was determined to be:

(SEQ ID NO: 12)
GATGTCCAGATAACCCAGTCTCCATCTTATCTTGCTGCATCTCCTGGAG

AAACCATTACTATTAATTGCAGGGCAAGTAAGAGCATTAACAAATATTT

AGCCTGGTATCAAGAGAAACCTGGGAAAACTAATAAGCTTCTTATCTAC

TCTGGATCCACTTTGCAATCTGGAATTCCATCAAGGTTCAGTGGCAGTG

GATCTGGTACAGATTTCACTCTCACCATCAGTAGCCTGGAGCCTGAAGA

TTTTGCAATGTATTACTGTCAACAACATAATGAATACCCGCTCACGTTC

GGTGCTGGGACCAAGCTGGAGCTGAAA

The nucleic acid sequence encoding the heavy chain variable domain was determined to be:

(SEQ ID NO: 13)
CAGGTCCAACTGCAGCAGCCTGGGGCTGAGCTGGTAAAGCCTGGGGCTT

CAGTGAAGTTGTCCTGCAAGTCTTCTGGCTACCATTTCACCAGCTACTG

GATGCACTGGGTGAAGCAGAGGCCTGGACAAGGCCTTGAGTGGATTGGA

GTGATTCATCCTAATAGTGGTAGTATTAACTACAATGAGAAGTTCGAGA

GCAAGGCCACACTGACTGTAGACAAATCCTCCAGCACAGCCTACATGCA

ACTCAGCAGCCTGACATCTGAGGACTCGGCGGTCTATTATTGTGCAGGA

GAGAGAGATTCTACGGAGGTTCTCCCTATGGACTACTGGGGTCAAGGAA

CCTCAGTCACCGTCTCCTCA.

Deposit of Material

The following materials have been deposited according to the Budapest Treaty in the American Type Culture Collection, ATCC Patent Depository, 10801 University Blvd., Manassas, Va. 20110-2209, USA (ATCC):

| | Deposit ATCC | | |
|---|---|---|---|
| Sample ID | Isotype | Date | Accession No. |
| Mouse hybridoma C1qM1 7788-1(M) 051613 producing anti-C1q antibody M1 | IgG1, kappa | Jun. 6, 2013 | PTA-120399 |

The hybridoma cell line producing the M1 antibody (mouse hybridoma C1qM1 7788-1(M) 051613) has been deposited with ATCC under conditions that assure that access to the culture will be available during pendency of the patent application and for a period of 30 years, or 5 years after the most recent request, or for the effective life of the patent, whichever is longer. A deposit will be replaced if the deposit becomes nonviable during that period. The deposit is available as required by foreign patent laws in countries wherein counterparts of the subject application, or its progeny are filed. However, it should be understood that the availability of the deposit does not constitute a license to practice the subject invention in derogation of patent rights granted by governmental action.

Disclosed herein are methods of administering an anti-C1q antibody comprising a light chain variable domain and a heavy chain variable domain. The antibody may bind to at least human C1q, mouse C1q, or rat C1q. The antibody may be a humanized antibody, a chimeric antibody, or a human antibody. The antibody may be a monoclonal antibody, an antibody fragment thereof, and/or an antibody derivative thereof. In some embodiments, the antibody is humanized antibody. In some embodiments, the antibody is antibody fragment, such as a Fab fragment. The light chain variable domain comprises the HVR-L1, HVR-L2, and HVR-L3 of the monoclonal antibody M1 produced by a hybridoma cell line deposited with Accession Number PTA-120399. The heavy chain variable domain comprises the HVR-H1, HVR-H2, and HVR-H3 of the monoclonal antibody M1 produced by a hybridoma cell line deposited with ATCC Accession Number PTA-120399.

In some embodiments, the amino acid sequence of the light chain variable domain and heavy chain variable domain comprise one or more of SEQ ID NO:5 of HVR-L1, SEQ ID NO:6 of HVR-L2, SEQ ID NO:7 of HVR-L3, SEQ ID NO:9 of HVR-H1, SEQ ID NO:10 of HVR-H2, and SEQ ID NO:11 of HVR-H3.

The antibody may comprise a light chain variable domain amino acid sequence that is at least 85%, 90%, or 95% identical to SEQ ID NO:4, preferably while retaining the HVR-L1 RASKSINKYLA (SEQ ID NO:5), the HVR-L2 SGSTLQS (SEQ ID NO:6), and the HVR-L3 QQHNEYPLT (SEQ ID NO:7). The antibody may comprise a heavy chain variable domain amino acid sequence that is at least 85%, 90%, or 95% identical to SEQ ID NO:8, preferably while retaining the HVR-H1 GYHFTSYWMH (SEQ ID NO:9), the HVR-H2 VIHPNSGSINYNEKFES (SEQ ID NO: 10), and the HVR-H3 ERDSTEVLPMDY (SEQ ID NO:11).

Disclosed herein are methods of administering an anti-C1q antibody, which inhibits the interaction between C1q and an autoantibody. In preferred embodiments, the anti-C1q antibody causes clearance of C1q from the circulation or tissue.

In some embodiments, the anti-C1q antibody of this disclosure inhibits the interaction between C1q and C1s. In some embodiments, the anti-C1q antibody inhibits the interaction between C1q and C1r. In some embodiments the anti-C1q antibody inhibits the interaction between C1q and C1s and between C1q and C1r. In some embodiments, the anti-C1q antibody inhibits the interaction between C1q and another antibody, such as an autoantibody. In preferred embodiments, the anti-C1q antibody causes clearance of C1q from the circulation or tissue. In some embodiments, the anti-C1q antibody inhibits the respective interactions, at a stoichiometry of less than 2.5:1; 2.0:1; 1.5:1; or 1.0:1. In some embodiments, the C1q antibody inhibits an interaction, such as the C1q-C1s interaction, at approximately equimolar concentrations of C1q and the anti-C1q antibody. In other embodiments, the anti-C1q antibody binds to C1q with a stoichiometry of less than 20:1; less than 19.5:1; less than 19:1; less than 18.5:1; less than 18:1; less than 17.5:1; less than 17:1; less than 16.5:1; less than 16:1; less than 15.5:1; less than 15:1; less than 14.5:1; less than 14:1; less than 13.5:1; less than 13:1; less than 12.5:1; less than 12:1; less than 11.5:1; less than 11:1; less than 10.5:1; less than 10:1; less than 9.5:1; less than 9:1; less than 8.5:1; less than 8:1; less than 7.5:1; less than 7:1; less than 6.5:1; less than 6:1; less than 5.5:1; less than 5:1; less than 4.5:1; less than 4:1; less than 3.5:1; less than 3:1; less than 2.5:1; less than 2.0:1; less than 1.5:1; or less than 1.0:1. In certain embodiments, the anti-C1q antibody binds C1q with a binding stoichiometry that ranges from 20:1 to 1.0:1 or less than 1.0:1. In certain embodiments, the anti-C1q antibody binds C1q with a binding stoichiometry that ranges from 6:1 to 1.0:1 or less than 1.0:1. In certain embodiments, the anti-C1q antibody binds C1q with a binding stoichiometry that ranges from 2.5:1 to 1.0:1 or less than 1.0:1. In some embodiments, the anti-C1q antibody inhibits the interaction between C1q and C1r, or between C1q and C1s, or between C1q and both C1r and C1s. In some embodiments, the anti-C1q antibody inhibits the interaction between C1q and C1r, between C1q and C1s, and/or between C1q and both C1r and C1s. In some embodiments, the anti-C1q antibody binds to the C1q A-chain. In other embodiments, the anti-C1q antibody binds to the C1q B-chain. In other embodiments, the anti-C1q antibody binds to the C1q C-chain. In some embodiments, the anti-C1q antibody binds to the C1q A-chain, the C1q B-chain and/or the C1q C-chain. In some embodiments, the anti-C1q antibody binds to the globular domain of the C1q A-chain, B-chain, and/or C-chain. In other embodiments, the anti-C1q antibody binds to the collagen-like domain of the C1q A-chain, the C1q B-chain, and/or the C1q C-chain.

Where antibodies of this disclosure inhibit the interaction between two or more complement factors, such as the interaction of C1q and C1s, or the interaction between C1q and C1r, the interaction occurring in the presence of the antibody may be reduced by at least 10%, at least 20%, at least 30%, at least 40%, at least 50%, at least 60%, at least 70%, at least 80%, at least 90%, at least 95%, or at least 99% relative to a control wherein the antibodies of this disclosure are absent. In some embodiments, antibodies of this disclosure reduces the interaction between two or more complement factors by 50%, 60%, 70%, 80%, 90%, or 100%. In certain embodiments, the interaction occurring in the presence of the antibody is reduced by an amount that ranges from at least 30% to at least 99% relative to a control wherein the antibodies of this disclosure are absent.

In some embodiments, the antibodies of this disclosure inhibit C2 or C4-cleavage by at least 20%, at least 30%, at least 40%, at least 50%, at least 60%, at least 70%, at least 80%, at least 90%, at least 95%, or at least 99%, or by an amount that ranges from at least 30% to at least 99%, relative to a control wherein the antibodies of this disclosure are absent. Methods for measuring C2 or C4-cleavage are well known in the art. The $EC_{50}$ values for antibodies of this disclosure with respect C2 or C4-cleavage may be less than 3 μg/ml; 2.5 μg/ml; 2.0 μg/ml; 1.5 μg/ml; 1.0 μg/ml; 0.5 μg/ml; 0.25 μg/ml; 0.1 μg/ml; 0.05 μg/ml. In some embodiments, the antibodies of this disclosure inhibit C2 or C4-cleavage at approximately equimolar concentrations of C1q and the respective anti-C1q antibody.

In some embodiments, the antibodies of this disclosure inhibit autoantibody-dependent and complement-dependent cytotoxicity (CDC) by at least 20%, at least 30%, at least 40%, at least 50%, at least 60%, at least 70%, at least 80%, at least 90%, at least 95%, or at least 99%, or by an amount that ranges from at least 30% to at least 99%, relative to a control wherein the antibodies of this disclosure are absent. The $EC_{50}$ values for antibodies of this disclosure with respect to inhibition of autoantibody-dependent and complement-dependent cytotoxicity may be less than 3 μg/ml; 2.5 μg/ml; 2.0 μg/ml; 1.5 μg/ml; 1.0 μg/ml; 0.5 μg/ml; 0.25 μg/ml; 0.1 μg/ml; 0.05 μg/ml.

In some embodiments, the antibodies of this disclosure inhibit complement-dependent cell-mediated cytotoxicity (CDCC) by at least 20%, at least 30%, at least 40%, at least 50%, at least 60%, at least 70%, at least 80%, at least 90%, at least 95%, or at least 99%, or by an amount that ranges from at least 30% to at least 99%, relative to a control wherein the antibodies of this disclosure are absent. Methods for measuring CDCC are well known in the art. The $EC_{50}$ values for antibodies of this disclosure with respect CDCC inhibition may be 1 less than 3 μg/ml; 2.5 μg/ml; 2.0 μg/ml; 1.5 μg/ml; 1.0 μg/ml; 0.5 μg/ml; 0.25 μg/ml; 0.1 μg/ml; 0.05 μg/ml. In some embodiments, the antibodies of this disclosure inhibit CDCC but not antibody-dependent cellular cytotoxicity (ADCC).

Humanized Anti-Complement C1q Antibodies

Humanized antibodies of the present disclosure specifically bind to a complement factor C1q and/or C1q protein in the C1 complex of the classical complement pathway. The humanized anti-C1q antibody may specifically bind to human C1q, human and mouse C1q, to rat C1q, or human C1q, mouse C1q, and rat C1q.

All sequences mentioned in the following sixteen paragraphs are incorporated by reference from U.S. patent application Ser. No. 14/933,517, which is hereby incorporated by reference for the antibodies and related compositions that it discloses.

In some embodiments, the human heavy chain constant region is a human IgG4 heavy chain constant region comprising the amino acid sequence of SEQ ID NO:47, or with at least 70%, at least about 75%, at least about 80%, at least about 85%, at least about 90% homology to SEQ ID NO: 47. The human IgG4 heavy chain constant region may comprise an Fc region with one or more modifications and/or amino acid substitutions according to Kabat numbering. In such cases, the Fc region comprises a leucine to glutamate amino acid substitution at position 248, wherein such a substitution inhibits the Fc region from interacting with an Fc receptor. In some embodiments, the Fc region comprises a serine to proline amino acid substitution at position 241, wherein such a substitution prevents arm switching in the antibody.

The amino acid sequence of human IgG4 (S241P L248E) heavy chain constant domain is:

(SEQ ID NO: 47)
ASTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRV

ESKYGPPCPPCPAPEFEGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK.

The antibody may comprise a heavy chain variable domain and a light chain variable domain, wherein the heavy chain variable domain comprises an amino acid sequence selected from any one of SEQ ID NOs: 31-34, or an amino acid sequence with at least about 90% homology to the amino acid sequence selected from any one of SEQ ID NOs: 31-34. In certain such embodiments, the light chain variable domain comprises an amino acid sequence selected from any one of SEQ ID NOs: 35-38, or an amino acid sequence with at least about 90% homology to the amino acid sequence selected from any one of SEQ ID NOs: 35-38.

The amino acid sequence of heavy chain variable domain variant 1 (VH1) is:

(SEQ ID NO: 31)
QVQLVQSGAELKKPGASVKVSCKSSGYHFTSYWMHWVKQAPGQGLEWIG
VIHPNSGSINYNEKFESKATITVDKSTSTAYMQLSSLTSEDSAVYYCAG
ERDSTEVLPMDYWGQGTSVTVSS.

The hyper variable regions (HVRs) of VH1 are depicted in bolded and underlined text.

The amino acid sequence of heavy chain variable domain variant 2 (VH2) is:

(SEQ ID NO: 32)
QVQLVQSGAELKKPGASVKVSCKSSGYHFTSYWMHWVKQAPGQGLEWIG
VIHPNSGSINYNEKFESRATITVDKSTSTAYMELSSLRSEDTAVYYCAG
ERDSTEVLPMDYWGQGTTVTVSS.

The hyper variable regions (HVRs) of VH2 are depicted in bolded and underlined text.

The amino acid sequence of heavy chain variable domain variant 3 (VH3) is:

(SEQ ID NO: 33)
QVQLVQSGAELKKPGASVKVSCKSSGYHFTSYWMHWVKQAPGQGLEWIG
VIHPNSGSINYNEKFESRVTITVDKSTSTAYMELSSLRSEDTAVYYCAG
ERDSTEVLPMDYWGQGTTVTVSS.

The hyper variable regions (HVRs) of VH3 are depicted in bolded and underlined text.

The amino acid sequence of heavy chain variable domain variant 4 (VH4) is:

(SEQ ID NO: 34)
QVQLVQSGAELKKPGASVKVSCKSSGYHFTSYWMHWVRQAPGQGLEWIG
VIHPNSGSINYNEKFESRVTITVDKSTSTAYMELSSLRSEDTAVYYCAG
ERDSTEVLPMDYWGQGTTVTVSS.

The hyper variable regions (HVRs) of VH4 are depicted in bolded and underlined text.

The amino acid sequence of kappa light chain variable domain variant 1 (Vκ1) is:

(SEQ ID NO: 35)
DVQITQSPSYLAASLGERATINCRASKSINKYLAWYQQKPGKTNKLLIY
SGSTLQSGIPARFSGSGSGTDFTLTISSLEPEDFAMYYCQQHNEYPLTF
GQGTKLEIK

The hyper variable regions (HVRs) of Vκ1 are depicted in bolded and underlined text.

The amino acid sequence of kappa light chain variable domain variant 2 (Vκ2) is:

(SEQ ID NO: 36)
DVQITQSPSSLSASLGERATINCRASKSINKYLAWYQQKPGKANKLLIY
SGSTLQSGIPARFSGSGSGTDFTLTISSLEPEDFAMYYCQQHNEYPLTF
GQGTKLEIK.

The hyper variable regions (HVRs) of Vκ2 are depicted in bolded and underlined text.

The amino acid sequence of kappa light chain variable domain variant 3 (Vκ3) is:

(SEQ ID NO: 37)
DVQITQSPSSLSASLGERATINCRASKSINKYLAWYQQKPGKAPKLLIY
SGSTLQSGIPARFSGSGSGTDFTLTISSLEPEDFAMYYCQQHNEYPLTF
GQGTKLEIK.

The hyper variable regions (HVRs) of Vκ3 are depicted in bolded and underlined text.

The amino acid sequence of kappa light chain variable domain variant 4 (Vκ4) is:

(SEQ ID NO: 38)
DIQLTQSPSSLSASLGERATINCRASKSINKYLAWYQQKPGKAPKLLIY
SGSTLQSGIPARFSGSGSGTDFTLTISSLEPEDFAMYYCQQHNEYPLTF
GQGTKLEIK.

The hyper variable regions (HVRs) of Vκ4 are depicted in bolded and underlined text.

The antibody may comprise a light chain variable domain amino acid sequence that is at least 85%, 90%, or 95% identical to SEQ ID NO:35-38 while retaining the HVR-L1 RASKSINKYLA (SEQ ID NO:5), the HVR-L2 SGSTLQS (SEQ ID NO:6), and the HVR-L3 QQHNEYPLT (SEQ ID NO:7). The antibody may comprise a heavy chain variable domain amino acid sequence that is at least 85%, 90%, or 95% identical to SEQ ID NO:31-34 while retaining the HVR-H1 GYHFTSYWMH (SEQ ID NO:9), the HVR-H2 VIHPNSGSINYNEKFES (SEQ ID NO: 10), and the HVR-H3 ERDSTEVLPMDY (SEQ ID NO:11).

In some embodiments, the antibody comprises a light chain variable domain amino acid sequence of SEQ ID NO: 35 and a heavy chain variable domain amino acid sequence of SEQ ID NO: 31. In some embodiments, the antibody comprises a light chain variable domain amino acid sequence of SEQ ID NO: 36 and a heavy chain variable domain amino acid sequence of SEQ ID NO: 32. In some embodiments, the antibody comprises a light chain variable domain amino acid sequence of SEQ ID NO: 37 and a heavy chain variable domain amino acid sequence of SEQ ID NO: 33. In some embodiments, the antibody comprises a light chain variable domain amino acid sequence of SEQ ID NO: 38 and a heavy chain variable domain amino acid sequence of SEQ ID NO: 34.

In some embodiments, humanized anti-C1q antibodies of the present disclosure include a heavy chain variable region that contains an Fab region and a heavy chain constant regions that contains an Fc region, where the Fab region specifically binds to a C1q protein of the present disclosure, but the Fc region is incapable of binding the C1q protein. In some embodiments, the Fc region is from a human IgG1, IgG2, IgG3, or IgG4 isotype. In some embodiments, the Fc region is incapable of inducing complement activity and/or incapable of inducing antibody-dependent cellular cytotoxicity (ADCC). In some embodiments, the Fc region comprises one or more modifications, including, without limitation, amino acid substitutions. In certain embodiments, the Fc region of humanized anti-C1q antibodies of the present disclosure comprise an amino acid substitution at position 248 according to Kabat numbering convention or a position corresponding to position 248 according to Kabat numbering convention, and/or at position 241 according to Kabat numbering convention or a position corresponding to position 241 according to Kabat numbering convention. In some embodiments, the amino acid substitution at position 248 or a positions corresponding to position 248 inhibits the Fc region from interacting with an Fc receptor. In some embodiments, the amino acid substitution at position 248 or a positions corresponding to position 248 is a leucine to glutamate amino acid substitution. In some embodiments, the amino acid substitution at position 241 or a positions corresponding to position 241 prevents arm switching in the antibody. In some embodiments, the amino acid substitution at position 241 or a positions corresponding to position 241 is a serine to proline amino acid substitution. In certain embodiments, the Fc region of humanized anti-C1q antibodies of the present disclosure comprises the amino acid sequence of SEQ ID NO: 47, or an amino acid sequence with at least about 70%, at least about 75%, at least about 80% at least about 85% at least about 90%, or at least about 95% homology to the amino acid sequence of SEQ ID NO: 47.

Anti-C1q Fab Fragment

Before the advent of recombinant DNA technology, proteolytic enzymes (proteases) that cleave polypeptide sequences have been used to dissect the structure of antibody molecules and to determine which parts of the molecule are responsible for its various functions. Limited digestion with the protease papain cleaves antibody molecules into three fragments. Two fragments, known as Fab fragments, are identical and contain the antigen-binding activity. The Fab fragments correspond to the two identical arms of the antibody molecule, each of which consists of a complete light chain paired with the $V_H$ and $C_H1$ domains of a heavy chain. The other fragment contains no antigen binding activity but was originally observed to crystallize readily, and for this reason was named the Fc fragment (Fragment crystallizable). When Fab molecules were compared to IgG molecules, it was found that Fab are superior to IgG for certain in vivo applications due to their higher mobility and tissue penetration capability, their reduced circulatory half-life, their ability to bind antigen monovalently without mediating antibody effector functions, and their lower immunogenicity.

The Fab molecule is an artificial ~50-kDa fragment of the Ig molecule with a heavy chain shortened by constant domains $C_H2$ and $C_H3$. Two heterophilic ($V_L$-$V_H$ and $C_L$-$C_H1$) domain interactions underlie the two-chain structure of the Fab molecule, which is further stabilized by a disulfide bridge between $C_L$ and $C_H1$. Fab and IgG have identical antigen binding sites formed by six complementarity-determining regions (CDRs), three each from $V_L$ and $V_H$ (LCDR1, LCDR2, LCDR3 and HCDR1, HCDR2, HCDR3). The CDRs define the hypervariable antigen binding site of antibodies. The highest sequence variation is found in LCDR3 and HCDR3, which in natural immune systems are generated by the rearrangement of $V_L$ and $J_L$ genes or $V_H$, $D_H$ and $J_H$ genes, respectively. LCDR3 and HCDR3 typically form the core of the antigen binding site. The conserved regions that connect and display the six CDRs are referred to as framework regions. In the three-dimensional structure of the variable domain, the framework regions form a sandwich of two opposing antiparallel β-sheets that are linked by hypervariable CDR loops on the outside and by a conserved disulfide bridge on the inside. This unique combination of stability and versatility of the antigen binding site of Fab and IgG underlie its success in clinical practice for the diagnosis, monitoring, prevention, and treatment of disease.

All anti-C1q antibody Fab fragment sequences are incorporated by reference from U.S. patent application Ser. No. 15/360,549, which is hereby incorporated by reference for the antibodies and related compositions that it discloses.

In certain embodiments, the present disclosure provides an anti-C1q antibody Fab fragment that binds to a C1q protein comprising a heavy ($V_H$/$C_H1$) and light chain ($V_L$/$C_L$), wherein the anti-C1q antibody Fab fragment has six complementarity determining regions (CDRs), three each from $V_L$ and $V_H$ (HCDR1, HCDR2, HCDR3, and LCDR1, LCDR2, LCDR3). The heavy chain of the antibody Fab fragment is truncated after the first heavy chain domain of IgG1 (SEQ ID NO: 39), and comprises the following amino acid sequence:

(SEQ ID NO: 39)

QVQLVQSGAELKKPGASVKVSCKSSGYHFTSYWMHWVKQAPGQGLEWIG

VIHPNSGSINYNEKFESRVTITVDKSTSTAYMELSSLRSEDTAVYYCAG

ERDSTEVLPMDYWGQGTTVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHT

The complementarity determining regions (CDRs) of SEQ ID NO:1 are depicted in bolded and underlined text.

The light chain domain of the antibody Fab fragment comprises the following amino acid sequence (SEQ ID NO: 40):

(SEQ ID NO: 40)

DVQITQSPSSLSASLGERATINCRASKSINKYLAWYQQKPGKAPKLLIY

SGSTLQSGIPARFSGSGSGTDFTLTISSLEPEDFAMYYCQQHNEYPLTF

GQGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

The complementarity determining regions (CDRs) of SEQ ID NO:2 are depicted in bolded and underlined text.

Anti-Complement C1s Antibodies

Suitable inhibitors include an antibody that binds complement C1s protein (i.e., an anti-complement C1s antibody, also referred to herein as an anti-C1s antibody and a C1s antibody) and a nucleic acid molecule that encodes such an antibody. Complement C1s is an attractive target as it is upstream in the complement cascade and has a narrow range of substrate specificity. Furthermore it is possible to obtain antibodies (for example, but not limited to, monoclonal antibodies) that specifically bind the activated form of C1s.

All sequences mentioned in the following two paragraphs are incorporated by reference from U.S. patent application Ser. No. 14/890,811, which is hereby incorporated by reference for the antibodies and related compositions that it discloses.

In certain aspects, disclosed herein are methods of administering an anti-C1s antibody. The antibody may be a murine, humanized, or chimeric antibody. In some embodiments, the light chain variable domain comprises HVR-L1, HVR-L2, and HVR-L3, and the heavy chain comprises HVR-H1, HVR-H2, and HVR-H3 of a murine anti-human C1s monoclonal antibody 5A1 produced by a hybridoma cell line deposited with ATCC on May 15, 2013 or progeny thereof (ATCC Accession No. PTA-120351). In other embodiments, the light chain variable domain comprises the HVR-L1, HVR-L2, and HVR-L3 and the heavy chain variable domain comprises the HVR-H1, HVR-H2, and HVR-H3 of a murine anti-human C1s monoclonal antibody 5C12 produced by a hybridoma cell line deposited with ATCC on May 15, 2013, or progeny thereof (ATCC Accession No. PTA-120352).

In some embodiments, antibodies specifically bind to and inhibit a biological activity of C1s or the C1s proenzyme, such as C1s binding to C1q, C1s binding to C1r, or C1s binding to C2 or C4. The biological activity may be a proteolytic enzyme activity of C1s, the conversion of the C1s proenzyme to an active protease, or proteolytic cleavage of C2 or C4. In certain embodiments, the biological activity is activation of the classical complement activation pathway, activation of antibody and complement dependent cytotoxicity, or CIF hemolysis.

All sequences in the following sixty-two paragraphs are incorporated by reference from Van Vlasselaer, U.S. Pat. No. 8,877,197, which is hereby incorporated by reference for the antibodies and related compositions that it discloses.

Disclosed herein are methods of administering a humanized monoclonal antibody that specifically binds an epitope within a region encompassing domains IV and V of complement component C1s. In some cases, the antibody inhibits binding of C1s to complement component 4 (C4) and/or does not inhibit protease activity of C1 s. In some embodiments, the method comprises administering a humanized monoclonal antibody that binds complement component C1s in a C1 complex with high avidity.

Disclosed herein are methods of administering an anti-C1s antibody with one or more of the complementarity determining regions (CDRs) of an antibody light chain variable region comprising amino acid sequence SEQ ID NO:57 and/or one or more of the CDRs of an antibody heavy chain variable region comprising amino acid sequence SEQ ID NO:58. The anti-C1s antibody may bind a human or rat complement C1s protein. In some embodiments, an anti-C1s antibody inhibits cleavage of at least one substrate cleaved by complement C1s protein.

In certain embodiments, the antibody comprises: a) a complementarity determining region (CDR) having an amino acid sequence selected from SEQ ID NO:51, SEQ ID NO:52, SEQ ID NO:53, SEQ ID NO:54, SEQ ID NO:55, and SEQ ID NO:56; and/or b) a CDR having an amino acid sequence selected from SEQ ID NO:62, SEQ ID NO:63, SEQ ID NO:53, SEQ ID NO:64, SEQ ID NO:65: and SEQ ID NO:66.

The antibody may comprise a CDR-L1 having amino acid sequence SEQ ID NO:51, a CDR-L2 having amino acid sequence SEQ ID NO:52, a CDR-L3 having amino acid sequence SEQ ID NO:53, a CDR-H1 having amino acid sequence SEQ ID NO:54, a CDR-H2 having amino acid sequence SEQ ID NO:55, and a CDR-H3 having amino acid sequence SEQ ID NO:56.

In other embodiments, the antibody may comprise light chain CDRs of a variable region with an amino acid sequence of SEQ ID NO:67, and/or heavy chain CDRs of a variable region with an amino acid sequence of SEQ ID NO:68.

The antibody can be a humanized antibody that specifically binds complement component C1s, wherein the antibody competes for binding the epitope with an antibody that comprises one or more of the CDRs of an antibody light chain variable region comprising amino acid sequence SEQ ID NO:57 or SEQ ID NO:67, and/or one or more of the CDRs of an antibody heavy chain variable region comprising amino acid sequence SEQ ID NO:58 or SEQ ID NO:68.

In other instances, the antibody can be a humanized antibody that specifically binds complement C1s, wherein the antibody is selected from: a) a humanized antibody that specifically binds an epitope within the complement C1s protein, wherein the antibody competes for binding the epitope with an antibody that comprises a CDR having an amino acid sequence selected from SEQ ID NO:51, SEQ ID NO:52, SEQ ID NO:53, SEQ ID NO:54, SEQ ID NO:55, and SEQ ID NO:56; and b) a humanized antibody that specifically binds an epitope within the complement C1s protein, wherein the antibody competes for binding the epitope with an antibody that comprises a CDR having an amino acid sequence selected from SEQ ID NO:62, SEQ ID NO:63, SEQ ID NO:53, SEQ ID NO:64, SEQ ID NO:65, and SEQ ID NO:66. In some cases, the antibody competes for binding the epitope with an antibody that comprises heavy and light chain CDRs comprising: a) SEQ ID NO:51, SEQ ID NO:52, SEQ ID NO:53, SEQ ID NO:69, SEQ ID NO:55, and SEQ ID NO:56; or b) SEQ ID NO:62, SEQ ID NO:63, SEQ ID NO:53, SEQ ID NO:64, SEQ ID NO:65, and SEQ ID NO:66.

The antibody may comprise a light chain region and a heavy chain region that are present in separate polypeptides. The antibody may comprise an Fc region.

Disclosed herein is an anti-C1s antibody comprising a light chain variable region of an amino acid sequence that is 90% identical to amino acid sequence SEQ ID NO:57, and a heavy chain variable region comprising an amino acid sequence that is 90% identical to amino acid sequence SEQ ID NO:58.

The anti-C1s antibody may be selected from an antigen binding fragment, Ig monomer, a Fab fragment, a $F(ab')_2$ fragment, a Fd fragment, a scFv, a scAb, a dAb, a Fv, a single domain heavy chain antibody, a single domain light chain antibody, a mono-specific antibody, a bi-specific antibody, or a multi-specific antibody.

Disclosed herein are methods of administering an antibody that competes for binding the epitope bound by antibody IPN003 (also referred to herein as "IPN-M34" or "M34" or "TNT003"), e.g., an antibody comprising a variable domain of antibody IPN003, such as antibody IPN003.

In some embodiments, the method comprises administering an antibody that specifically binds an epitope within a complement C1s protein. In some embodiments, the isolated anti-C1s antibody binds an activated C1s protein. In some embodiments, the isolated anti-C1s antibody binds an inactive form of C1s. In other instances, the isolated anti-C1s antibody binds both an activated C1s protein and an inactive form of C1s.

In some embodiments, the method comprises administering a monoclonal antibody that inhibits cleavage of C4, where the isolated monoclonal antibody does not inhibit cleavage of C2. In some embodiments, the method comprises administering a monoclonal antibody that inhibits cleavage of C2, where the isolated monoclonal antibody does not inhibit cleavage of C4. In some cases, the isolated monoclonal antibody is humanized. In some cases, the antibody inhibits a component of the classical complement pathway. In some cases, the component of the classical complement pathway that is inhibited by the antibody is C1s. The present disclosure also provides methods of treating a complement-mediated disease or disorder, by administering to an individual in need thereof an isolated monoclonal antibody that inhibits cleavage of C4, or a pharmaceutical composition comprising the isolated monoclonal antibody, where the isolated monoclonal antibody does not inhibit cleavage of C2.

In some embodiments, the method comprises administering a monoclonal antibody that inhibits cleavage of C2 or C4 by C1s, i.e., inhibits C1s-mediated proteolytic cleavage of C2 or C4. In some cases, the monoclonal antibody is humanized. In some cases, the antibody inhibits cleavage of C2 or C4 by C1s by inhibiting binding of C2 or C4 to C1s; for example, in some cases, the antibody inhibits C1s-mediated cleavage of C2 or C4 by inhibiting binding of C2 or C4 to a C2 or C4 binding site of C1s. Thus, in some cases, the antibody functions as a competitive inhibitor. The present disclosure also provides methods of treating a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin), by administering to an individual in need thereof an isolated monoclonal antibody that inhibits cleavage of C2 or C4 by C1s, i.e., inhibits C1s-mediated proteolytic cleavage of C2 or C4.

In some embodiments, the method comprises administering a monoclonal antibody that inhibits cleavage of C4 by C1s, where the antibody does not inhibit cleavage of complement component C2 by C1s; i.e., the antibody inhibits C1s-mediated cleavage of C4, but does not inhibit C1s-mediated cleavage of C2. In some cases, the monoclonal antibody is humanized. In some cases, the monoclonal antibody inhibits binding of C4 to C1s, but does not inhibit binding of C2 to C1s. In some embodiments, the method comprises treating a complement-mediated disease or disorder, by administering to an individual in need thereof an isolated monoclonal antibody that inhibits cleavage of C4 by C1s, where the antibody does not inhibit cleavage of complement component C2 by C1s; i.e., the antibody inhibits C1s-mediated cleavage of C4, but does not inhibit C1s-mediated cleavage of C2. In some embodiments of the method, the antibody is humanized.

In some embodiments, the method comprises administering a humanized monoclonal antibody that specifically binds an epitope within a region encompassing domains IV and V of C1s. For example, the humanized monoclonal antibody specifically binds an epitope within amino acids 272-422 of the amino acid sequence depicted in FIG. 1 and set forth in SEQ ID NO:70. In some cases, the humanized monoclonal antibody specifically binds an epitope within amino acids 272-422 of the amino acid sequence depicted in FIG. 1 and set forth in SEQ ID NO:70, and inhibits binding of C4 to C1s. In some embodiments, the method comprises treating a complement-mediated disease or disorder, by administering to an individual in need thereof a humanized monoclonal antibody that specifically binds an epitope within amino acids 272-422 of the amino acid sequence depicted in FIG. 1 and set forth in SEQ ID NO:70, and inhibits binding of C4 to C1s.

In some embodiments, the method comprises administering a humanized monoclonal antibody that specifically binds a conformational epitope within a region encompassing domains IV and V of C1s. For example, the humanized monoclonal antibody that specifically binds a conformational epitope within amino acids 272-422 of the amino acid sequence depicted in FIG. 1 and set forth in SEQ ID NO:70. In some cases, the humanized monoclonal antibody specifically binds a conformational epitope within amino acids 272-422 of the amino acid sequence depicted in FIG. 1 and set forth in SEQ ID NO:70, and inhibits binding of C4 to C1s. In some embodiments, the method comprises a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin), the method comprising administering to an individual in need thereof a humanized monoclonal antibody that specifically binds a conformational epitope within amino acids 272-422 of the amino acid sequence depicted in FIG. 1 and set forth in SEQ ID NO:70, and inhibits binding of C4 to C1s.

In some embodiments, the method comprises administering a monoclonal antibody that binds complement component C1s in a C1 complex. The C1 complex is composed of 6 molecules of C1q, 2 molecules of C1r, and 2 molecules of C1s. In some cases, the monoclonal antibody is humanized.

Thus, in some cases, the humanized monoclonal antibody that binds complement component C1s in a C1 complex. In some cases, the antibody binds C1s present in a C1 complex with high avidity.

In some embodiments, the anti-C1s antibody (e.g., a subject antibody that specifically binds an epitope in a complement C1s protein) comprises: a) a light chain region comprising one, two, or three VL CDRs of an IPN003 antibody; and b) a heavy chain region comprising one, two, or three VH CDRs of an IPN003 antibody; where the VH and VL CDRs are as defined by Kabat (Kabat 1991).

In other embodiments, the anti-C1s antibody (e.g., a subject antibody that specifically binds an epitope in a complement C1s protein) comprises: a) a light chain region comprising one, two, or three VL CDRs of an IPN003 antibody; and b) a heavy chain region comprising one, two, or three VH CDRs of an IPN003 antibody; where the VH and VL CDRs are as defined by Chothia (Chothia 1987).

In some embodiments, the anti-C1s antibody (e.g., a subject antibody that specifically binds an epitope in a complement C1s protein) comprises: a) a light chain region comprising one, two, or three CDRs selected from SEQ ID NO:51, SEQ ID NO:52, and SEQ ID NO:53; and b) a heavy chain region comprising one, two, or three CDRs selected from SEQ ID NO:54, SEQ ID NO:55, and SEQ ID NO:56. In some of these embodiments, the anti-C1s antibody includes a humanized VH and/or VL framework region.

```
SEQ ID NO. 51:
SSVSSSYLHWYQ;

SEQ ID NO. 52:
STSNLASGVP;

SEQ ID NO. 53:
HQYYRLPPIT;

SEQ ID NO. 54:
GFTFSNYAMSWV;

SEQ ID NO. 55:
ISSGGSHTYY;

SEQ ID NO. 56:
ARLFTGYAMDY.
```

In some embodiments, the anti-C1s antibody comprises a CDR having an amino acid sequence selected from SEQ ID NO:51, SEQ ID NO:52, SEQ ID NO:53, SEQ ID NO:54, SEQ ID NO:55, and SEQ ID NO:56.

In some embodiments, the anti-C1s antibody comprises a light chain variable region comprising amino acid sequences SEQ ID NO:51, SEQ ID NO:52, and SEQ ID NO:53.

In some embodiments, the anti-C1s antibody comprises a heavy chain variable region comprising amino acid sequences SEQ ID NO:54, SEQ ID NO:55, and SEQ ID NO:56.

In some embodiments, the anti-C1s antibody comprises a CDR-L1 having amino acid sequence SEQ ID NO:51, a CDR-L2 having amino acid sequence SEQ ID NO:52, a CDR-L3 having amino acid sequence SEQ ID NO:53, a CDR-H1 having amino acid sequence SEQ ID NO:54, a CDR-H2 having amino acid sequence SEQ ID NO:55, and a CDR-H3 having amino acid sequence SEQ ID NO:56.

In some embodiments, the anti-C1s antibody comprises a light chain variable region comprising an amino acid sequence that is 85%, 86%, 87%, 88%, 89%, 90%, 91%, 92%, 93%, 94%, 95%, 96%, 97%, 98% or 99% identical to the amino acid sequence set forth in SEQ ID NO:57.

```
SEQ ID NO. 57:
DIVMTQTTAIMSASLGERVTMTCTASSSVSSSYLHWYQQKPGSSPKLWIY
STSNLASGVPARFSGSGSGTFYSLTISSMEAEDDATYYCHQYYRLPPITF
GAGTKLELK.
```

In some embodiments, the anti-C1s antibody comprises a heavy chain variable region comprising an amino acid sequence that is 85%, 86%, 87%, 88%, 89%, 90%, 91%, 92%, 93%, 94%, 95%, 96%, 97%, 98% or 99% identical to the amino acid sequence set forth in SEQ ID NO. 58.

```
SEQ ID NO. 58:
QVKLEESGGALVKPGGSLKLSCAASGFTFSNYAMSWVRQIPEKRLEWVAT
ISSGGSHTYYLDSVKGRFTISRDNARDTLYLQMSSLRSEDTALYYCARLF
TGYAMDYWGQGTSVT.
```

In some embodiments, the anti-C1s antibody comprises a light chain variable region comprising an amino acid sequence that is 90% identical to amino acid sequence SEQ ID NO:57.

In some embodiments, the anti-C1s antibody comprises a heavy chain variable region comprising an amino acid sequence that is 90% identical to amino acid sequence SEQ ID NO:58.

In some embodiments, the anti-C1s antibody comprises a light chain variable region comprising amino acid sequence SEQ ID NO:57.

In some embodiments, the anti-C1s antibody comprises a heavy chain variable region comprising amino acid sequence SEQ ID NO:58.

In some embodiments, the anti-C1s antibody comprises a light chain variable region comprising an amino acid sequence that is 90% identical to amino acid sequence SEQ ID NO:57 and a heavy chain variable region comprising an amino acid sequence that is 90% identical to amino acid sequence SEQ ID NO:58.

In some embodiments, the anti-C1s antibody comprises a light chain variable region comprising amino acid sequence SEQ ID NO:57 and a heavy chain variable region comprising amino acid sequence SEQ ID NO:58.

In some embodiments, the anti-C1s antibody specifically binds an epitope within the complement C1s protein, wherein the antibody competes for binding the epitope with an antibody that comprises light chain CDRs of an antibody light chain variable region comprising amino acid sequence SEQ ID NO:57 and heavy chain CDRs of an antibody heavy chain variable region comprising amino acid sequence SEQ ID NO:58.

In some embodiments, the anti-C1s antibody comprises light chain CDRs of an antibody light chain variable region comprising amino acid sequence SEQ ID NO:57 and heavy chain CDRs of an antibody heavy chain variable region comprising amino acid sequence SEQ ID NO:58.

In some embodiments, the anti-C1s antibody (e.g., a subject antibody that specifically binds an epitope in a complement C1s protein) comprises: a) a light chain region comprising one, two, or three CDRs selected from SEQ ID NO:62, SEQ ID NO:63, and SEQ ID NO:53; and b) a heavy chain region comprising one, two, or three CDRs selected from SEQ ID NO:64, SEQ ID NO:65, and SEQ ID NO:66.

```
SEQ ID NO. 62:
TASSSVSSSYLH;

SEQ ID NO. 63
STSNLAS;
```

-continued

```
SEQ ID NO. 53:
HQYYRLPPIT;

SEQ ID NO. 64:
NYAMS;

SEQ ID NO. 65:
TISSGGSHTYYLDSVKG;

SEQ ID NO. 66:
LFTGYAMDY
```

In some embodiments, the anti-C1s antibody comprises a CDR having an amino acid sequence selected from SEQ ID NO:62, SEQ ID NO:63, SEQ ID NO:53, SEQ ID NO:64, SEQ ID NO:65, and SEQ ID NO:66.

In some embodiments, the anti-C1s antibody comprises a light chain variable region comprising amino acid sequences SEQ ID NO:62, SEQ ID NO:63, and SEQ ID NO:53.

In some embodiments, the anti-C1s antibody comprises a heavy chain variable region comprising amino acid sequences SEQ ID NO:64, SEQ ID NO:65, and SEQ ID NO:66.

In some embodiments, the anti-C1s antibody comprises a CDR-L1 having amino acid sequence SEQ ID NO:62, a CDR-L2 having amino acid sequence SEQ ID NO:63, a CDR-L3 having amino acid sequence SEQ ID NO:53, a CDR-H1 having amino acid sequence SEQ ID NO:64, a CDR-H2 having amino acid sequence SEQ ID NO:65, and a CDR-H3 having amino acid sequence SEQ ID NO:66.

In some embodiments, the anti-C1s antibody comprises a light chain variable region comprising an amino acid sequence that is 85%, 86%, 87%, 88%, 89%, 90%, 91%, 92%, 93%, 94%, 95%, 96%, 97%, 98% or 99% identical to the amino acid sequence set forth in SEQ ID NO:67.

```
SEQ ID NO. 67:
QIVLTQSPAIMSASLGERVTMTCTASSSVSSSYLHWYQQKPGSSPKLWI
YSTSNLASGVPARFSGSGSGTFYSLTISSMEAEDDATYYCHQYYRLPPI
TFGAGTKLELK.
```

In some embodiments, the anti-C1s antibody comprises a heavy chain variable region comprising an amino acid sequence that is 85%, 86%, 87%, 88%, 89%, 90%, 91%, 92%, 93%, 94%, 95%, 96%, 97%, 98% or 99% identical to the amino acid sequence set forth in SEQ ID NO:68.

```
SEQ ID NO. 68:
EVMLVESGGALVKPGGSLKLSCAASGFTFSNYAMSWVRQIPEKRLEWVA
TISSGGSHTYYLDSVKGRFTISRDNARDTLYLQMSSLRSEDTALYYCAR
LFTGYAMDYWGQGTSVTVSS.
```

In some embodiments, the anti-C1s antibody comprises a light chain variable region comprising an amino acid sequence that is 90% identical to amino acid sequence SEQ ID NO:67.

In some embodiments, the anti-C1s antibody comprises a heavy chain variable region comprising an amino acid sequence that is 90% identical to amino acid sequence SEQ ID NO:68.

In some embodiments, the anti-C1s antibody comprises a light chain variable region comprising amino acid sequence SEQ ID NO:67.

In some embodiments, the anti-C1s antibody comprises a heavy chain variable region comprising amino acid sequence SEQ ID NO:68.

In some embodiments, the anti-C1s antibody comprises a light chain variable region comprising an amino acid sequence that is 90% identical to amino acid sequence SEQ ID NO:67 and a heavy chain variable region comprising an amino acid sequence that is 90% identical to amino acid sequence SEQ ID NO:68.

In some embodiments, the anti-C1s antibody comprises a light chain variable region comprising an amino acid sequence that is 95% identical to amino acid sequence SEQ ID NO:67 and a heavy chain variable region comprising an amino acid sequence that is 95% identical to amino acid sequence SEQ ID NO:68.

In some embodiments, the anti-C1s antibody comprises a light chain variable region comprising amino acid sequence SEQ ID NO:67 and a heavy chain variable region comprising amino acid sequence SEQ ID NO:68.

In some embodiments, the anti-C1s antibody specifically binds an epitope within the complement C1s protein, wherein the antibody competes for binding the epitope with an antibody that comprises light chain CDRs of an antibody light chain variable region comprising amino acid sequence SEQ ID NO:67 and heavy chain CDRs of an antibody heavy chain variable region comprising amino acid sequence SEQ ID NO:68.

In some embodiments, the anti-C1s antibody comprises light chain CDRs of an antibody light chain variable region comprising amino acid sequence SEQ ID NO:67 and heavy chain CDRs of an antibody heavy chain variable region comprising amino acid sequence SEQ ID NO:68.

In some embodiments, the anti-C1s antibody comprises a light chain variable region comprising an amino acid sequence that is 85%, 86%, 87%, 88%, 89%, 90%, 91%, 92%, 93%, 94%, 95%, 96%, 97%, 98% or 99% identical to the amino acid sequence set forth in SEQ ID NO:67.

In some embodiments, the anti-C1s antibody comprises a heavy chain variable region comprising an amino acid sequence that is 85%, 86%, 87%, 88%, 89%, 90%, 91%, 92%, 93%, 94%, 95%, 96%, 97%, 98% or 99% identical to the amino acid sequence set forth in SEQ ID NO:68.

An anti-C1s antibody can comprise a heavy chain variable region comprising an amino acid sequence that is 85%, 86%, 87%, 88%, 89%, 90%, 91%, 92%, 93%, 94%, 95%, 96%, 97%, 98%, 99%, or 100% identical to the amino acid sequence set forth in SEQ ID NO:79 and depicted in FIG. 2 (VH variant 1).

An anti-C1s antibody can comprise a heavy chain variable region comprising an amino acid sequence that is 85%, 86%, 87%, 88%, 89%, 90%, 91%, 92%, 93%, 94%, 95%, 96%, 97%, 98%, 99%, or 100% identical to the amino acid sequence set forth in SEQ ID NO:80 and depicted in FIG. 3 (VH variant 2).

An anti-C1s antibody can comprise a heavy chain variable region comprising an amino acid sequence that is 85%, 86%, 87%, 88%, 89%, 90%, 91%, 92%, 93%, 94%, 95%, 96%, 97%, 98%, 99%, or 100% identical to the amino acid sequence set forth in SEQ ID NO:81 and depicted in FIG. 4 (VH variant 3).

An anti-C1s antibody can comprise a heavy chain variable region comprising an amino acid sequence that is 85%, 86%, 87%, 88%, 89%, 90%, 91%, 92%, 93%, 94%, 95%, 96%, 97%, 98%, 99%, or 100% identical to the amino acid sequence set forth in SEQ ID NO:82 and depicted in FIG. 5 (VH variant 4).

Figure 6A:
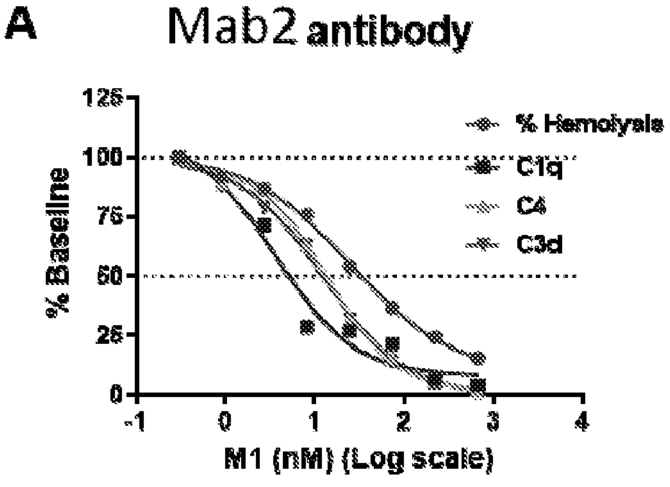
FIGS. 6A-6B show dose-dependent inhibition of serum hemolysis and complement deposition with anti-C1q antibody (Mab2) and FabA in samples from CAD patients.
Figure 6B:
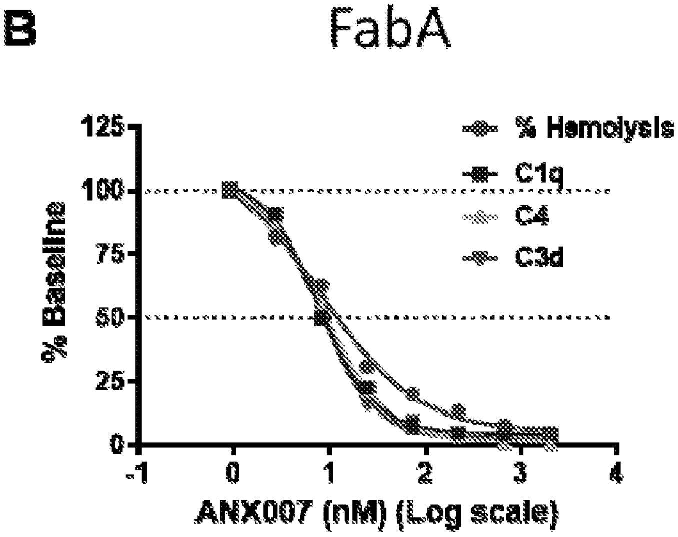

An anti-C1s antibody can comprise a light chain variable region comprising an amino acid sequence that is 85%, 86%, 87%, 88%, 89%, 90%, 91%, 92%, 93%, 94%, 95%, 96%, 97%, 98%, 99%, or 100% identical to the amino acid sequence set forth in SEQ ID NO:83 and depicted in FIG. 6 (VK variant 1).

An anti-C1s antibody can comprise a light chain variable region comprising an amino acid sequence that is 85%, 86%, 87%, 88%, 89%, 90%, 91%, 92%, 93%, 94%, 95%, 96%, 97%, 98%, 99%, or 100% identical to the amino acid sequence set forth in SEQ ID NO:84 and depicted in FIG. 7 (VK variant 2).

Figure 8:
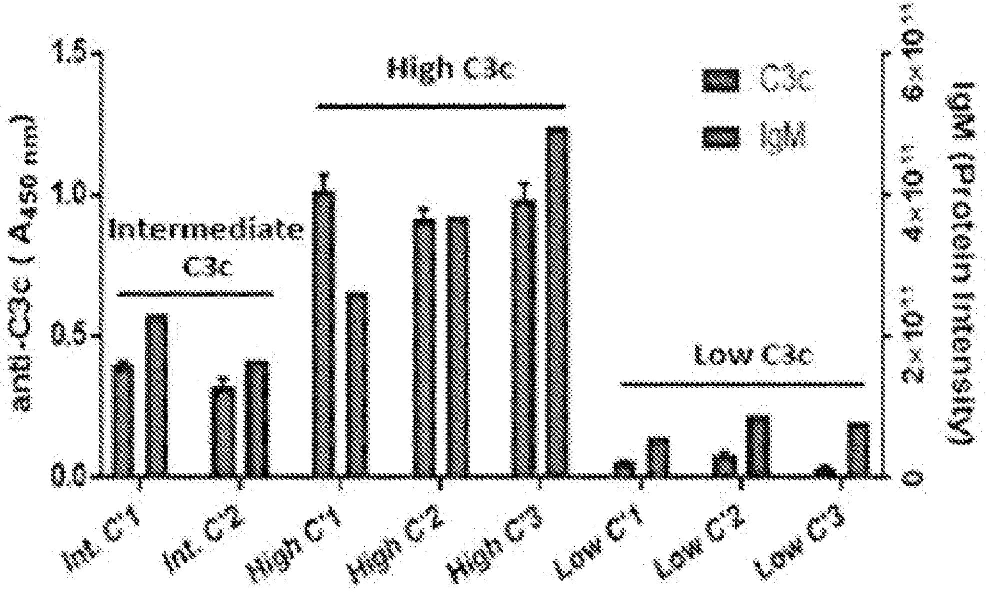
FIG. 8 shows that complement activation by PF4/heparin correlates with plasma/serum IgM levels.

An anti-C1s antibody can comprise a light chain variable region comprising an amino acid sequence that is 85%, 86%, 87%, 88%, 89%, 90%, 91%, 92%, 93%, 94%, 95%, 96%, 97%, 98%, 99%, or 100% identical to the amino acid sequence set forth in SEQ ID NO:85 and depicted in FIG. 8 (VK variant 3).

Figure 9:
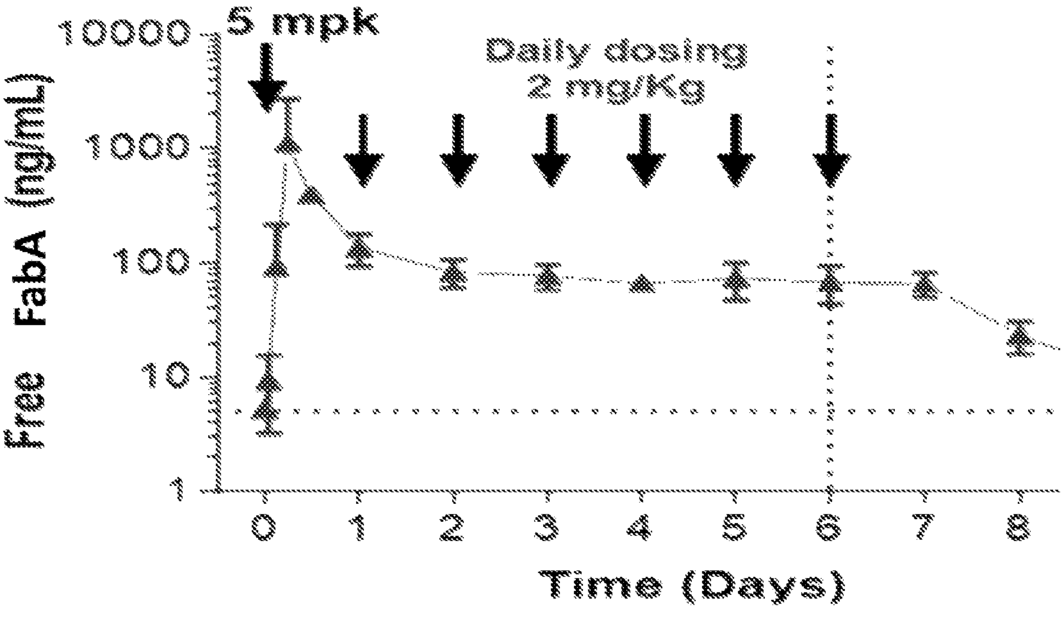
FIG. 9 shows serum Free-FabA levels in animals dosed with 5+1 mg/kg and 5+2 mg/kg. Lower limit of quantification=5 ng/mL.

An anti-C1s antibody can comprise a heavy chain variable region comprising 1, 2, 3, 4, 5, 6, 7, 8, 9, 10, 11, or 12 of the framework (FR) amino acid substitutions, relative to the IPN003 parental antibody FR amino acid sequences, depicted in Table 3 (FIG. 9).

Definitions

As used herein the specification, "a" or "an" may mean one or more. As used herein in the claim(s), when used in conjunction with the word "comprising", the words "a" or "an" may mean one or more than one. For example, reference to an "antibody" is a reference from one to many antibodies. As used herein "another" may mean at least a second or more.

As used herein, administration "conjointly" with another compound or composition includes simultaneous administration and/or administration at different times. Administration in conjunction also encompasses administration as a co-formulation or administration as separate compositions, including at different dosing frequencies or intervals, and using the same route of administration or different routes of administration.

"A complement-mediated blood disorder" is a disorder of the vascular compartment or highly vascularized tissues caused by circulating C1q and complement activation. Complement activation may be initiated through the classical pathway. The classical pathway may be activated by the binding of the complement protein C1q directly with patches of surface-bound antibodies or surface proteins.

The term "immunoglobulin" (Ig) is used interchangeably with "antibody" herein. The term "antibody" herein is used in the broadest sense and specifically covers monoclonal antibodies, polyclonal antibodies, multispecific antibodies (e.g., bispecific antibodies) formed from at least two intact antibodies, antibody fragments so long as they exhibit biological activity, and antibody derivatives.

The basic 4-chain antibody unit is a heterotetrameric glycoprotein composed of two identical light (L) chains and two identical heavy (H) chains. The pairing of a VH and VL together forms a single antigen-binding site. For the structure and properties of the different classes of antibodies, see, e.g., *Basic and Clinical Immunology,* 8th Ed., Daniel P. Stites, Abba I. Terr and Tristram G. Parslow (eds.), Appleton & Lange, Norwalk, C T, 1994, page 71 and Chapter 6.

The L chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ") and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three dimensional configurations of different classes of immunoglobulins are well known and described generally in, for example, Abbas et al., Cellular and Molecular Immunology, $4^{th}$ ed. (W.B. Saunders Co., 2000).

"Full-length antibodies" are usually heterotetrameric glycoproteins of about 150,000 daltons, comprising two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

An "isolated" molecule or cell is a molecule or a cell that is identified and separated from at least one contaminant molecule or cell with which it is ordinarily associated in the environment in which it was produced. Preferably, the isolated molecule or cell is free of association with all components associated with the production environment. The isolated molecule or cell is in a form other than in the form or setting in which it is found in nature. Isolated molecules therefore are distinguished from molecules existing naturally in cells; isolated cells are distinguished from cells existing naturally in tissues, organs, or individuals. In some embodiments, the isolated molecule is an anti-C1s, anti-C1q, or anti-C1r antibody of the present disclosure. In other embodiments, the isolated cell is a host cell or hybridoma cell producing an anti-C1s, anti-C1q, or anti-C1r antibody of the present disclosure.

An "isolated" antibody is one that has been identified, separated and/or recovered from a component of its production environment (e.g., naturally or recombinantly). Preferably, the isolated polypeptide is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In certain preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. An isolated antibody includes the antibody in situ within recombinant T-cells since at least one component of the antibody's natural environment will not be present. Ordinarily, however, an isolated polypeptide or antibody will be prepared by a process including at least one purification step.

The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, MD (1991)). The constant domains are not involved directly in the binding of antibody to an antigen, but exhibit various effector functions, such as participation of the antibody in antibody-dependent-cellular toxicity.

As used herein, the term "CDR" or "complementarity determining region" is intended to mean the non-contiguous antigen binding sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991) (also referred to herein as Kabat 1991); by Chothia et al., J. Mol. Biol. 196:901-917 (1987) (also referred to herein as Chothia 1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein.

As used herein, the terms "CDR-L1", "CDR-L2", and "CDR-L3" refer, respectively, to the first, second, and third CDRs in a light chain variable region. As used herein, the terms "CDR-H1", "CDR-H2", and "CDR-H3" refer, respectively, to the first, second, and third CDRs in a heavy chain variable region. As used herein, the terms "CDR-1", "CDR-2", and "CDR-3" refer, respectively, to the first, second and third CDRs of either chain's variable region.

The term "monoclonal antibody" as used herein refers to an antibody obtained from a population of substantially homogeneous antibodies, i.e., the individual antibodies of the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, monoclonal antibodies are advantageous since they are typically synthesized by hybridoma culture, uncontaminated by other immunoglobulins. The modifier "monoclonal" indicates the character of the antibody as being obtained as a substantially homogeneous population of antibodies, and is not to be construed as requiring production of the antibody by any particular method. For example, the monoclonal antibodies to be used in accordance with the present disclosure may be made by a variety of techniques, including, for example, the hybridoma method (e.g., Kohler and Milstein, *Nature,* 256:495-97 (1975); Hongo et al., *Hybridoma,* 14 (3):253-260 (1995), Harlow et al., *Antibodies: A Laboratory Manual*, (Cold Spring Harbor Laboratory Press, 2d ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352:624-628 (1991); Marks et al., *J. Mol. Biol.* 222:581-597 (1992); Sidhu et al., *J. Mol. Biol.* 338(2): 299-310 (2004); Lee et al., *J. Mol. Biol.* 340(5):1073-1093 (2004); Fellouse, *Proc. Nat'l Acad. Sci. USA* 101(34): 12467-472 (2004); and Lee et al., *J. Immunol. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Nat'l Acad. Sci. USA* 90:2551 (1993); Jakobovits et al., *Nature* 362:255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10:779-783 (1992); Lonberg et al., *Nature* 368:856-859 (1994); Morrison, *Nature* 368:812-813 (1994); Fishwild et al., *Nature Biotechnol.* 14:845-851 (1996); Neuberger, *Nature Biotechnol.* 14:826 (1996); and Lonberg and Huszar, *Intern. Rev. Immunol.* 13:65-93 (1995).

The terms "full-length antibody," "intact antibody" and "whole antibody" are used interchangeably to refer to an antibody in its substantially intact form, as opposed to an antibody fragment or antibody derivative. Specifically, whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" or "antigen-binding fragment" or "functional fragments" of antibodies comprises a portion of an intact antibody, preferably the antigen binding and/or the variable region of the intact antibody or the F region of an antibody which retains or has modified FcR binding capability. Examples of antibody fragments include Fab, Fab', $F(ab')_2$ and Fv fragments; diabodies; and linear antibodies (see U.S. Pat. No. 5,641,870, Example 2; Zapata et al., *Protein Eng.* 8(10):1057-1062 (1995)). Additional examples of antibody fragments include antibody derivatives such as single-chain antibody molecules, monovalent antibodies and multispecific antibodies formed from antibody fragments An "antibody derivative" is any construct that comprises the antigen-binding region of an antibody. Examples of antibody derivatives include single-chain antibody molecules, monovalent antibodies and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large $F(ab')_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue (s) of the constant domains bear a free thiol group. $F(ab')_2$ antibody fragments originally were produced as pairs of Fab' fragments with hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. (See, e.g., M. Daeron, *Annu. Rev. Immunol.* 15:203-234 (1997)). FcRs are reviewed in Ravetch and Kinet, *Annu. Rev. Immunol.* 9:457-92 (1991); Capel et al., *Immunomethods* 4:25-34 (1994); and de Haas et al., *J. Lab. Clin. Med.* 126: 330-41 (1995). Other FcRs, including those to be identified in the future, are encompassed by the term "FcR" herein. FcRs can also increase the serum half-life of antibodies.

Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants with improved or diminished binding to FcRs. See also, e.g., Shields et al., *J. Biol. Chem.* 9(2):6591-6604 (2001).

"Fv" is the minimum antibody fragment, which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain.

Preferably, the sFv polypeptide further comprises a polypeptide linker between the VH and VL domains which enables the sFv to form the desired structure for antigen binding. For a review of the sFv, see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing sFv fragments (see preceding paragraph) with short linkers (about 5-10) residues) between the VH and VL domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the VH and $V_L$ domains of the two antibodies are present on different polypeptide chains. Diabodies are described in greater detail in, for example, EP 404,097; WO 1993/011161; WO/2009/121948; WO/2014/191493; Hollinger et al., *Proc. Nat'l Acad. Sci. USA* 90:6444-48 (1993).

As used herein, a "chimeric antibody" refers to an antibody (immunoglobulin) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Nat'l Acad. Sci. USA,* 81:6851-55 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is a subset of "chimeric antibodies."

"Humanized" forms of non-human (e.g., murine) antibodies are chimeric antibodies that contain minimal sequence derived from non-human immunoglobulin. In some embodiments, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, and the like. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227:381 (1991); Marks et al., *J. Mol. Biol.,* 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.,* 147(1):86-95 (1991). See also van Dijk and van de Winkel, *Curr. Opin. Pharmacol.* 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Nat'l Acad. Sci. USA,* 103:3557-3562 (2006) regarding human antibodies generated via a human B-cell hybridoma technology.

The term "hypervariable region," "HVR," or "HV," when used herein refers to the regions of an antibody-variable domain that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu in *Methods in Molecular Biology* 248:1-25 (Lo, ed., Human Press, Totowa, N J, 2003)). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of HVR delineations are in use and are encompassed herein. The HVRs that are Kabat complementarity-determining regions (CDRs) are based on sequence variability and are the most commonly used (Kabat et al., supra). Chothia refers instead to the location of the structural loops (Chothia and Lesk *J. Mol. Biol.* 196:901-917 (1987)). The AbM HVRs represent a compromise between the Kabat CDRs and Chothia structural loops, and are used by Oxford Molecular's AbM antibody-modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

The phrase "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g., residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see United States Patent Publication No. 2010-280227).

An "acceptor human framework" as used herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or fewer, 9 or fewer, 8 or fewer, 7 or fewer, 6 or fewer, 5 or fewer, 4 or fewer, 3 or fewer, or 2 or fewer. Where pre-existing amino acid changes are present in a VH, preferable those changes occur at only three, two, or one of positions 71H, 73H and 78H; for instance, the amino acid residues at those positions may by 71A, 73T and/or 78A. In some embodiments, the VL acceptor human framework is identical in sequence to the VL human immunoglobulin framework sequence or human consensus framework sequence.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* 5th Ed. Public Health Service, National Institutes of Health, Bethesda, MD (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra.

An "amino-acid modification" at a specified position refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In some embodiments, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH- and VL-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically recognizes" or "specifically binds" refers to measurable and reproducible interactions such as attraction or binding between a target and an antibody that is determinative of the presence of the target in the presence of a heterogeneous population of molecules including biological molecules. For example, an antibody that specifically or preferentially binds to a target or an epitope is an antibody that binds this target or epitope with greater affinity, avidity, more readily, and/or with greater duration than it binds to other targets or other epitopes of the target. It is also understood that, for example, an antibody (or a moiety) that specifically or preferentially binds to a first target may or may not specifically or preferentially bind to a second target. As such, "specific binding" or "preferential binding" does not necessarily require (although it can include) exclusive binding. An antibody that specifically binds to a target may have an association constant of at least about $10^3$ $M^{-1}$ or $10^4$ $M^{-1}$, sometimes about $10^5$ $M^{-1}$ or $10^6$ $M^{-1}$, in other instances about $10^6$ $M^{-1}$ or $10^7$ $M^{-1}$, about $10^8$ $M^{-1}$ to $10^9$ $M^{-1}$, or about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

- phenylalanine, tyrosine and tryptophan (amino acids having aromatic side chains);
- lysine, arginine and histidine (amino acids having basic side chains);
- aspartate and glutamate (amino acids having acidic side chains);
- asparagine and glutamine (amino acids having amide side chains); and
- cysteine and methionine (amino acids having sulphur-containing side chains).

Degrees of identity and similarity can be readily calculated. (See e.g., Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991)

As used herein, an "interaction" between a complement protein and a second protein encompasses, without limitation, protein-protein interaction, a physical interaction, a chemical interaction, binding, covalent binding, and ionic binding. As used herein, an antibody "inhibits interaction" between two proteins when the antibody disrupts, reduces, or completely eliminates an interaction between the two proteins. An antibody of the present disclosure, or fragment thereof, "inhibits interaction" between two proteins when the antibody or fragment thereof binds to one of the two proteins.

A "blocking" antibody, an "antagonist" antibody, an "inhibitory" antibody, or a "neutralizing" antibody is an antibody that inhibits or reduces one or more biological activities of the antigen it binds, such as interactions with one or more proteins. In some embodiments, blocking antibodies, antagonist antibodies, inhibitory antibodies, or "neutralizing" antibodies substantially or completely inhibit one or more biological activities or interactions of the antigen.

The term "inhibitor" refers to a compound having the ability to inhibit a biological function of a target biomolecule, for example, an mRNA or a protein, whether by decreasing the activity or expression of the target biomolecule. An inhibitor may be an antibody, a small molecule, or a nucleic acid molecule. The term "antagonist" refers to a compound that binds to a receptor, and blocks or dampens the receptor's biological response. The term "inhibitor" may also refer to an "antagonist."

Antibody "effector functions" refer to those biological activities attributable to the Fc region (a native sequence Fc region or amino acid sequence variant Fc region) of an antibody, and vary with the antibody isotype.

As used herein, the term "affinity" refers to the equilibrium constant for the reversible binding of two agents (e.g., an antibody and an antigen) and is expressed as a dissociation constant (KD). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1,000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. For example, a subject anti-C1s antibody binds specifically to an epitope within a complement C1s protein. "Specific binding" refers to binding with an affinity of at least about $10^{-7}$ M or greater, e.g., $5\times10^{-7}$ M, $10^{-8}$ M, $5\times10^{-8}$ M, and greater. "Non-specific binding" refers to binding with an affinity of less than about $10^{-7}$ M, e.g., binding with an affinity of $10^{-6}$ M, $10^{-5}$ M, $10^{-4}$ M, etc.

The term "$k_{on}$", as used herein, is intended to refer to the rate constant for association of an antibody to an antigen.

The term "$k_{off}$", as used herein, is intended to refer to the rate constant for dissociation of an antibody from the antibody/antigen complex.

The term "$K_D$", as used herein, is intended to refer to the equilibrium dissociation constant of an antibody-antigen interaction.

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full length of the sequences being compared.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like. The term "biological sample" also includes solid tissue samples, tissue culture samples, and cellular samples.

"Blood space", as the term is used herein, refers to the contents of a subject's cardiovascular system, including serum, platelets, endothelial cells, blood cells and other hematopoietic cells, and other materials that naturally flow through a subject's circulatory system. Targeting the blood space may have an effect on a highly vascularized tissue, e.g., the kidney, alveoli, capillary bed, or glomerulus.

An "isolated" nucleic acid molecule is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acids encoding any polypeptides and antibodies herein that exist naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors useful in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)$NR_2$ ("amidate"), P(O)R, P(O)OR', CO, or $CH_2$ ("formacetal"), in which each R or R' is independently H or substituted or unsubstituted alkyl (1-20 C) optionally containing an ether (—O—) linkage, aryl, alkenyl, cycloalkyl, cycloalkenyl or aralkyl. Not all linkages in a polynucleotide need be identical. The preceding description applies to all polynucleotides referred to herein, including RNA and DNA.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this disclosure.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "preventing" is art-recognized, and when used in relation to a condition, such as a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin), is well understood in the art, and includes administration of a composition which reduces the frequency or severity, or delays the onset, of one or more symptoms of the medical condition in a subject relative to a subject who does not receive the composition. Thus, the prevention of a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin) includes, for example, increasing the platelet count in a population of patients receiving a therapy relative to a control population that did not receive the therapy, e.g., by a statistically and/or clinically significant amount. Similarly, the prevention of a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin) includes reducing the likelihood that a patient receiving a therapy will develop a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin) or related symptoms, relative to a patient who does not receive the therapy.

The term "subject" as used herein refers to a living mammal and may be interchangeably used with the term "patient". Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. The term does not denote a particular age or gender.

As used herein, the term "treating" or "treatment" includes reducing, arresting, or reversing the symptoms, clinical signs, or underlying pathology of a condition to stabilize or improve a subject's condition or to reduce the likelihood that the subject's condition will worsen as much as if the subject did not receive the treatment.

The term "therapeutically effective amount" of a compound with respect to the subject method of treatment refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment. A therapeutically effective amount herein may vary according to factors such as the disease state, age, sex, and weight of the patient, and the ability of the antibody to elicit a desired response in the individual.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

"Chronic" administration refers to administration of the medicament(s) in a continuous as opposed to acute mode, so as to maintain the initial therapeutic effect (activity) for an extended period of time. "Intermittent" administration refers to treatment that is not administered consecutively without interruption, but rather is cyclic/periodic in nature.

As used herein, administration "conjointly" with another compound or composition includes simultaneous administration and/or administration at different times. Conjoint administration also encompasses administration as a co-formulation or administration as separate compositions, including at different dosing frequencies or intervals, and using the same route of administration or different routes of administration.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

Nucleic Acids, Vectors and Host Cells

Antibodies suitable for use in the methods of the present disclosure may be produced using recombinant methods and compositions, e.g., as described in U.S. Pat. No. 4,816,567. In some embodiments, isolated nucleic acids having a nucleotide sequence encoding any of the antibodies of the present disclosure are provided. Such nucleic acids may encode an amino acid sequence containing the $V_L/C_L$ and/or an amino acid sequence containing the $V_H/C_H1$ of the anti-C1q, anti-C1r or anti-C1s antibody. In some embodiments, one or more vectors (e.g., expression vectors) containing such nucleic acids are provided. A host cell containing such nucleic acid may also be provided. The host cell may contain (e.g., has been transduced with): (1) a vector containing a nucleic acid that encodes an amino acid sequence containing the $V_L/C_L$ of the antibody and an amino acid sequence containing the $V_H/C_H1$ of the antibody, or (2) a first vector containing a nucleic acid that encodes an amino acid sequence containing the $V_L/C_L$ of the antibody and a second vector containing a nucleic acid that encodes an amino acid sequence containing the $V_H/C_H1$ of the antibody. In some embodiments, the host cell is eukaryotic, e.g., a Chinese Hamster Ovary (CHO) cell or lymphoid cell (e.g., Y0, NS0, Sp20 cell). In some embodiments, the host cell is a bacterium such as *E. coli*.

Methods of making an anti-C1q, anti-C1r or anti-C1s antibody are disclosed herein. The method includes culturing a host cell of the present disclosure containing a nucleic acid encoding the anti-C1q, anti-C1r or anti-C1s antibody, under conditions suitable for expression of the antibody. In some embodiments, the antibody is subsequently recovered from the host cell (or host cell culture medium).

For recombinant production of a humanized anti-C1q, anti-C1r or anti-C1s antibody of the present disclosure, a nucleic acid encoding the antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

In certain embodiments, the present disclosure provides anti-C1q antibody Fab fragments, anti-C1s antibody Fab fragments, and anti-C1r antibody Fab fragments that bind to C1q, C1s, and C1r proteins, respectively. High affinity Fab fragments of these antibodies are suitable to selectively inhibit complement activation within the blood space. High affinity Fab fragments of these antibodies are suitable for administration, e.g., subcutaneous, intramuscular and intravascular administration.

Suitable vectors containing a nucleic acid sequence encoding any of the antibodies of the present disclosure, or fragments thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mpl8, mpl9, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

The vectors containing the nucleic acids of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell. In some embodiments, the vector contains a nucleic acid containing one or more amino acid sequences encoding an anti-C1q, anti-C1r or anti-C1s antibody of the present disclosure.

Suitable host cells for cloning or expression of antibody-encoding vectors include prokaryotic or eukaryotic cells. For example, an anti-C1q, anti-C1r or anti-C1s antibody of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523; and Charlton, *Methods in Molecular Biology*, Vol. 248 (B. K. C. Lo, ed., Humana Press, Totowa, N J, 2003), pp. 245-254, describing expression of antibody fragments in *E. coli*). In other embodiments, the antibody of the present disclosure may be produced in eukaryotic cells, e.g., a Chinese Hamster Ovary (CHO) cell or lymphoid cell (e.g., Y0, NS0, Sp20 cell) (e.g., U.S. patent application Ser. No. 14/269,950, U.S. Pat. No. 8,981,071, *Eur J Biochem.* 1991 Jan. 1; 195(1):235-42). After expression, the antibody may be isolated from the bacterial cell paste in a soluble fraction and can be further purified.

Antibody Screening

Candidate antibodies can be screened for the ability to modulate complement activation. Such screening may be performed using an in vitro model, a genetically altered cell or animal, or purified protein. A wide variety of assays may be used for this purpose, such as an in vitro culture system.

Candidate antibodies may also be identified using computer-based modeling, by binding assays, and the like. Various in vitro models may be used to determine whether an antibody binds to, or otherwise affects complement activity. Such candidate antibodies may be tested by contacting plasma from a healthy donor and determine complement activation (e.g., by the antigen C3c capture ELISA). Such antibodies may be further tested in an in vivo model for an effect on a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or antiphospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin).

Generally, a plurality of assay mixtures are run in parallel with different antibody concentrations to obtain a differential response to the various concentrations. Typically one of these concentrations serves as a negative control, i.e., at zero concentration or below the level of detection.

Pharmaceutical Compositions and Administration

A complement inhibitor (e.g. an antibody) of the present disclosure may be administered in the form of pharmaceutical compositions.

Therapeutic formulations of an inhibitor (e.g., an antibody, antibody fragments and/or antibody derivatives) of the disclosure may be prepared for storage by mixing the inhibitor having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Lipofections or liposomes may also be used to deliver an antibody or antibody fragment, or antibody derivative into a cell, wherein the epitope or smallest fragment which specifically binds to the binding domain of the target protein is preferred.

The inhibitor may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for administration may be sterile. This is readily accomplished by filtration through sterile filtration membranes.

Sustained-release preparations may be prepared. Suitable examples of sustained-release preparations include semipermeable matrices of solid hydrophobic polymers containing the inhibitor, which matrices are in the form of shaped articles, e.g., films, or microcapsules.

Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The antibodies, antibody fragments and/or antibody derivatives and compositions of the present disclosure are typically administered by various routes, including, but not limited to, topical, parenteral, subcutaneous, intraperitoneal, intrapulmonary, intranasal, and intralesional administration. Parenteral routes of administration include intramuscular, intravenous, intraarterial, intraperitoneal, intrathecal, or subcutaneous administration.

Pharmaceutical compositions may also include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation may include other carriers, adjuvants, or non-toxic, nontherapeutic, nonimmunogenic stabilizers, excipients and the like. The compositions may also include additional substances to approximate physiological conditions, such as pH adjusting and buffering agents, toxicity adjusting agents, wetting agents and detergents.

The composition may also include any of a variety of stabilizing agents, such as an antioxidant for example. When the pharmaceutical composition includes a polypeptide, the polypeptide may be complexed with various well-known compounds that enhance the in vivo stability of the polypeptide, or otherwise enhance its pharmacological properties (e.g., increase the half-life of the polypeptide, reduce its toxicity, enhance other pharmacokinetic and/or pharmacodynamic characteristics, or enhance solubility or uptake). Examples of such modifications or complexing agents include sulfate, gluconate, citrate and phosphate. The polypeptides of a composition may also be complexed with molecules that enhance their in vivo attributes. Such molecules include, for example, carbohydrates, polyamines, amino acids, other peptides, ions (e.g., sodium, potassium, calcium, magnesium, manganese), and lipids. Further guidance regarding formulations that are suitable for various types of administration may be found in Remington's Pharmaceutical Sciences, Mace Publishing Company, Philadelphia, Pa., 17th ed. (1985). For a brief review of methods for drug delivery, see, Langer, Science 249:1527-1533 (1990).

Toxicity and therapeutic efficacy of the active ingredient may be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it may be expressed as the ratio LD50/ED50. Compounds that exhibit large therapeutic indices are preferred.

The data obtained from cell culture and/or animal studies and/or human clinical trials may be used in formulating a range of dosages for humans. The dosage of the active ingredient typically lines within a range of circulating concentrations that include the ED50 with low toxicity. The dosage may vary within this range depending upon the dosage form employed and the route of administration utilized.

The pharmaceutical compositions described herein may be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

Formulations suitable for parenteral administration include aqueous and non-aqueous, isotonic sterile injection solutions, which may contain antioxidants, buffers, bacteriostats, and solutes that render the formulation isotonic with the blood of the intended recipient, and aqueous and non-aqueous sterile suspensions that may include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for parenteral use are usually sterile. To the extent that a given compound must be synthesized prior to use, the resulting product is typically substantially free of any potentially toxic agents, particularly any endotoxins, which may be present during the synthesis or purification process. Compositions for parental administration are also typically substantially isotonic and made under GMP conditions.

The compositions of the disclosure may be administered using any medically appropriate procedure, e.g., intravascular (intravenous, intraarterial, intracapillary) administration, intramuscular, or subcutaneously. The composition may be administered via an auto-injector or an infusion device such as a minipump or an on-body infusor.

The effective amount of a therapeutic composition given to a particular patient may depend on a variety of factors, several of which may be different from patient to patient. A competent clinician will be able to determine an effective amount of a therapeutic agent to administer to a patient. Dosage of the agent will depend on the treatment, route of administration, the nature of the therapeutics, sensitivity of the patient to the therapeutics, etc. Utilizing LD50 animal data, and other information, a clinician may determine the maximum safe dose for an individual, depending on the route of administration. Utilizing ordinary skill, the competent clinician will be able to optimize the dosage of a particular therapeutic composition in the course of routine clinical trials. The compositions may be administered to the subject in a series of more than one administration. For therapeutic compositions, regular periodic administration will sometimes be required, or may be desirable. Therapeutic regimens will vary with the agent; for example, some agents may be taken for extended periods of time on a daily or semi-daily basis, while more selective agents may be administered for more defined time courses, e.g., one, two three or more days, one or more weeks, one or more months, etc., taken daily, semi-daily, semi-weekly, weekly, etc.

In some embodiments, the antibody is a full-length antibody. In some embodiments, the antibody is administered to the subject by intravenous injection or infusion at a dose between 10 mg/kg and 150 mg/kg. In some embodiments, the antibody is administered to the subject by intravenous injection or infusion at a dose between 10 mg/kg and 20 mg/kg, 20 mg/kg and 30 mg/kg, 30 mg/kg and 40 mg/kg, 40 mg/kg and 50 mg/kg, 50 mg/kg and 60 mg/kg, 60 mg/kg and 70 mg/kg, 70 mg/kg and 80 mg/kg, 80 mg/kg and 90 mg/kg, 90 mg/kg and 100 mg/kg, 100 mg/kg and 110 mg/kg, 110 mg/kg and 120 mg/kg, 120 mg/kg and 130 mg/kg, 130 mg/kg and 140 mg/kg, or 140 mg/kg and 150 mg/kg. In some embodiments, the antibody is administered to the subject by intravenous injection or infusion at a dose between 75 mg/kg and 100 mg/kg. The antibody may be administered, once a week, once every other week, or once a month. In some embodiments, the antibody is administered to the subject by intravenous injection or infusion at a dose of 75 mg/kg. In some embodiments, the antibody is administered to the subject by intravenous injection or infusion at a dose of 100 mg/kg. The antibody may be administered, once a week, once every other week, once every three weeks, or once a month. In some embodiments, the antibody is administered to the subject by intravenous injection or infusion at a dose of 75 mg/kg once a week. In some embodiments, the antibody is administered to the subject by intravenous injection or infusion at a dose of 75 mg/kg once every two weeks. In some embodiments, the antibody is administered to the subject by intravenous injection or infusion at a dose of 75 mg/kg once every three weeks. In some embodiments, the antibody is administered to the subject by intravenous injection or infusion at a dose of 75 mg/kg once a month. In some embodiments, the antibody is administered to the subject by intravenous injection or infusion at a dose of 100 mg/kg once a week. In some embodiments, the antibody is administered to the subject by intravenous injection or infusion at a dose of 100 mg/kg every two weeks. In some embodiments, the antibody is administered to the subject by intravenous injection or infusion at a dose of 100 mg/kg once every three weeks. In some embodiments, the antibody is administered to the subject by intravenous injection or infusion at a dose of 100 mg/kg once a month. In some embodiments, the antibody is administered to the subject by subcutaneous or intramuscular injection at a dose between 1 mg/kg and 10 mg/kg. In some embodiments, the antibody is administered to the subject by subcutaneous or intramuscular injection at a dose between 1 mg/kg and 3 mg/kg, 3 mg/kg and 5 mg/kg, 5 mg/kg and 7 mg/kg, or 7 mg/kg and 10 mg/kg. In some embodiments, the antibody is administered daily, once every other day, once a week, once every other week, or once a month.

In some embodiments, the antibody is an antibody fragment. In some embodiments, the antibody fragment is administered to the subject by intravenous injection or infusion, by intramuscular injection, or by subcutaneous injection. In some embodiments, the antibody fragment is administered at a dose between 0.1 mg/kg and 50 mg/kg. In some embodiments, the antibody fragment is administered at a dose between 0.1 mg/kg and 1 mg/kg, 1 mg/kg and 5 mg/kg, 5 mg/kg and 10 mg/kg, 10 mg/kg and 15 mg/kg, 15 mg/kg and 20 mg/kg, 20 mg/kg and 25 mg/kg, 25 mg/kg and 30 mg/kg, 30 mg/kg and 35 mg/kg, 35 mg/kg and 40 mg/kg, 40 mg/kg and 45 mg/kg, or 45 mg/kg and 50 mg/kg. In some embodiments, the antibody fragment is administered at a dose between 0.3 mg/kg and 10 mg/kg. In some embodiments, the antibody fragment is administered daily, once every other day, once a week, once every other week, or once a month. In some embodiments, the antibody fragment is administered at an initial predose that is higher than the daily, once every other day, once a week, once every other week, or once a month dose. In some embodiments, the initial predose is between 3 mg/kg and 50 mg/kg. In some embodiments, the initial predose is between 3 mg/kg and 5 mg/kg, 5 mg/kg and 10 mg/kg, 10 mg/kg and 15 mg/kg, 15 mg/kg and 20 mg/kg, 20 mg/kg and 25 mg/kg, 25 mg/kg and 30 mg/kg, 30 mg/kg and 35 mg/kg, 35 mg/kg and 40 mg/kg, 40 mg/kg and 45 mg/kg, or 45 mg/kg and 50 mg/kg. In some embodiments, the initial predose is between 3 mg/kg and 20 mg/kg. In some embodiments, the antibody fragment has a shorter half-life as compared to its corresponding full-length antibody, such as the antibody fragment is rapidly cleared, thereby sparing C1q activity outside the subject's blood space, or the antibody selectively inhibits C1q within the subject's blood space, thereby sparing C1q activity outside the subject's blood space. In some embodiments, the blood space is confined within a blood vessel, such as an artery, an arteriole, a capillary, a venule, or a vein. The blood space may comprise serum, platelets, endothelial cells, blood cells, or hematopoietic cells. In some embodiments, inhibiting C1q within the subject's blood space reduces tissue damage in a highly vascularized tissue. Examples of highly vascularized tissues are kidney, alveoli, capillary bed, or glomerulus.

Formulations may be optimized for retention and stabilization in the body, including in the blood space. In some embodiments, when the agent is administered into the blood space, it is desirable for the agent to be retained in the blood space, and not to diffuse or otherwise be distributed extravascularly (e.g., in surrounding tissues). Stabilization techniques include cross-linking, multimerizing, or linking to groups such as polyethylene glycol, polyacrylamide, neutral protein carriers, etc., in order to achieve an increase in molecular weight.

Other strategies for increasing retention include the entrapment of the agent in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e., having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers may be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject disclosure. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Kits

The present disclosure also provides a pharmaceutical pack or kit comprising one or more containers filled with one or more of the ingredients of the pharmaceutical compositions. Associated with such container(s) may be a notice in the form prescribed by a governmental agency regulating the manufacture, use or sale of pharmaceuticals or biological products, which notice reflects approval by the agency of manufacture, use or sale for human administration.

Kits of the present disclosure may include one or more containers comprising a purified anti-C1q, anti-C1r or anti-C1s antibody and instructions for use in accordance with methods known in the art. Generally, these instructions comprise a description of administration of the inhibitor to treat or diagnose a disease, according to any methods known in the art. The kit may further comprise a description of selecting an individual suitable for treatment based on identifying whether that individual has a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin).

The instructions generally include information as to dosage, dosing schedule, and route of administration for the intended treatment. The containers may be unit doses, bulk packages (e.g., multi-dose packages) or sub-unit doses. Instructions supplied in the kits of the present disclosure are typically written instructions on a label or package insert (e.g., a paper sheet included in the kit), but machine-readable instructions (e.g., instructions carried on a magnetic or optical storage disk) are also acceptable.

The label or package insert may indicate that the composition is used for treating a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin). Instructions may be provided for practicing any of the methods described herein.

The kits of this disclosure are preferably disposed in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer), auto-injector, or an infusion device such as a minipump or an on-body infusor. A kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). At least one active agent in the composition is an inhibitor of classical complement pathway. The container may further comprise a second pharmaceutically active agent.

Kits may optionally provide additional components such as buffers and interpretive information. Normally, the kit comprises a container and a label or package insert(s) on or associated with the container.

Conditions of Interest

Representative conditions of interest include a variety of blood disorders and other hematologic diseases.

The terms "blood disorder" or "hematologic disease" are used in the broadest sense and include any pathological state involving acute or chronic blood conditions. Such diseases are generally characterized by thrombosis, inflammation and hemolysis.

Various blood conditions of interest for the present methods of preventing, reducing risk of developing, or treating a blood disorder, comprising administering an antibody, antibody fragment and/or antibody derivative that binds to complement component C1q, C1r, or C1s. Such conditions include cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or anti-phospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin.

Autoimmune hemolytic anemia (or autoimmune hemolytic anaemia (AIHA)), also referred to as "immunohemolytic anemia," occurs when antibodies directed against the subject's own red blood cells (RBCs) cause them to burst (lyse), leading to insufficient plasma concentration. The lifetime of the RBCs is reduced from the normal 100-120 days to just a few days in serious cases. The intracellular components of the RBCs are released into the circulating blood and into tissues, leading to some of the characteristic symptoms of this condition. The antibodies are usually directed against high-incidence antigens and commonly act on allogenic RBCs (RBCs originating from outside the person themselves, e.g., in the case of a blood transfusion). AIHA is classified as either warm autoimmune hemolytic anemia or cold autoimmune hemolytic anemia, which includes cold agglutinin disease and paroxysmal cold hemoglobinuria. These classifications are based on the characteristics of the autoantibodies involved in the pathogenesis of the disease. Each has a different underlying cause, management, and prognosis, making classification important when treating a patient with AIHA.

Cold agglutinin disease is a type of autoimmune hemolytic anemia in which the body's immune system mistakenly attacks and destroys its own red blood cells. When affected people's blood is exposed to cold temperatures (32° to 50° F.), certain proteins that normally attack bacteria (IgM antibodies) attach themselves to red blood cells and bind them together into clumps (agglutination). This eventually causes red blood cells to be prematurely destroyed (hemolysis) leading to anemia and other associated signs and symptoms. Cold agglutinin disease can be primary (unknown cause) or secondary, due to an underlying condition such as an infection, another autoimmune disease, or certain cancers. Treatment depends on many factors including the severity of the condition, the signs and symptoms present in each person, and the underlying cause.

Signs and symptoms include e.g., pain, fatigue, Raynaud's Syndrome, livedoid skin changes, skin ulcerations, fever, pallor, icterus, urticarial dermal eruption, hemoglobinuria, hemoglobinemia, anemia, and renal disease or acute renal failure. The symptoms may occur following exposure to cold temperatures.

A subject may be identified as having CAD using an assay to detect the presence or amount (titer) of agglutinating autoantibodies that bind to the "I antigen" on red blood cells. The antibodies may be monoclonal (e.g., monoclonal IgM or IgA) or polyclonal. A subject may also be diagnosed as having CAD using one or more of a complete blood cell count (CBC), urinalysis, biochemical studies, and a Coombs test to test for hemolysis in blood. For example, biochemical studies may be used to detect elevated lactase dehydrogenase levels, elevated unconjugated bilirubin levels, low haptoglobin levels, and/or the presence of free plasma hemoglobin, all of which may be indicative of acute hemolysis. Other tests that may be used to detect CAD include detecting complement levels in the serum. For example, due to consumption during the acute phase of hemolysis, measured plasma complement levels (e.g., C2, C3, and C4) are decreased in CAD.

Warm Agglutinin Hemolytic Anemia is an autoimmune disorder characterized by the premature destruction of healthy red blood cells by autoantibodies. In most cases, the cause of warm antibody hemolytic anemia is unknown. These cases may be referred to as primary warm antibody hemolytic anemia or idiopathic warm antibody hemolytic anemia. The disorder may also occur as part of a larger disorder. Such cases are known as secondary warm antibody hemolytic anemia. Specific symptoms that occur may vary and may depend upon the rate of onset, the rate of destruction of healthy red blood cells and the presence of an underlying disorder. Some individuals, especially those with a gradual onset of anemia, may not have any obvious symptoms (asymptomatic). Affected individuals may eventually develop abnormal paleness of the skin (pallor), fatigue, difficulty breathing upon exertion, dizziness and palpitations. Yellowing of the skin and whites of the eyes (jaundice) and enlargement of the spleen (splenomegaly) are also common findings in individuals with warm antibody hemolytic anemia. Splenomegaly may cause an affected individual to have a bloated or full feeling in the abdomen. Occasionally, enlargement of the liver (hepatomegaly) may also occur in some cases. In individuals with severe cases, especially those with rapid (acute) onset, more serious complications may develop including loss of consciousness (syncope), chest pain (angina), abnormally rapid heartbeats (tachycardia), and heart failure. Some individuals have a rare form of the warm antibody hemolytic anemia caused by IgM antibodies (as opposed to the more common form caused by IgG antibodies).

Autoimmune thrombocylopenia (ITP) is generally known as an isolated low platelet count (thrombocytopenia) with normal bone marrow and the absence of other causes of thrombocytopenia. It causes a characteristic purpuric rash and an increased tendency to bleed. Two distinct clinical syndromes manifest as an acute condition in children and a chronic condition in adults. The acute form often follows an infection and has a spontaneous resolution within two months. Chronic immune thrombocytopenia persists longer than six months with a specific cause being unknown.

ITP is diagnosed by a low platelet count in a complete blood count (a common blood test). However, since the diagnosis depends on the exclusion of other causes of a low platelet count, additional investigations, such as a bone marrow biopsy, may be necessary in some cases.

In mild cases, only careful observation may be required, but very low counts or significant bleeding may prompt treatment with corticosteroids, intravenous immunoglobulin, anti-D immunoglobulin, or immunosuppressive drugs. Refractory ITP (not responsive to conventional treatment) may require splenectomy. Platelet transfusions may be used in severe bleeding together with a very low count. Sometimes the body may compensate by making abnormally large platelets.

Signs include the spontaneous formation of bruises (purpura) and petechiae (tiny bruises), especially on the extremities, bleeding from the nostrils and/or gums, and menorrhagia (excessive menstrual bleeding), any of which may occur if the platelet count is below 20,000 per μl. A very low count (<10,000 per μl) may result in the spontaneous formation of hematomas (blood masses) in the mouth or on other mucous membranes. Bleeding time from minor lacerations or abrasions is usually prolonged. Serious and possibly fatal complications due to extremely low counts (<5,000 per μl) include subarachnoid or intracerebral hemorrhage (bleeding inside the skull or brain), lower gastrointestinal bleeding or other internal bleeding. An ITP patient with an extremely low count is vulnerable to internal bleeding caused by blunt abdominal trauma, as might be experienced in a motor vehicle crash. These complications are not likely when the platelet count is above 20,000 per 1.

Paroxysmal cold hemoglobinuria (PCH), also known as Donath-Landsteiner test positive hemolytic anemia, is an autoimmune hemolytic anemia caused by intravascular destruction of erythrocytes triggered by IgG autoantibody-mediated complement activation. The typical presentation occurs in children following exposure to an infectious agent and consists of signs and symptoms such as chills, fever, malaise, abdominal pain, aching pains in the back or legs, nausea, jaundice, and dark-colored urine.

PCH is diagnosed with a special test, called the Donath-Landsteiner test, where a patient's serum is incubated at cold temperatures for 30 minutes followed by an increase to body temperature, which triggers hemolysis of erythrocytes in vitro. It is generally an acute condition that self-resolves. However, in certain cases, acute hemolytic episodes or even chronic hemolysis may occur requiring therapy with steroids, immunosuppressants, or biologic agents such as rituximab.

Antiphospholipid syndrome (APS), also referred to as Hughes syndrome, is an autoimmune, hypercoagulable state generally caused by antiphospholipid antibodies. APS provokes blood clots (thrombosis) in arteries and veins as well as pregnancy-related complications such as miscarriage, stillbirth, preterm delivery, and severe preeclampsia.

The diagnostic criteria require one clinical event, i.e., thrombosis or pregnancy complication, and two antibody blood tests spaced typically at least three months apart that confirm the presence of either lupus anticoagulant, or anti-$\beta_2$-glycoprotein-I, as $\beta_2$-glycoprotein-I antibodies are a subset of anti-cardiolipin antibodies, an anti-cardiolipin assay may be performed as a less specific proxy.

Antiphospholipid syndrome may be primary or secondary. Primary antiphospholipid syndrome occurs in the absence of any other related disease. Secondary antiphospholipid syndrome occurs with other autoimmune diseases, such as systemic lupus erythematosus (SLE). In rare cases, APS leads to rapid organ failure due to generalized thrombosis; this is termed "catastrophic antiphospholipid syndrome" (CAPS) and is associated with a high risk of death. Antiphospholipid syndrome often requires treatment with anticoagulant medication such as heparin to reduce the risk of further episodes of thrombosis and improve the prognosis of pregnancy.

Evans Syndrome is a chronic hematologic disorder typically characterized by the simultaneous or sequential association of autoimmune hemolytic anemia with immune thrombocytopenic purpura (ITP). The syndrome may manifest both in childhood or adulthood. Episodes of thrombocytopenia may precede, occur concurrently with, or follow episodes of AIHA. The severity of symptoms and the delay between episodes of AIHA and/or ITP is variable. In adult non-simultaneous cases, the delay between the episodes is on average of 4 years. ITP is often revealed by mucocutaneous hemorrhage with epistaxis, petechiae, purpura, and ecchymoses. In case of severe thrombocytopenia, hematuria, gastrointestinal and/or cerebromeningeal hemorrhage may be observed in rare cases.

Evans syndrome is an autoimmune disorder in which non-cross-reacting autoantibodies are targeted towards different antigenic determinants on red blood cells, platelets, and sometimes neutrophils; however, the exact pathophysiologic mechanism is unknown. Because of the observation of a decrease in T-helper and an increase in T-suppressor lymphocyte population, it is suggested that the cytopenia may be related to T-cell abnormalities. Evans syndrome is frequently associated with other diseases, such as systemic lupus erythematosus, antiphospholipid syndrome, autoimmune lymphoproliferative syndrome, and common variable immunodeficiency.

Diagnosis is based on a complete blood count showing anemia (hemoglobin level<12 g/dL) and thrombocytopenia (platelet count<100,000/microL), associated or not with neutropenia (neutrophil count<1500/microL). A raised lactate dehydrogenase (LDH) and/or direct bilirubin level, and a decreased haptoglobin level may indicate hemolysis. A positive direct antiglobulin test (Coombs test) confirms the presence of antibodies targeting red blood cells (RBCs) antigens. The presence of autoantibodies targeting both platelets and neutrophils may also be observed.

Differential diagnosis mainly includes micro-angiopathies (e.g., thrombotic or thrombocytopenic purpura). Most cases are sporadic. Familial cases have exceptionally been observed, mainly in the setting of an underlying primary immunodeficiency.

Immunosuppressive therapy may be combined with intravenous immunoglobulin for ITP constitutes the first-line treatment. Administration of corticosteroids (prednisone) is the mainstay of treatment, but other drugs may be prescribed for refractory cases such as rituximab, cyclosporine, azathioprine, cyclophosphamide, and danazol. Splenectomy is performed as a third-line treatment; however long-term remission is less frequent and patients show a high risk of sepsis. In severe cases, hematopoietic stem cell transplantation may be required. Evans syndrome may have alternating periods of remission and relapse of AIHA and/or ITP despite treatment, which may be associated with significant morbidity and mortality due to severe hemorrhage and infections in case of severe thrombocytopenia and neutropenia.

NeonatalAlloimmune Thrombocytopenia (NAIT), also referred to as fetal and neonatal alloimmune thrombocytopenia (FNAIT), is a blood disorder that affects fetuses and newborns, in which the platelet count is decreased (thrombocytopenia). Platelet antigens are inherited from both mother and father. FNAIT is typically caused by antibodies specific for platelet antigens inherited from the father and are absent in the mother. Fetomaternal transfusions (or fetomaternal hemorrhage) results in the recognition of these antigens by the mother's immune system as non-self, with the subsequent generation of allo-reactive antibodies which cross the placenta. NAIT is generally caused by transplacental passage of maternal platelet-specific alloantibody and rarely human leukocyte antigen (HLA) allo-antibodies (which are expressed by platelets) to fetuses whose platelets express the corresponding antigens.

Generally, the thrombocytopenia is mild and the affected neonates remain largely asymptomatic. In these cases, therapeutic interventions are not indicated. In severe thrombocytopenia, the neonates may exhibit hemorrhagic complication at or a few hours after delivery. The most serious complication is intracranial hemorrhage, leading to death in approximately 10% or neurologic sequelae in 20% of cases.

About 80% of cases of NAIT are caused by antibodies against platelet antigen HPA-la, 15% by anti-HPA-5b, and 5% by other antibodies (e.g. HPA-1b, HPA-15, HPA-3 and HPA-9b). HPA-la is present in 98% of the population of the United States, suggesting that approximately 2% of women who are HPA-la negative may be at risk for FNAIT during pregnancy.

Unlike hemolytic disease of the fetus and newborn (HDFN), NAIT occurs during the first pregnancy in up to 50% of cases, and the affected fetuses may develop severe thrombocytopenia (<50,000/μL) very early during pregnancy (as early as 20 weeks gestation, consistent with the development of platelet antigens, and the majority of the time in utero). Usually, the thrombocytopenia increases as gestation progresses. During the first pregnancy, NAIT is often not detected until birth when the newborn presents with classic symptoms of thrombocytopenia including petechiae, bruising or intracranial hemorrhage. In utero intracranial hemorrhage occurs in about 10% to 30% of affected cases. NAIT is thought to be the underlying cause in the majority of cases of intracranial hemorrhage due to thrombocytopenia. The risk of hemorrhage is inversely related to the platelet count with the greatest risk when the platelet count is below 100,000/μL.

The recurrence of NAIT has been estimated to be more than 80% in subsequent pregnancies with incompatible fetuses (i.e., subsequent pregnancies which also carry the target platelet antigen). Subsequent cases of NAIT may be equivalent or more severe. The fetal response to FNAIT is variable and may include compensatory extra medullary hematopoiesis. Rarely, fetal hydrops may develop. Fetal anemia (in absence of red cell incompatibility) may also occur.

Methods of Treatment

By administering agents that inhibit complement activation, deposition of complement on blood cells will be prevented. Such agents include an anti-C1q, anti-C1r, or anti-C1s antibody inhibitor. Other agents may include inhibitors that upregulate expression of native complement, or agents that down-regulate C1q, C1r or C1s synthesis in platelets or blood cells (e.g., red blood cells, monocytes, neutrophils), agents that block complement activation, agents that block the signal for complement activation, and the like.

In some aspects, methods of preventing, reducing risk of developing, or treating a blood disorder are disclosed. Such methods include administering to a subject a C1q inhibitor. Numerous embodiments are further provided that can be applied to any aspect of the present invention described herein. For example, in some embodiments, the C1q inhibitor is an antibody, an aptamer, an antisense nucleic acid or a gene editing agent. In some embodiments, the inhibitor is an anti-C1q antibody. The anti-C1q antibody may inhibit the interaction between C1q and an autoantibody or between C1q and C1r, or between C1q and C1s, or may promote clearance of C1q from circulation or a tissue. In some embodiments, the anti-C1q antibody has a dissociation constant ($K_D$) that ranges from 100 nM to 0.005 nM or less than 0.005 nM. In some embodiments, the anti-C1q antibody binds C1q with a binding stoichiometry that ranges from 20:1 to 1.0:1 or less than 1.0:1, a binding stoichiometry that ranges from 6:1 to 1.0:1 or less than 1.0:1, or a binding stoichiometry that ranges from 2.5:1 to 1.0:1 or less than 1.0:1.

The methods inhibit a biological activity of C1q, C1r, or C1s. For example, (1) C1q binding to an autoantibody, (2) C1q binding to C1r, (3) C1q binding to C1s, (4) C1q binding to phosphatidylserine, (5) C1q binding to pentraxin-3, (6) C1q binding to C-reactive protein (CRP), (7) C1q binding to globular C1q receptor (gC1qR), (8) C1q binding to complement receptor 1 (CR1), (9) C1q binding to B-amyloid, or (10) C1q binding to calreticulin. In other embodiments, the biological activity of C1q is (1) activation of the classical complement activation pathway, (2) reduction in lysis and/or reduction in C3 deposition, (3) activation of antibody and complement dependent cytotoxicity, (4) CH50 hemolysis, (5) a reduction in red blood cell lysis, (6) a reduction in red blood cell phagocytosis, (7) a reduction in dendritic cell infiltration, (8) inhibition of complement-mediated red blood cell lysis, (9) a reduction in lymphocyte infiltration, (10) a reduction in macrophage infiltration, (11) a reduction in antibody deposition, (12) a reduction in neutrophil infiltration, (13) a reduction in platelet phagocytosis, (14) a reduction in platelet lysis, (15) an improvement in transplant graft survival, (16) a reduction in macrophage mediated phagocytosis, (17) a reduction in autoantibody mediated complement activation, (18) a reduction in red blood cell destruction due to transfusion reactions, (19) a reduction in red blood cell lysis due to alloantibodies, (20) a reduction in hemolysis due to transfusion reactions, (21) a reduction in alloantibody mediated platelet lysis, (22) an improvement in anemia, (23) a reduction in eosinophilia, (24) a reduction in C3 deposition on red blood cells (e.g., a reduction of deposition of C3b, iC3b, etc., on RBCs), (25) a reduction in C3 deposition on platelets (e.g., a reduction of deposition of C3b, iC3b, etc., on platelets), (26) reduction in anaphylatoxin production, (27) a reduction in autoantibody mediated blister formation, (28) a reduction in autoantibody induced erythematosus, (29) a reduction in red blood cell destruction due to transfusion reactions, (30) a reduction in platelet lysis due to transfusion reactions, (31) a reduction in mast cell activation, (32) a reduction in mast cell histamine release, (33) a reduction in vascular permeability, (34) a reduction in complement deposition on transplant graft endothelium, (35) B-cell antibody production, (36) dendritic cell maturation, (37) T-cell proliferation, (38) cytokine production, (39) microglia activation, (40) Arthus reaction, (41) a reduction of anaphylatoxin generation in transplant graft endothelium, or (42) activation of complement receptor 3 (CR3/C3) expressing cells.

In some embodiments, CH50 hemolysis comprises human CH50 hemolysis. The antibody may be capable of neutralizing from at least about 50%, to about 100% of human CH50 hemolysis. The antibody may be capable of neutralizing about 50%, about 60%, about 70%, about 80%, about 90%, about 100% of human CH50 hemolysis. The antibody may be capable of neutralizing at least 50% of CH50 hemolysis at a dose of less than 150 ng/ml, less than 100 ng/ml, less than 50 ng/ml, or less than 20 ng/ml.

In some embodiments, the antibody is a monoclonal antibody, a polyclonal antibody, a recombinant antibody, a humanized antibody, a human antibody, a chimeric antibody, a monovalent antibody, a multispecific antibody, or an antibody fragment, or antibody derivative thereof. In some embodiments, the antibody is humanized antibody. In some embodiments, the antibody is antibody fragment, such as a Fab fragment. Examples of an antibody fragment are a Fab fragment, a Fab' fragment, a F(ab')2 fragment, a Fv fragment, a diabody, and a single chain antibody molecule. In some embodiments, the antibody comprises a light chain variable domain comprising an HVR-L1 having the amino acid sequence of SEQ ID NO: 5, an HVR-L2 having the amino acid of SEQ ID NO: 6, and an HVR-L3 having the amino acid of SEQ ID NO: 7. In some embodiments, the antibody comprises a heavy chain variable domain comprising an HVR-H1 having the amino acid sequence of SEQ ID NO: 9, an HVR-H2 having the amino acid of SEQ ID NO: 10, and an HVR-H3 having the amino acid of SEQ ID NO: 11. In some embodiments, the antibody comprises a light chain variable domain comprising an amino acid sequence with at least about 95% homology to the amino acid sequence selected from SEQ ID NO: 4 and 35-38 and wherein the light chain variable domain comprises an HVR-L1 having the amino acid sequence of SEQ ID NO: 5, an HVR-L2 having the amino acid of SEQ ID NO: 6, and an HVR-L3 having the amino acid of SEQ ID NO: 7. In some embodiments, the light chain variable domain comprising an amino acid sequence selected from SEQ ID NO: 4 and 35-38. In some embodiments, the antibody comprises a heavy chain variable domain comprising an amino acid sequence with at least about 95% homology to the amino acid sequence selected from SEQ ID NO: 8 and 31-34 and wherein the heavy chain variable domain comprises an HVR-H1 having the amino acid sequence of SEQ ID NO: 9, an HVR-H2 having the amino acid of SEQ ID NO: 10, and an HVR-H3 having the amino acid of SEQ ID NO: 11. In some embodiments, the heavy chain variable domain comprising an amino acid sequence selected from SEQ ID NO: 8 and 31-34. In some embodiments, the antibody is an antibody fragment comprising a heavy chain Fab fragment of SEQ ID NO: 39 and a light chain Fab fragment of SEQ ID NO: 40. The antibody may be administered by parenteral injection or infusion, such as a subcutaneous or intramuscular injection, or an intravenous injection or infusion.

In some embodiments, the antibody is a full-length antibody. In some embodiments, the antibody is administered to the subject by intravenous injection or infusion at a dose between 10 mg/kg and 150 mg/kg. In some embodiments, the antibody is administered to the subject by intravenous injection or infusion at a dose between 10 mg/kg and 20 mg/kg, 20 mg/kg and 30 mg/kg, 30 mg/kg and 40 mg/kg, 40 mg/kg and 50 mg/kg, 50 mg/kg and 60 mg/kg, 60 mg/kg and 70 mg/kg, 70 mg/kg and 80 mg/kg, 80 mg/kg and 90 mg/kg, 90 mg/kg and 100 mg/kg, 100 mg/kg and 110 mg/kg, 110 mg/kg and 120 mg/kg, 120 mg/kg and 130 mg/kg, 130 mg/kg and 140 mg/kg, or 140 mg/kg and 150 mg/kg. In some embodiments, the antibody is administered to the subject by intravenous injection or infusion at a dose between 75 mg/kg and 100 mg/kg. In some embodiments, the antibody is administered to the subject by intravenous injection or infusion at a dose of 75 mg/kg. In some embodiments, the antibody is administered to the subject by intravenous injection or infusion at a dose of 100 mg/kg. The antibody may be administered, once a week, once every other week, once every three weeks, or once a month. In some embodiments, the antibody is administered to the subject by intravenous injection or infusion at a dose of 75 mg/kg once a week. In some embodiments, the antibody is administered to the subject by intravenous injection or infusion at a dose of 75 mg/kg once every two weeks. In some embodiments, the antibody is administered to the subject by intravenous injection or infusion at a dose of 75 mg/kg once every three weeks. In some embodiments, the antibody is administered to the subject by intravenous injection or infusion at a dose of 75 mg/kg once a month. In some embodiments, the antibody is administered to the subject by intravenous injection or infusion at a dose of 100 mg/kg once a week. In some embodiments, the antibody is administered to the subject by intravenous injection or infusion at a dose of 100 mg/kg every two weeks. In some embodiments, the antibody is administered to the subject by intravenous injection or infusion at a dose of 100 mg/kg once every three weeks. In some embodiments, the antibody is administered to the subject by intravenous injection or infusion at a dose of 100 mg/kg once a month. The antibody may be administered, once a week, once every other week, or once a month. In some embodiments, the antibody is administered to the subject by subcutaneous or intramuscular injection at a dose between 1 mg/kg and 10 mg/kg. In some embodiments, the antibody is administered to the subject by subcutaneous or intramuscular injection at a dose between 1 mg/kg and 3 mg/kg, 3 mg/kg and 5 mg/kg, 5 mg/kg and 7 mg/kg, or 7 mg/kg and 10 mg/kg. In some embodiments, the antibody is administered daily, once every other day, once a week, once every other week, or once a month.

In some embodiments, the antibody is an antibody fragment. In some embodiments, the antibody fragment is administered to the subject by intravenous injection or infusion, by intramuscular injection, or by subcutaneous injection. In some embodiments, the antibody fragment is administered at a dose between 0.1 mg/kg and 50 mg/kg. In some embodiments, the antibody fragment is administered at a dose between 0.1 mg/kg and 1 mg/kg, 1 mg/kg and 5 mg/kg, 5 mg/kg and 10 mg/kg, 10 mg/kg and 15 mg/kg, 15 mg/kg and 20 mg/kg, 20 mg/kg and 25 mg/kg, 25 mg/kg and 30 mg/kg, 30 mg/kg and 35 mg/kg, 35 mg/kg and 40 mg/kg, 40 mg/kg and 45 mg/kg, or 45 mg/kg and 50 mg/kg. In some embodiments, the antibody fragment is administered at a dose between 0.3 mg/kg and 10 mg/kg. In some embodiments, the antibody fragment is administered daily, once every other day, once a week, once every other week, or once a month. In some embodiments, the antibody fragment is administered at an initial predose that is higher than the daily, once every other day, once a week, once every other week, or once a month dose. In some embodiments, the initial predose is between 3 mg/kg and 50 mg/kg. In some embodiments, the initial predose is between 3 mg/kg and 5 mg/kg, 5 mg/kg and 10 mg/kg, 10 mg/kg and 15 mg/kg, 15 mg/kg and 20 mg/kg, 20 mg/kg and 25 mg/kg, 25 mg/kg and 30 mg/kg, 30 mg/kg and 35 mg/kg, 35 mg/kg and 40 mg/kg, 40 mg/kg and 45 mg/kg, or 45 mg/kg and 50 mg/kg. In some embodiments, the initial predose is between 3 mg/kg and 20 mg/kg. In some embodiments, the antibody fragment has a shorter half-life as compared to its corresponding full-length antibody, such as the antibody fragment is rapidly cleared, thereby sparing C1q activity outside the subject's blood space, or the antibody selectively inhibits C1q within the subject's blood space, thereby sparing C1q activity outside the subject's blood space. In some embodiments, the blood space is confined within a blood vessel, such as an artery, an arteriole, a capillary, a venule, or a vein. The blood space may comprise serum, platelets, endothelial cells, blood cells, or hematopoietic cells. In some embodiments, inhibiting C1q within the subject's blood space reduces tissue damage in a highly vascularized tissue. Examples of highly vascularized tissues are kidney, alveoli, capillary bed, or glomerulus.

In some embodiments, the blood disorder is a complement-mediated blood disorder. In some embodiments, the blood disorder is cold agglutinin hemolytic anemia (cold agglutinin disease), cold antibody hemolytic anemia, ABO incompatible acute hemolytic reactions, warm agglutinin hemolytic anemia, warm antibody hemolytic anemia, warm autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, systemic lupus erythematosus (SLE), glomerulonephritis, anti-phospholipid antibody syndrome (APS), an infection, or a drug-induced hematologic disorder. The infection may be pneumonia, mycoplasma, mononucleosis, hepatitis C, human immunodeficiency virus (HIV), or coronavirus. Examples of the coronavirus are selected from SARS-CoV, MERS-CoV, HCoV, HKU1, and SARS-CoV-2. In some embodiments, the coronavirus is SARS-CoV-2. In some embodiments, the subject has SARS-CoV-2 infection, which has been confirmed by reverse-transcription polymerase chain reaction (RT-PCR) from respiratory tract or blood specimens. The blood disorder may be cold agglutinin hemolytic anemia (cold agglutinin disease), warm autoimmune hemolytic anemia (WAIHA), lupus nephritis, heparin-induced thrombocytopenia (HIT), heparin-induced thrombocytopenia and thrombosis (HITT), or immune thrombocytopenic purpura (ITP). Examples of the drug-induced hematologic disorder are aplastic anemia, agranulocytosis, megaloblastic anemia, hemolytic anemia, and thrombocytopenia.

The methods promote improved maintenance of blood cell activation in hematologic conditions associated with complement activation. The maintenance of blood function provides for functional improvement in hematologic disorders relative to untreated patients. The complement inhibitor (e.g., a C1q inhibitor such as an anti-C1q antibody, antibody fragment and/or antibody derivative) may be administered in an amount and with a frequency that are effective to maintain systemic complement inhibition in the subject.

It is contemplated that compositions may be obtained and used under the guidance of a physician for in vivo use. The dosage of the therapeutic formulation may vary widely, depending upon the nature of the disease, the frequency of administration, the manner of administration, the clearance of the agent from the host, and the like.

As used herein, "chronically administered," "chronic treatment," "treating chronically," or similar grammatical variations thereof refer to a treatment regimen that is employed to maintain a certain threshold concentration of a therapeutic agent in the blood of a patient in order to completely or substantially suppress systemic complement activity in the patient over a prolonged period of time. Accordingly, a patient chronically treated with a complement inhibitor may be treated for a period of time that is greater than or equal to 2 weeks (e.g., 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks; 1, 2, 3, 4, 5, 6, 7, 8, 9, 10, 11, or 12 months; or 1, 1.5, 2, 2.5, 3, 3.5, 4, 4.5, 5, 5.5, 6, 6.5, 7, 7.5, 8, 8.5, 9, 9.5, 10, 10.5, or 12 years or for the remainder of the patient's life) with the inhibitor in an amount and with a dosing frequency that are sufficient to maintain a concentration of the inhibitor in the patient's blood that inhibits or substantially inhibits systemic complement activity in the patient. In some embodiments, the complement inhibitor may be chronically administered to a patient in need thereof in an amount and with a frequency that are effective to maintain serum hemolytic activity at less than or equal to 20% (e.g., 19, 18, 17, 16, 15, 14, 13, 12, 11, 10, 9, 8, 7, 6, or even below 5%). In some embodiments, the complement inhibitor may be administered to a patient in an amount and with a frequency that are effective to maintain serum lactate dehydrogenase (LDH) levels at within at least 20% (e.g., 19, 18, 17, 16, 15, 14, 13, 12, 11, 10, 9, 8, 7, 6, or even below 5%) the normal range for LDH.

In some embodiments, the complement inhibitor is administered to the patient in an amount and with a frequency that are effective to maintain a serum LDH level less than 550 IU/L (e.g., less than 540, 530, 520, 510, 500, 490, 480, 470, 460, 450, 430, 420, 410, 400, 390, 380, 370, 360, 350, 340, 330, 320, 310, 300, 290, 280, or less than 270 IU/L). To maintain systemic complement inhibition in a patient, the complement inhibitor may be chronically administered to the patient, e.g., once a week, once every two weeks, twice a week, once a day, once a month, or once every three weeks. In some embodiments of any of the methods described herein, a complement inhibitor (e.g., an anti-C1q, anti-C1r, or anti-C1s antibody) may be administered to a patient in an amount and with a frequency of administration effective to maintain a concentration of at least 0.7 (e.g., at least 0.8, 0.9, one, two, three, four, five, six, seven, eight, nine, or 10 or more) divalent C1q, C1r, or C1s inhibitor molecule(s) (e.g., a whole anti-C1q antibody) per every C1q molecule in the patient's blood. "Divalent" or "bivalent," with respect to a C1q, C1r, or C1s inhibitor, refers to a C1q, C1r, or C1s inhibitor that contains at least two binding sites for a C1q, C1r, or C1s molecule. Where the C1q, C1r, or C1s inhibitor is monovalent (e.g., a single chain anti-C1q, anti-C1r, or anti-C1s antibody or a Fab that binds to C1q, C1r, or C1s), the inhibitor may be administered to the patient in an amount and with a frequency that are effective to maintain a concentration of at least 1.5 (e.g., at least 2, 2.5, 3, 3.5, 4, 4.5, or 5 or more) of the monovalent C1q, C1r, or C1s inhibitors per every C1q, C1r, or C1s molecule in the blood. In some embodiments, the monovalent C1q, C1r, or C1s inhibitor may be administered to the patient in an amount and with a frequency that are effective to maintain a ratio of monovalent C1q, C1r, or C1s inhibitor to C1q, C1r, or C1s of at least 2:1 (e.g., at least 3:1, at least 4:1, at least 5:1, or at least 6:1 or more). In some embodiments, a whole (bivalent) anti-C1q, anti-C1r, or anti-C1s antibody is administered to the patient in an amount and with a frequency that are effective to maintain a concentration of at least 40 μg (e.g., 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 75, 80, 85, 90, 95, 100, 110, or 120 μg or more) of the antibody per milliliter of the patient's blood. In preferred embodiments, a whole anti-C1q, anti-C1r, or anti-C1s antibody is administered in an amount and with a frequency to maintain the antibody at a concentration of at least 50 μg per milliliter of the patient's blood. In preferred embodiments, a whole anti-C1q, anti-C1r, or anti-C1s antibody is administered in an amount and with a frequency to maintain the antibody at a concentration of at least 100 μg per milliliter of the patient's blood. In some embodiments, a monovalent anti-C1q, anti-C1r, or anti-C1s antibody (e.g., a single chain antibody or an Fab fragment) may be administered to the patient in an amount and with a frequency that are effective to maintain a concentration of at least 80 μg (e.g., 81, 82, 83, 84, 85, 86, 87, 88, 89, 90, 91, 92, 93, 94, 95, 96, 97, 98, 99, 100, 110, 115, 120, 125, 130, 135, 140, 145, 150, 155, 160, 165, or a 170 μg or more) of the antibody per milliliter of the patient's blood.

The effective amount of a therapeutic composition given to a particular patient may depend on a variety of factors, several of which may be different from patient to patient. Utilizing ordinary skill, the competent clinician will be able to tailor the dosage of a particular therapeutic or imaging composition in the course of routine clinical trials.

Therapeutic agents, e.g., inhibitors of complement, activators of gene expression, etc. can be incorporated into a variety of formulations for therapeutic administration by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. Accordingly, administration of the compounds can be achieved in various ways, including oral, buccal, rectal, parenteral, subcutaneous, intraperitoneal, intradermal, transdermal, intrathecal, nasal, intratracheal, etc., administration. The active agent may be systemic after administration or may be localized by the use of regional administration, intramural administration, or use of an implant that acts to retain the active dose at the site of implantation.

Combination Treatments

The complement inhibitors of the present disclosure may be used, without limitation, conjointly with any additional treatment, such as immunosuppressive therapies, for treating a blood disorder.

In some embodiments, an antibody, antibody fragment and/or antibody derivative disclosed herein is administered in combination with an inhibitor of the alternative pathway of complement activation. Such inhibitors may include, without limitation, factor B blocking antibodies, factor D blocking antibodies, soluble, membrane-bound, tagged or fusion-protein forms of CD59, DAF, CR1, CR2, Crry or Compstatin-like peptides that block the cleavage of C3, non-peptide C3aR antagonists such as SB 290157, Cobra venom factor or non-specific complement inhibitors such as nafamostat mesilate (FUTHAN; FUT-175), aprotinin, K-76 monocarboxylic acid (MX-1) and heparin (see, e.g., T. E. Mollnes & M. Kirschfink, Molecular Immunology 43 (2006) 107-121). In some embodiments, the antibodies of this disclosure are administered in combination with an inhibitor of the interaction between the autoantibody and its autoantigen. Such inhibitors may include purified soluble forms of the autoantigen, or antigen mimetics such as peptide or RNA-derived mimotopes, including mimotopes of the AQP4 antigen. Alternatively, such inhibitors may include blocking agents that recognize the autoantigen and prevent binding of the autoantibody without triggering the classical complement pathway. Such blocking agents may include, e.g., autoantigen-binding RNA aptamers or antibodies lacking functional C1q, C1r, or C1s binding sites in their Fc domains (e.g., Fab fragments or antibodies otherwise engineered not to bind C1q, C1r, or C1s).

In some embodiments, an inhibitor of complement (e.g., an inhibitor of C1q, C1r, or C1s such as an anti-C1q, anti-C1r, or anti-C1s antibody or antigen-binding fragment, or antibody derivative thereof) described herein may be formulated with one or more additional active agents useful for treating a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA) autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or antiphospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin) or ameliorating a symptom thereof. For example, an anti-C1q, anti-C1r, or anti-C1s antibody may be formulated with an antihypertensive, an anticoagulant, and/or a steroid (e.g., a corticosteroid). Examples of anticoagulants include, e.g., warfarin (Coumadin), aspirin, heparin, phenindione, fondaparinux, idraparinux, and thrombin inhibitors (e.g., argatroban, lepirudin, bivalirudin, or dabigatran). An inhibitor of C1q, C1r, or C1s (e.g., an anti-C1q, anti-C1r, or anti-C1s antibody) may also be formulated with a fibrinolytic agent (e.g., ancrod, ε-aminocaproic acid, antiplasmin-ai, prostacyclin, and defibrotide), cyclophosphamide, or an anti-cytokine agent. Anti-cytokine agents include, e.g., antibodies or soluble receptors that bind to and modulate the activity of a cytokine (e.g., a pro-inflammatory cytokine such as IL-13). In some embodiments, the inhibitor can be formulated with, or for use with, an anti-CD20 agent such as rituximab (Rituxan™; Biogen, Cambridge, MA). In some embodiments, the inhibitor of C1q, C1r, or C1s may be formulated for administration to a subject along with intravenous immunoglobulin therapy (IVIG) or with plasma exchange.

When the inhibitor of C1q, C1r, or C1s is to be used in combination (e.g., conjointly) with a second active agent, or when two or more inhibitors of C1q, C1r, or C1s are to be used (e.g., an anti-C1q, anti-C1r, or anti-C1s antibody), the agents may be formulated separately or together. For example, the respective pharmaceutical compositions may be mixed, e.g., just prior to administration, and administered together or can be administered separately, e.g., at the same or different times.

A composition may be formulated comprising an anti-C1q, anti-C1r, or anti-C1s antibody such that it includes a therapeutically effective amount of an inhibitor of C1q, C1r, or C1s (e.g., an anti-C1q, anti-C1r, or anti-C1s antibody or antigen-binding fragment, or antibody derivative thereof) or the composition may be formulated to include a sub-therapeutic amount of the inhibitor and a sub-therapeutic amount of one or more additional active agents such that the components in total are therapeutically effective for treating a blood disorder (e.g., cold agglutinin hemolytic anemia (cold agglutinin disease), hemolytic anemia, ABO incompatible acute hemolytic reactions, warm agglutinin hemolytic anemia, warm antibody hemolytic anemia, warm antibody autoimmune hemolytic anemia (WAIHA), autoimmune hemolytic anemia (AIHA), autoimmune thrombocytopenia, paroxysmal cold hemoglobinuria (PCH), antiphospholipid syndrome (APS), Evan's syndrome, ABO incompatible acute hemolytic reactions, neonatal alloimmune thrombocytopenia, red blood cell alloimmunization, Felty's syndrome, antibody mediated thrombocytopenia, heparin-induced thrombocytopenia (HIT), heparin-induced thrombocytopenia and thrombosis (HITT), thrombotic thrombocytopenic purpura (TTP), immune thrombocytopenic purpura (ITP), thrombocytopenia, thrombosis, vasculitis, lupus nephritis, glomerulonephritis, and/or antiphospholipid antibody syndrome (APS), autoimmune disorders (e.g., Systemic lupus erythematosus (SLE), Crohn's disease, ulcerative colitis), infections (e.g., pneumonia, mycoplasma, mononucleosis, Hepatitis C, human immunodeficiency virus (HIV), coronavirus), immune complex diseases (e.g., cryoglobulinemia, serum sickness, glomerulonephritis), or drug-induced hematologic disorders (e.g., aplastic anemia, agranulocytosis, megaloblastic anemia, hemolytic anemia, thrombocytopenia) from drugs such as penicillin, quinine, or heparin). In some embodiments, a composition may be formulated to include two or more inhibitors of C1q, C1r, or C1s, each at sub-therapeutic doses, such that the inhibitors in total are at a concentration that is therapeutically effective for treating a blood disorder. Methods for determining a therapeutically effective dose (e.g., a therapeutically effective dose of an anti-C5 antibody) are known in the art and described herein.

In some embodiments, the antibodies of this disclosure may be administered in combination with other therapies for blood disorders. For example, the composition may be administered to a subject at the same time, prior to, or after, plasmapheresis, IVIG therapy, plasma infusion, or plasma exchange.

EXAMPLES

Example 1: Anti-C1q Antibodies Inhibit Complement-Mediated Hemolysis in Blood Samples from CAD Individual CAD serum samples were pooled together for hemolysis and FACs experiments with anti-C1q antibody-titration. Hemolysis was performed by sensitizing RBCs with pooled CAD sera (1 hr at 4° C.–10 μL sera+10 μL RBC). Lysis was triggered adding 200 μL of 20× normal human serum at 37° C. for 35 minutes. After lysis, supernatant was removed and hRBCs were stained with anti-C3 antibody (CT-C3), anti-C1q antibody, and anti-C4 antibody for 30 minutes, washed once, stained with Fluorescent secondary anti-goat antibody for FACS analysis.

Figure 2B:
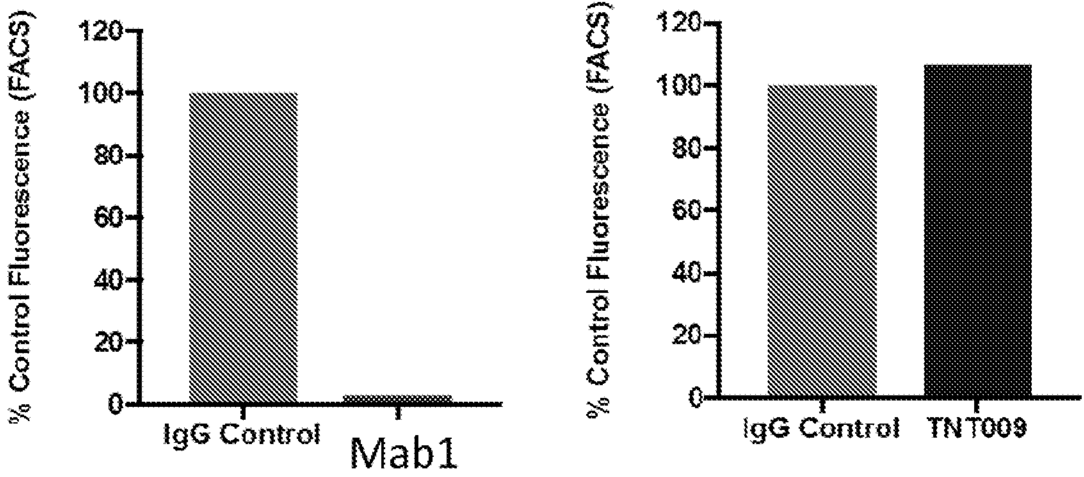

In CAD, RBC's become coated with the three major classical complement "opsonins", C1q, C4b and C3b, that drive RBC clearance via "extravascular lysis". C1q, C4b and C3b are recognized in the spleen and liver by the reticuloendothelial system for RBC removal. Also in CAD, RBC's become coated with C5b, which triggers formation of membrane attack complex for direct "intravascular" RBC lysis. Anti-C1q antibody effectively arrests both intravascular and extravascular RBC lysis processes in CAD serum samples. Anti-C1q inhibits deposition of all major "opsonins"/immune cell ligands (C1q, C4b & C3b) of the complement cascade (FIG. 1A). Full-length anti-C1q antibody (e.g., Mab1 antibody comprising heavy chain variable domain of SEQ ID NO: 33 and light chain variable domain of SEQ ID NO: 37) and anti-C1s (e.g., TNT009) antibodies inhibit complement-mediated hemolysis (FIG. 1B). Anti-C1q antibody is at least as potent as TNT009 for inhibition of hemolysis (FIG. 2A) while only anti-C1q antibody inhibits upstream binding of C1q to target cells (FIG. 2B). Anti-C1s antibody does not block C1q binding to RBC. Selectively blocking C1q fully blocks hemolysis induced by the Classical Pathway but preserves hemolysis induced via the Lectin and Alternative pathways. In contrast, anti-C5 block hemolysis activity of all three pathways. (FIG. 3). Serum biomarkers of complement depletion/consumption in CAD patients provide additional assessments. Decrease in C4 and C2, but not C5, shows over-activation of early complement cascade with consumption of early complement components (FIG. 4). CAD can be treated by subcutaneous administration of anti-C1q antibody (e.g., FabA, anti-C1q antibody Fab fragment comprising heavy chain Fab fragment of SEQ ID NO: 39 and light chain Fab fragment of SEQ ID NO: 40) to inhibit RBC lysis in primates (FIG. 5).

Example 2: Anti-C1q Antibodies Inhibit Hemolysis and Complement Deposition in Blood Samples from CAD Patients CAD and Control Plasma Samples Human CAD plasma samples from 8 subjects were obtained under an IRB approved protocol. Control serum and plasma samples were obtained from Innovative Research (Novi, MI).

Ex Vivo Sensitization of Human RBCs

Human RBCs (Innovative Research, MI) were washed and suspended in GVB++buffer (Comptech, TX) (80 μL packed RBCs in 2 mL GVB++buffer). 25 μL of human RBCs were mixed with 25 μL 5× diluted CAD or normal sera and incubated at 4 C for 30 minutes. This step allows cold agglutinin antibodies, from CAD subjects, to bind to human RBC surface antigens.

Three subjects showed robust IgG deposition, while seven subjects showed robust IgM deposition. One subject showed low signal for both cell surface IgG and IgM.

Hemolysis Assay

Addition of normal human serum to the CAD-sensitized RBCs results in complement recruitment and activation. Normal human serum (20× diluted in GVB++buffer) was added to the sensitized human RBCs in GVB++ or GVB-EDTA buffer. For pharmacology studies, anti-C1q antibody (e.g., Mab2 antibody comprising heavy chain variable domain of SEQ ID NO: 8 and light chain variable domain of SEQ ID NO: 4) and FabA (e.g., Fab fragment comprising heavy chain Fab fragment of SEQ ID NO: 39 and light chain Fab fragment of SEQ ID NO: 40) were titrated into the serum at a range of concentrations from 100 ug/mL to 0.3 ug/mL. RBCs were incubated for 30 mins at 37 C to allow C1q recruitment and activation of the classical complement cascade on human RBCs.

Sensitized RBCs incubated in serum diluted in GVB-EDTA buffer (Comptech, TX) was the negative control, since EDTA results in a complete inhibition of hemolysis via the complement cascade. RBCs incubated in water was the positive control to define maximal lysis possible in each preparation of RBCs and experimental run.

Following incubation at 37 C for 30 minutes, cells were spun down at 2000 rpm for 5 minutes in a centrifuge. Supernatants were transferred to a clear bottom 96 well plates and absorbance at 415 nm (hemoglobin specific absorbance) was read in a plate reader (Spectramax, CA), to quantify hemolysis. The absorbance signal from wells with serum in GVB-EDTA buffer was subtracted from all other wells in order to provide a measure of lysis that is specifically driven by the classical complement cascade. The EDTA-corrected absorbance signal was plotted and evaluated. For pharmacology studies, signal in each well was also normalized to wells lacking anti-C1q antibody and % change in signal was plotted (FIGS. 6A and 6B). 4PL-logistic fits were performed to determine the IC50 for hemolysis inhibition with anti-C1q MAB2 and FabA. The relative IC50 for inhibition of hemolysis was ~10 nM for both anti-C1q MAB2 and FabA.

Flow Cytometry for Evaluating Complement Deposition on Human RBCs

Human RBCs that were not lysed in the above reaction were washed with dPBS containing 1% BSA and 2 mM EDTA (FACS buffer), then stained with anti-C4 goat polyclonal antibody (Abcam Ab47788) and an anti-C3d specific polyclonal rabbit antibody (Agilent A0063) for 30 minutes on ice. Cells were then washed with FACS buffer, spun and then stained with secondary antibodies, anti-goat Alexa 647 conjugate and anti-Rabbit Alexa 488 conjugate (Thermo, CA). Following incubation for 30 minutes on ice, cells were washed with FACS buffer and then run in flow cytometer (Novocyte system, ACEA, CA).

Following the CAD sensitization step, RBC cell surface IgG and IgM was detected with respective fluorescently tagged anti-human IgG/IgM antibodies in order to understand the nature of anti-RBC antibodies in individual CAD subjects.

For flow analysis of RBCs, forward scatter (FSC) and side scatter signal (SSC) was used to identify the RBC population. Single cell RBC population was isolated by selecting cells along the diagonal of the FSC area vs FSC width plot. Single cell RBCs positive for fluorescence signal in the green (488 nm) and far red (647 nm) channels was used to define the cells positively labeled for cell surface C4 and C3d, respectively. The GVB-EDTA buffer subtracted % labeled cells for C4 and C3d staining were evaluated for differences between CAD and control subjects. For pharmacology studies, % labeled cells in wells containing MAB2 or FabA were normalized to wells lacking anti-C1q antibody and plotted as a percent change (FIGS. 6A and 6B). 4PL-logistic fits were performed to determine the IC50 of inhibition of C4 and C3d deposition with MAB2 and FabA in these studies. The relative IC50 for inhibition of complement deposition was ~10 nM for both anti-C1q MAB2 and FabA.

Example 3: Complement Activation by PF4/Heparin Through the Classical Pathway in Plasma from Patients with Heparin-Induced Thrombocytopenia (HIT)

Figure 7A:
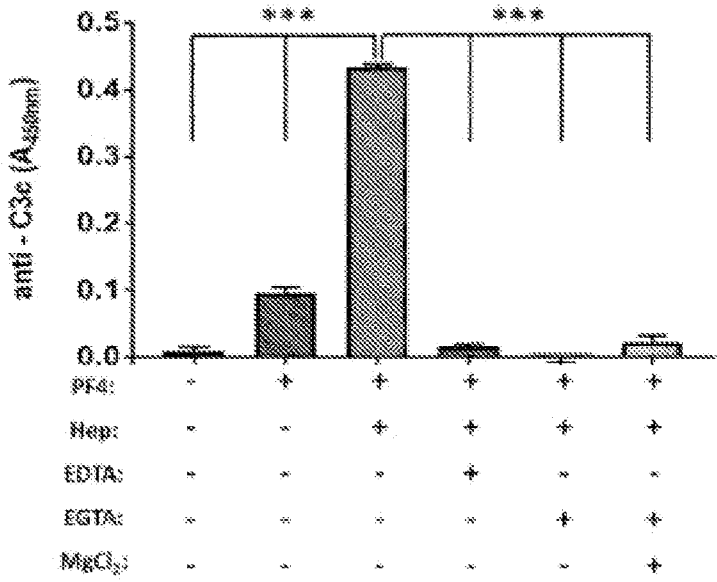
FIGS. 7A-7G show that PF4/heparin activates complement by classical pathway.
Figure 7B:
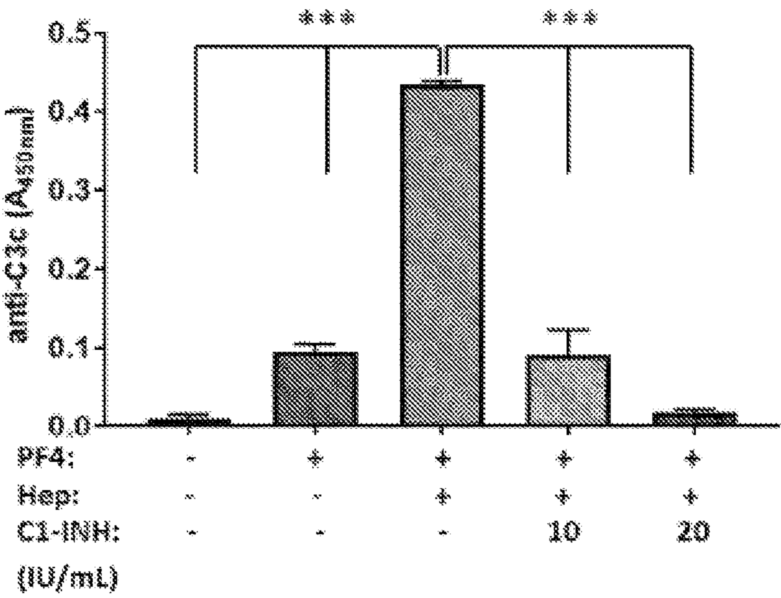
Figure 7C:
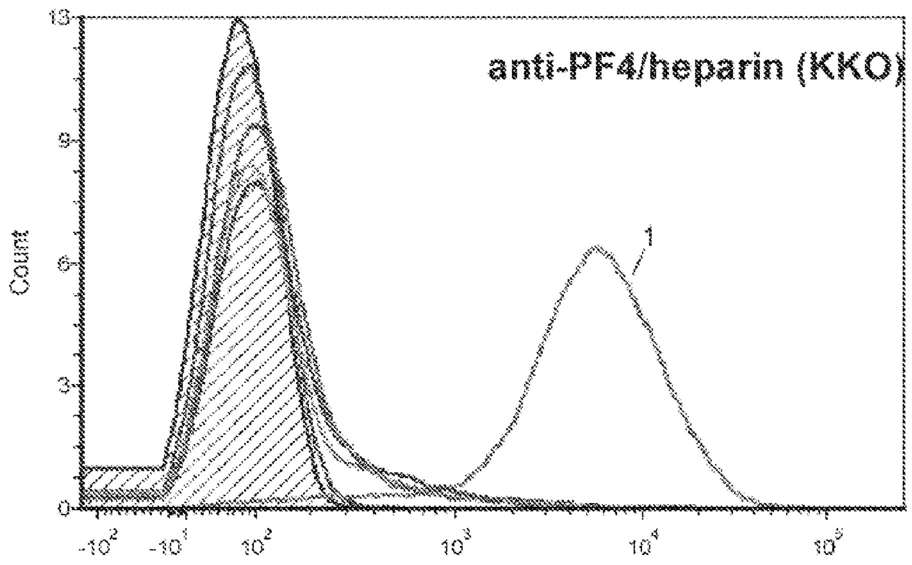
Figure 7D:
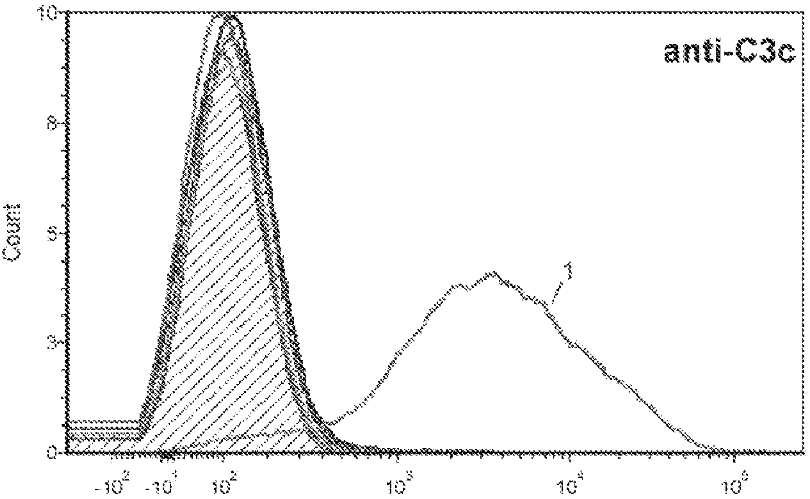
Figure 7E:
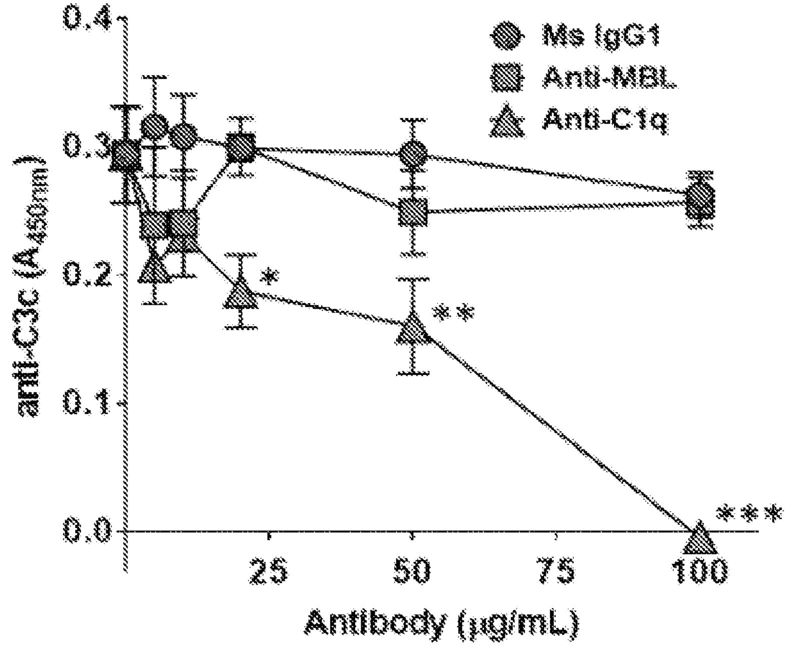

In HIT, RBC's are lysed when a patient develops antibodies against therapeutically administered heparin in combination with the endogenous circulating protein PF4. To confirm that this lysis is mediated by the classical pathway, rather than the alternative pathway, differential chelation studies using EDTA and EGTA were performed in vitro with plasma from a HIT patient. The alternative pathway, sensitive to Mg2+, is inhibited by EDTA, but not EGTA. As shown in FIG. 7A, addition of EDTA or EGTA to plasma prior to addition of PF4/heparin eliminated complement activation. Further, Mg2+ supplementation of EGTA-treated plasma did not rescue complement activation by PF4/heparin. Plasma from a healthy donor was incubated with or without C1-inhibitor (10 and 20 IU/mL) before incubating with PF4/heparin and complement activation by PF4/heparin was determined by antigen-C3c capture ELISA assay. As shown in-FIG. 7B, complement activation was reduced using C1 esterase inhibitor. Similar results were obtained in whole blood assay using flow cytometry (FIG. 7C-7D). Whole blood from a healthy donor was incubated with or without EDTA (10 mM) or EGTA (10 mM)±$MgCl_2$ (10 mM) before incubating with buffer or antigen (PF4; 25 g/mL f heparin; 0.25 U/mL) and binding of PF4/heparin and C3c to B cells was determined by flow cytometry.

Figure 7F:
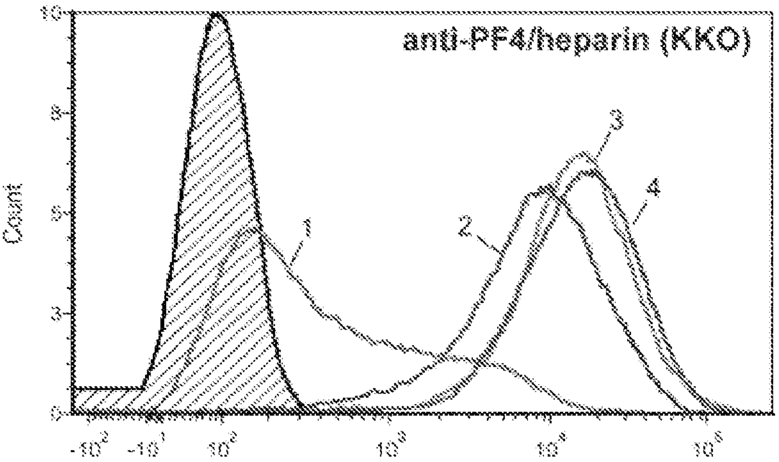
Figure 7G:
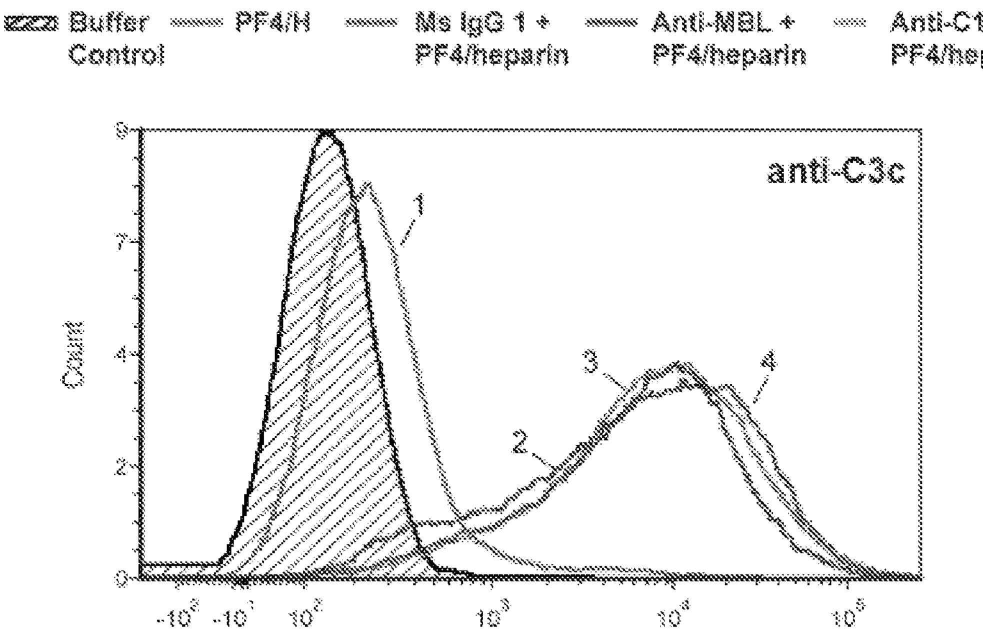

To examine involvement of the lectin and classical pathways, plasma or whole blood from a healthy donor was pre-incubated with various concentration of monoclonal antibodies to C1q (anti-C1q Mab, Cell Sciences, Inc., Newburyport, MA) or MBL or murine isotype controls (0-100 μg/mL) before adding PF4/heparin. Complement activation responses to PF4/heparin were assessed by immunoassay (FIG. 7E) or flow cytometry (FIG. 7F-7G). For the flow cytometry experiments, whole blood from a healthy donor was incubated with 100 μg/mL of mouse IgG1 or anti-MBL antibody or anti-C1q antibody before incubating with PF4/heparin. Binding of PF4/heparin and C3c to B cells was determined by flow cytometry.

Anti-C1q Mab inhibited complement activation by PF4/H in a concentration dependent manner, whereas anti-MBL antibodies or mouse isotype control did not. Additionally, in data not shown, involvement of individual lectin proteins, ficolin-2 and -3 in complement activation by PF4/heparin complexes was excluded. Mass spectrometry data accompanying FIG. 8 did not show correlation of lectin proteins with complement activation phenotype, nor was functional inhibition of ficolin-2 associated with loss of complement activation in an immunoassay.

These studies establish that complement is activated by PF4/heparin through the classical complement pathway. Additionally, the studies demonstrate that significant donor variation in circulating IgM levels that can contribute to host susceptibility for immune activation and offer targets for therapeutic intervention to prevent HIT.

Example 4: Anti-C1q Prevents KKO-Inducted Thrombosis Formation in a Laser Microvascular Injury Model A heparin-induced thrombocytopenia/thrombosis transgenic mouse model expressing both human platelet FcγRIIA and hPF4 is described by Reilly, et al., *Blood.* 2001 Oct. 15; 98(8): 2442-7 and is used in this experiment. Anti-C1q antibodies (AntiC1q Mab1, Mab2, and Fab and isotype controls) are injected intravenously into the transgenic mice. The percent change in thrombus size is measured based on binding of fluorescently labelled platelets in mice receiving any of the antiC1q Mab1, Mab2, Fab or the isotype controls followed by KKO.

Example 5: Anti-C1q Antibody Inhibits Complement Deposition in Blood Samples from wAIHA Patients Human wAIHA plasma samples from 2 subjects were obtained under an IRB approved protocol. Control serum and plasma samples were obtained from Innovative Research, MI.

Human RBCs (Innovative Research, MI) were suspended in GVB++buffer (Comptech, TX) (0.5 mL Type O+Single Donor Washed RBCs in 10 mL GVB++buffer), centrifuged at 2000 rpm for 5 minutes and the supernatant was decanted. Cells were resuspended to 0.5 mL with GVB++ and 1 mL of 0.5% Bromelain in dPBS (w/v) was added. Cells were incubated at 37 C for 10 minutes, and 10 mL GVB++buffer was then added and centrifuged at 2000 rpm for 5 minutes. The supernatant was decanted and the cells resuspend to 0.5 mL with GVB++. A 0.5% RBC solution was created by adding 5 uL of resuspended cells to 995 uL of GVB++.

Clear bottom 96 well plates were used, and in each well, the following reagents were added: healthy donor serum (37.5 μL); 200 μg/mL Eculizumab in GVB++(37.5 μL);

patient serum (7.5 μL); GVB++(42.5 μL) either without drug or with MAB2 (1058 ug/mL) for final concentration of 300 ug/mL; and 0.5% RBC in GVB++(25 μL).

Following incubation at 37 C for two hours, a wash of flow buffer (1% BSA w/v, 2 mM EDTA, dPBS) was added and cells were spun down at 2000 rpm for 5 minutes in a centrifuge. Supernatants were removed and pellets were resuspended in 100 μL of flow staining solution (1:2000 Fluorescein-conjugated anti-C1q (Dako), 1:1500 Phycoerythrin-conjugated anti C3d (Dako), 1:1000 Allophycocyanin-conjugated anti-C4 (Abcam)), and stained in the dark at 4 C for 30 min. Following incubation, a wash of 150 uL flow buffer was added and the cells were centrifuged for 5 min at 2000 rpm. Supernatant was removed and cells were resuspended in 125 uL flow buffer.

Figure 13:
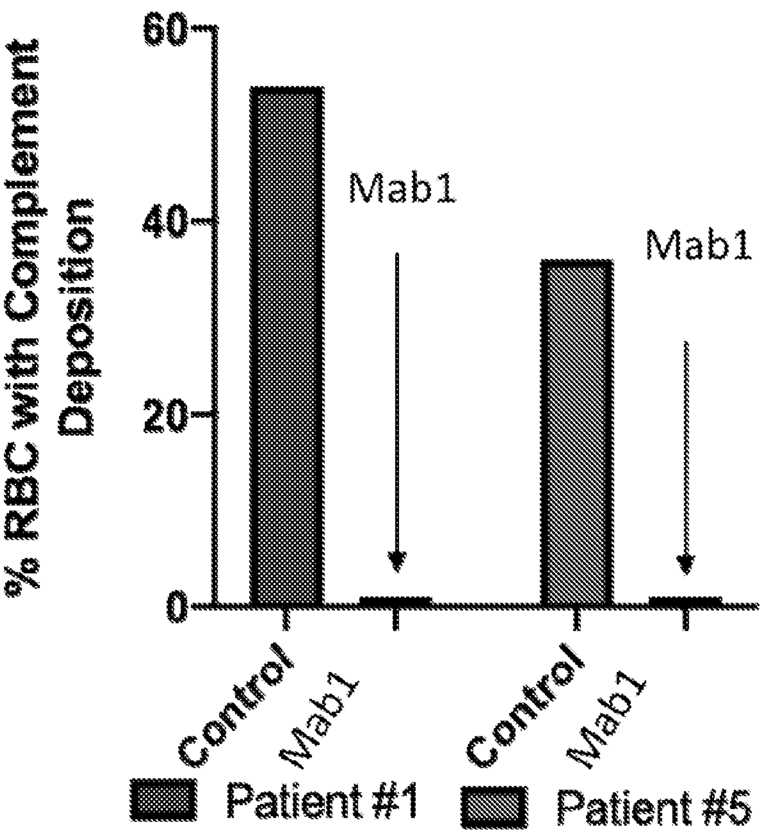
FIG. 13 shows complement deposition in samples from wAIHA patients and inhibition of deposition with anti-C1q antibody (Mab2).

For flow analysis of RBCs, forward scatter (FSC) and side scatter signal (SSC) was used to identify the RBC population. Single cell RBC population was isolated by selecting cells along the diagonal of the FSC area vs FSC width plot. Single cell RBCs positive for fluorescence signal in the far red (647 nm) channels was used to define the cells positively labeled for cell surface C4. GVB EDTA samples were used as a negative control for complement deposition. For pharmacology studies, % labeled cells in wells containing MAB2 were compared to wells lacking anti-C1q antibody and plotted as a percent change (FIG. 13). This figure shows that sera from patients with wAIHA contain antibodies against RBC that cause complement activation and deposition (as measured by C4). Mab 1 fully prevented activation of C1q and deposition of C4.

Example 6: A Clinical Trial of Anti-C1q Monoclonal Antibody (MAB1) in Patients with Warm Autoimmune Hemolytic Anemia (wAIHA)

The primary objective of this clinical trial is to evaluate the safety, tolerability, and efficacy of two once-weekly intravenous infusions of Mab1 (30, 50, 75 or 100 mg/kg) in subjects with Warm Autoimmune Hemolytic Anemia (wAIHA).

Study design: This is a repeat dose clinical trial in adult male and female subjects with wAIHA. This study is designed to evaluate the safety, tolerability, and efficacy of Mab1 in subjects with wAIHA. Subjects will receive an IV infusion of Mab1 (30, 50, 75 or 100 mg/kg on Day 1 and Day 8.

Methodology: A total of 6 to 12 subjects with wAIHA will be enrolled in each cohort (i.e., 30, 50, 75 and 100 mg/kg Mab1). All subjects will receive an IV infusion on Day 1 followed by a second IV infusion on Day 8.

Screening visit (Week −6 and Week −2): All subjects undergo study screening procedures within 42 days prior to dosing with Mab1. Screening includes obtaining informed consent, an assessment of medical history and study eligibility, review of vaccination history, baseline health, administration of the FACIT Fatigue questionnaire, and clinical laboratory tests, including a DAT and markers of hemolysis (reticulocyte count, haptoglobin, LDH and indirect bilirubin). Study visits: Subjects will receive an intravenous infusion of 30, 50, 75 or 100 mg/kg Mab1 on Day 1 and Day 8.

Study assessments for safety, PK, and PD on Days 3 and 4 may be completed either in-clinic or at-home. Subjects will return to the clinic to have study assessments for safety, PK, and PD on Days 15, 22, 29, 36, 43, 50, 57 and 71.

Study Assessments: Pharmacokinetic parameters are assessed by serial serum sampling, and pharmacodynamic parameters are assessed by measurement of CH50 and C4, and other complement biomarkers in blood, blood cell flow cytometry for complement components and reduction in disease-related biomarkers (e.g., hemoglobin, reticulocyte count, haptoglobin, lactase dehydrogenase, bilirubin, etc.).

Example 7: Daily Subcutaneous Dosing of Anti-C1q Antibody Fab Fragment ("FabA") in Cynomolgus Monkeys Cynomolgus monkeys (2 Females/group) were dosed once with an anti-C1q antibody Fab fragment (comprising heavy chain Fab fragment of SEQ ID NO: 39 and light chain Fab fragment of SEQ ID NO: 40)("FabA") subcutaneously for a week in the interscapular space—5 mg/kg on day 1 and 2 mg/Kg for 6 consecutive days. Blood was collected and processed for $K_2$Edta plasma and serum at the following time points: predose, 1, 3, 6, 12, and 24 hours post-dose, and on Days 3, 4, 5, 6, 7, 8, 9, and 10. Blood collections on Days 2 through 7 were done prior to dosing on those days.

PK and PD ELISA Assays:

The levels of serum Free-FabA (PK), plasma Free-C1q (PD) and plasma Total-C1q (PD) were measured using sandwich ELISAs. Black 96 well plates (Costar #3925) were coated with 75 μL of respective capture protein/antibody (Table 1) in bicarbonate buffer (pH 9.4) overnight at 4 C. Next day, the plates were washed with dPBS pH 7.4 (Dulbecco's phosphate-buffered saline) and then blocked with dPBS buffer containing 3% bovine serum albumin (BSA). Standard curves were prepared with purified proteins (Table 1) in assay buffer (dPBS containing 0.3% BSA and 0.1% Tween20). Study serum or plasma samples were prepared in the assay buffer at respective dilutions. The blocking buffer was removed from the plate by tapping. Standards and samples were added at 75 μL per well in duplicates and incubated with shaking at 300 rpm at room temperature for 1 hr for PK measurements, and subsequently overnight at 4 C followed by 37 C for 30 minutes and room temperature for 1 h for C1q assays. Plates were washed three times with dPBS containing 0.05% Tween20 and 75 μL of alkaline-phosphatase conjugated secondary antibodies (Table 1) were added to all wells. Plates were incubated at room temperature with shaking for 1 h. Plates were washed three times with dPBS containing 0.05% Tween20 and developed using 75 μL of alkaline phosphatase substrate (Life Technologies, T2214). After 20 minutes at room temperature, plates were read using a luminometer. Standards were fit using a 4PL logistic fit and concentration of unknowns determined. Analyte levels were corrected for dilution and then plotted using GraphPad Prism.

TABLE 1

Standards and antibodies used in PK/PD ELISA assays

| Assay | Capture protein/antibody (source) | Capture Concentration | Standard (range) | Sample dilution factor | Secondary ab (dilution) |
|---|---|---|---|---|---|
| PK (Free-FabA) | Human C1q (Complement Tech A100) | 2 μg/mL | FabA (0.02-50 ng/mL) | 40x, 200x, 1000x | Goat anti-human kappa-AP (1:4000) |
| PD (Free-C1q) | JL-1 (abcam 71940) | 1 μg/mL | Human C1q (0.01-30 ng/mL) | 80,000x | M1-AP (1:2000) |
| PD (Total-C1q) | Polyclonal anti-C1q (Dako A0136) | 2 μg/mL | | 40,000x | Dako Polyclonal anti C1q-AP (1:2000) |

Figure 10:
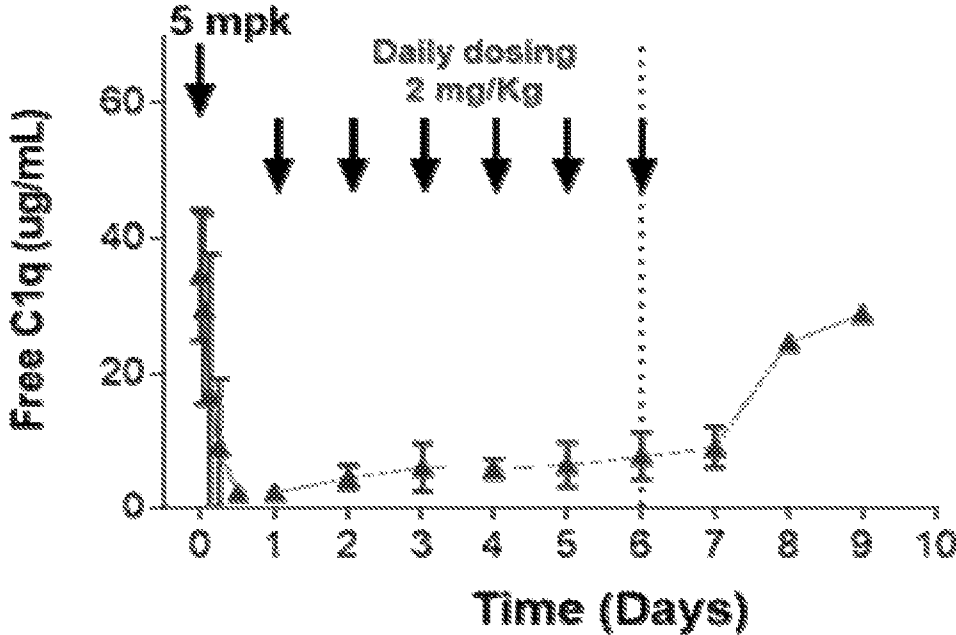
FIG. 10 shows reduction of Free-C1q in plasma from animals treated with 5+2 mg/kg FabA. Lower limit of quantification=1.1 μg/mL.

Free-FabA levels were measured in serum samples of all treated animals (FIG. 9). Plasma Free-C1q levels, which indicate the amount of C1q that is not bound to FabA were measured in plasma samples from treated animals (FIG. 10).

Ex-Vivo Hemolysis Assay:

Serum samples from cynomolgus monkeys were used as a source of complement to follow complement-mediated lytic activity on antibody-sensitized sheep red blood cells (RBCs). Sheep RBCs pre-sensitized with an anti-RBC antibody (CompTech #B200) were suspended in Gelatin veronal buffered saline containing calcium and magnesium (GVB++) (CompTech #B102). RBCs were washed three times with GVB++ to remove any non-specific signal from prelysed RBCs by spinning at 2000 rpm for 5 minutes at 4-6 C. Cells were resuspended in GVB++ at a final concentration of ~200 million cells/mL and kept on ice. Cynomolgus monkey serum samples collected at baseline and following dosing with FabA were diluted 50-fold in GVB++ and 50 μL each were added to round-bottom clear plates. The lysis reaction was triggered by adding 50 μL of the RBCs to the serum samples and incubated at 37 C for 20 minutes. Plates were then spun at 2000 rpm for 5 minutes; supernatants were transferred to a clear flat-bottom 96 well plates and absorbance read at 415 nm in a plate reader. Control samples were run to estimate background signal with buffer control without serum or serum samples prepared in GVB buffer containing EDTA. Sample signal was background subtracted, normalized to baseline and then plotted as a percent of baseline to determine the time course of hemolysis and the relative inhibition of hemolysis following dosing with FabA.

Figure 11:
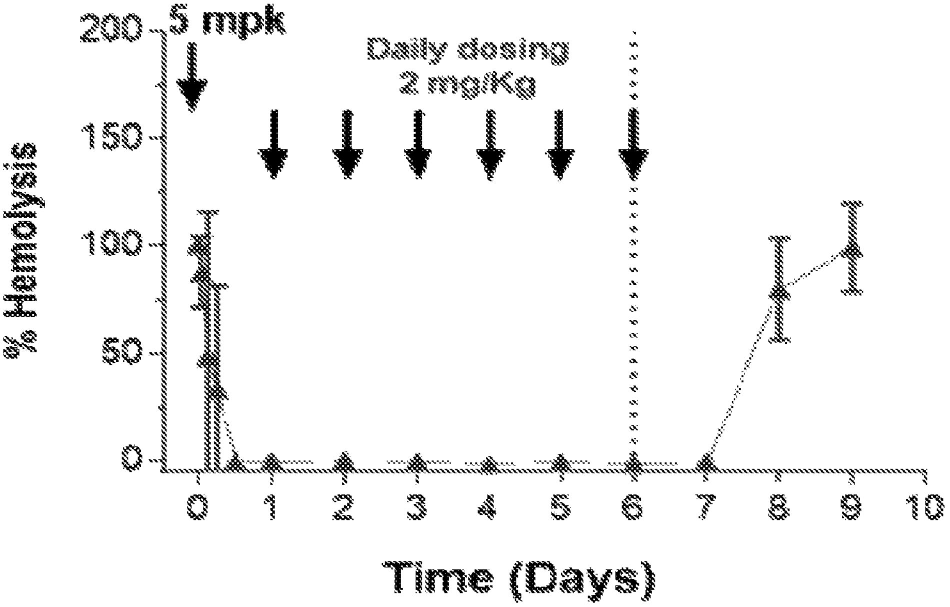
FIG. 11 shows that serum hemolysis was inhibited following repeated daily subcutaneous dosing of FabA.

Serum hemolysis was inhibited following repeated daily subcutaneous dosing of FabA (FIG. 11).

Subcutaneous dosing of FabA in monkeys at 5 mg/Kg followed by 2 mg/Kg once daily led to robust PK with measurable Free-drug levels in both groups of animals until at least 1 day following the last dose. Free-C1q levels were fully inhibited after the 5 mg/Kg dose, and with repeated once daily 2 mg/Kg doses, Free-C1q levels were inhibited in the range of 60-90% over the time period of dosing and at least one day after the last dose. Plasma total C1q levels were unaltered over the time period of this study in both dose groups, suggesting that FabA does not significantly affect C1q turnover. These results confirms that multiple SC dosing with FabA at 2 mg/kg or higher can result in robust Free-drug levels in blood and can inhibit Free-C1q and serum hemolytic activity in monkeys.

Example 8: Assessment of Blood Versus Tissue Distribution of an Anti-C1q Inhibitor This example is used to demonstrate that daily subcutaneous (SC) administration of a defined dose of an anti-C1q inhibitor (e,g, an anti-C1q antibody Mab1, Mab2 or FabA) leads to complete saturation and inhibition of C1q in the blood (i.e., intravascular space), without being sufficient to completely saturate or inhibit C1q in tissue compartments (i.e., extravascular space), as compared to an anti-C1q inhibitor that is delivered via intravenous infusion or injection.

Animal Species. An animal species is first identified wherein the anti-C1q inhibitor(s) bind to C1q with high affinity and they exhibit complete functional inhibition of the classical complement cascade in serum.

Anti-C1q Inhibitor Dose Selection: The animals are first treated with doses of 1, 3, 5 and 10 mg/Kg of the anti-C1q FabA (e.g., the anti-C1q Fab comprising heavy chain Fab fragment of SEQ ID NO: 39 and light chain Fab fragment of SEQ ID NO: 40), and/or with doses of 3, 5, 7 and 10 mg/Kg of the anti-C1q monoclonal antibody (e.g., Mab2 antibody comprising a heavy chain variable domain of SEQ ID NO: 8 and light chain variable domain of SEQ ID NO: 4 or Mab2 antibody comprising a heavy chain variable domain of SEQ ID NO: 33 and light chain variable domain of SEQ ID NO: 37) via a single SC injection. In parallel, additional animals are treated with the comparator molecule (i.e., Mab2 antibody comprising a heavy chain variable domain of SEQ ID NO: 8 and light chain variable domain of SEQ ID NO: 4 or Mab2 antibody comprising a heavy chain variable domain of SEQ ID NO: 33 and light chain variable domain of SEQ ID NO: 37) at a dose of 100 mg/Kg IV. Plasma samples are collected at baseline, 30 minutes, 1, 4, 8 hours and at days 2, 3, 4, 5, and 8. Blood samples are evaluated for levels of anti-C1q inhibitor/comparator molecule and for inhibition of C1q and serum hemolytic activity. The SC dose at which free drug levels are measurable in blood along with complete inhibition of free C1q for at least 24 hours is determined. IV dosing with 100 mg/Kg of the comparator anti-C1q monoclonal antibody results in complete inhibition of C1q for at least 5-8 days after a single dose.

Tissue Distribution of SC Dose of Anti-C1q Inhibitor: Next, animals are treated with single SC injection of the anti-C1q inhibitor at the selected dose, which leads to full saturation of C1q in the blood for 24 hours in first dose selection study. In parallel, additional animals are treated with the comparator molecule at a dose of 100 mg/Kg IV. Animals are euthanized at time points of 8 hrs, day 2, 3, and 4. At each time point blood is collected. Animals are then perfused with sterile saline to completely flush the blood out of the vascular compartment. Tissues including skin, subcutaneous fat, liver, lung and muscle are harvested. Blood samples are evaluated for levels of anti-C1q inhibitor/comparator molecule and for inhibition of C1q and serum hemolytic activity at each time point. Tissue samples (devoid of blood) are homogenized and evaluated for levels of anti-C1q inhibitor/comparator molecule and for inhibition of tissue C1q at each time point. Single SC administration of the anti-C1q inhibitor shows complete saturation and inhibition of C1q in the blood for 24 hours (until day 2) but not on days 3 and 4. In tissue samples, free drug levels are below limit of quantitation and no inhibition of free C1q is observed at any time point. These results show that following a single subcutaneous dose of the anti-C1q inhibitor, drug levels are measurable in blood but not in tissue samples. In addition, C1q is fully inhibited in the blood but not in tissue samples.

Tissue Distribution of Multiple Daily Fixed SC Dose of Anti-C1q Inhibitor: Animals are treated with single SC injection of the anti-C1q inhibitor at the selected dose, once daily for 7 days. Additional animals are treated with the anti-C1q comparator molecule at a single dose of 100 mg/Kg IV. Animals are euthanized at day 2, 3, 7 and day 9 (2 days after last dose). At each time point blood is collected. Animals are then perfused with sterile saline to completely flush the blood out of the vascular compartment. Tissues including skin, subcutaneous fat, liver, lung and muscle are harvested. Blood samples are evaluated for levels of anti-C1q inhibitor/comparator molecule and for inhibition of C1q and serum hemolytic activity at each time point. Tissue samples (devoid of blood) are homogenized and evaluated for levels of anti-C1q inhibitor/comparator molecule and for inhibition of tissue C1q at each time point. Single SC administration of the anti-C1q inhibitor molecule shows complete saturation and inhibition of C1q in the blood at all time points but not at day 9 sample (collected 2 days after final dose). In tissue samples, free drug levels are below limit of quantitation and no inhibition of free C1q is observed at all time points. These results show that after multiple daily SC administration of the anti-C1q inhibitor molecule, drug levels are measurable in blood but not in tissue samples. In addition, C1q is fully inhibited in the blood but not in tissue samples with once daily SC dosing of the anti-C1q inhibitor molecule at defined doses.

Example 9: Assessment of Mab1 and FabA Clearance

Below are figures from Mab1 15 mpk IV, FabA 10 mpk IV and FabA 3 mpk SC.

Figure 12A:
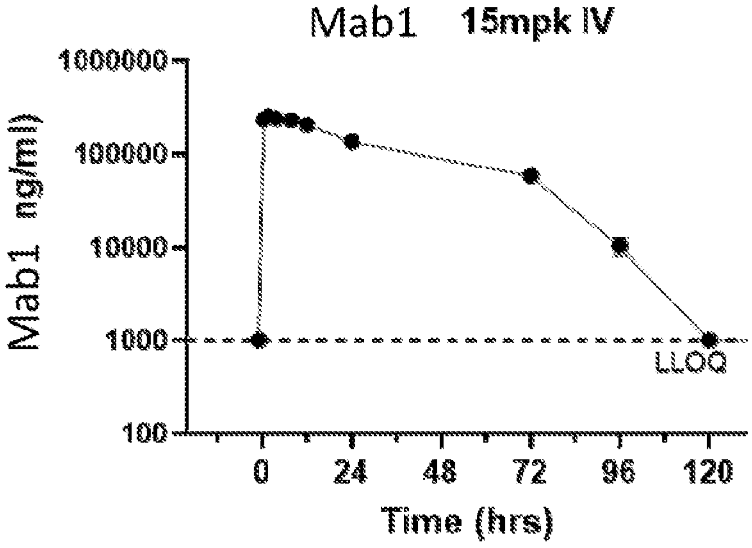
FIGS. 12A-12C show clearance data for Mab1 and FabA.
Figure 12B:
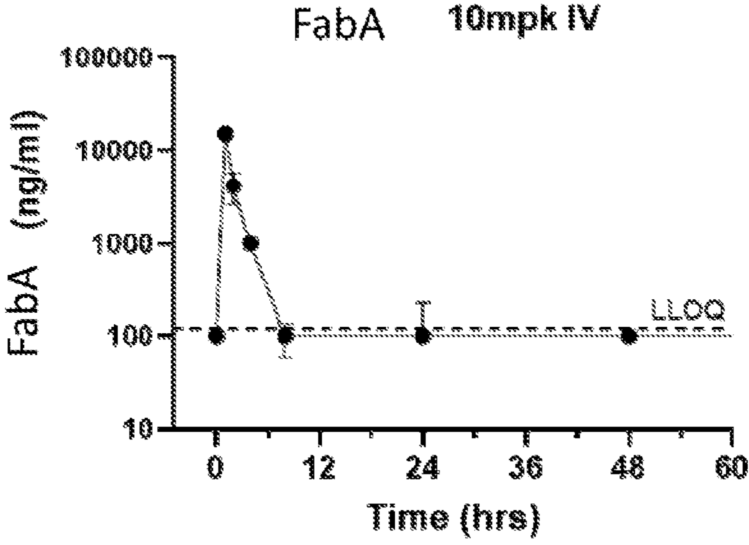
Figure 12C:
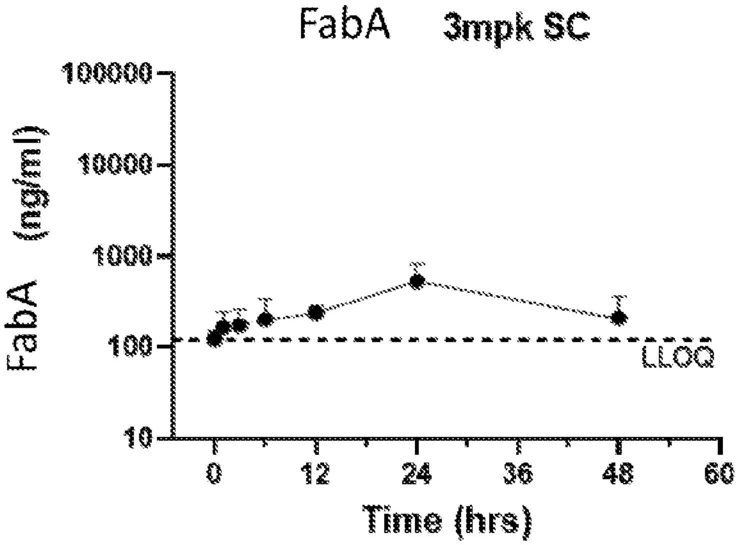

Cynomolgus monkeys were dosed with a single dose of Mab1 15 mpk IV, FabA 10 mpk IV and FabA 3 mpk SC. Blood samples were collected and processed for serum over time. Serum free-drug levels are measured and illustrated below. Mab1 15 mpk IV results in peak serum Free Mab1 levels of 250,000 ng/mL (FIG. 12A). Free drug levels stay elevated until day 4 and clears to levels below detection on day 5. FabA 10 mpk IV results in peak drug levels of 12000 ng/mL and clears very rapidly with drug levels falling below limit of detection by 8 hours (FIG. 12B). Estimated half-life of the Fab molecule is 2-3 hrs. FabA 3 mpk SC showed a very gradual increase in free drug levels and measurable at 24 hrs after a single dose (FIG. 12C).

These results demonstrate that the full IgG molecule Mab1 dosed IV displayed serum peak drug levels~250 ug/mL with slow clearance in the time frame of days. The FabA dosed IV shows peak serum drug levels of ~12 ug/mL that is completely cleared in 8 hrs. In contrast, The FabA dosed SC shows slow gradual increase in serum free drug levels with peak at 24 hrs and cleared by about 48 hrs.

Rapid clearance refers to the increased clearance of free serum Fab fragment levels compared to free serum full-length antibody levels (FIG. 12). Due to its long half-life, free serum full-length antibody levels stay elevated days after administration. In contrast, due to its short half-life, free serum Fab levels falls very rapidly within hours, i.e., it is rapidly cleared.

INCORPORATION BY REFERENCE

Each of the patents, published patent applications, and non-patent references cited herein are hereby incorporated by reference in their entirety.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a blood disorder associated with C1q-mediated activation of the classical complement pathway in a subject in need thereof, comprising administering to the subject a Cle inhibitor an anti-C1q antibody, wherein the anti-C1q antibody is a full-length antibody or antigen-binding fragment thereof comprising a light chain variable domain comprising an HVR-L1 having the amino acid sequence of SEQ ID NO: 5, an HVR-L2 having the amino acid sequence of SEQ ID NO: 6, and an HVR-L3 having the amino acid sequence of SEQ ID NO: 7; and a heavy chain variable domain comprising an HVR-H1 having the amino acid sequence of SEQ ID NO: 9, an HVR-H2 having the amino acid sequence of SEQ ID NO: 10, and an HVR-H3 having the amino acid sequence of SEQ ID NO: 11; and wherein:

(i) the full-length antibody is administered to the subject by intravenous injection or infusion once a week, once every other week, or once a month at a dose between 10 mg/kg and 150 mg/kg, or at a dose between 75 mg/kg and 100 mg/kg;

(ii) the full-length antibody is administered to the subject by subcutaneous or intramuscular injection at a dose between 1 mg/kg and 10 mg/kg, or at a dose between 3 mg/kg and 5 mg/kg; or (iii) the antigen-binding fragment is administered to the subject by intravenous injection or infusion, by intramuscular injection, or by subcutaneous injection at a dose between 0.1 mg/kg and 50 mg/kg, or at a dose between 0.3 mg/kg and 10 mg/kg.

2. The method of claim 1, wherein the anti-C1q antibody or antigen-binding fragment thereof is a monoclonal antibody, a polyclonal antibody, a recombinant antibody, a humanized antibody, a human antibody, a chimeric antibody, a monovalent antibody, a multispecific antibody, or antibody derivative thereof.

3. The method of claim 2, wherein the anti-C1q antibody is an antigen-binding fragment and the antigen-binding fragment is a Fab fragment, a Fab' fragment, a F(ab')2 fragment, a Fv fragment, a diabody, or a single-chain variable fragment.

4. The method of claim 1, wherein the anti-C1q antibody or antigen-binding fragment thereof comprises a light chain variable domain comprising an amino acid sequence with at least about 95% sequence identity to the amino acid sequence selected from any one of SEQ ID NO: 4 and 35-38.

5. The method of claim 4, wherein the light chain variable domain an amino acid sequence selected from any one of SEQ ID NO: 4 and 35-38.

6. The method of claim 1, wherein the anti-C1q antibody or antigen-binding fragment thereof comprises a heavy chain variable domain comprising an amino acid sequence with at least about 95% sequence identity to the amino acid sequence selected from any one of SEQ ID NO: 8 and 31-34.

7. The method of claim 6, wherein the heavy chain variable domain comprises an amino acid sequence selected from any one of SEQ ID NO: 8 and 31-34.

8. The method of claim 1, wherein the anti-C1q antibody is an antibody antigen-binding fragment comprising a heavy chain Fab fragment of SEQ ID NO: 39 and a light chain Fab fragment of SEQ ID NO: 40.

9. The method of claim 1, wherein the full-length antibody is administered by subcutaneous or intramuscular injection daily, once every other day, once a week, once every other week, or once a month.

10. The method of claim 1, wherein the antigen-binding fragment is administered daily, once every other day, once a week, once every other week, or once a month.

11. The method of claim 10, wherein the antigen-binding fragment is administered at an initial predose that is higher than the daily, once every other day, once a week, once every other week, or once a month dose.

12. The method of claim 11, wherein the initial predose is between 3 mg/kg and 50 mg/kg or between 3 mg/kg and 20 mg/kg.

13. The method of claim 1, wherein the blood disorder is cold agglutinin hemolytic anemia (cold agglutinin disease), cold antibody hemolytic anemia, ABO-incompatible acute hemolytic reactions, warm agglutinin hemolytic anemia, warm antibody hemolytic anemia, warm autoimmune hemolytic anemia (WAIHA), autoimmune hemolytic anemia (AIHA), autoimmune thrombocytopenia, paroxysmal cold hemoglobinuria (PCH), antiphospholipid syndrome (APS), Evan's syndrome, neonatal alloimmune thrombocytopenia, red blood cell alloimmunization, Felty's syndrome, antibody-mediated thrombocytopenia, heparin-induced thrombocytopenia (HIT), heparin-induced thrombocytopenia and thrombosis (HITT), thrombotic thrombocytopenia purpura (TTP), immune thrombocytopenia purpura (ITP), thrombocytopenia, thrombosis, vasculitis, lupus nephritis, systemic lupus erythematosus (SLE), glomerulonephritis, anti-phospholipid antibody syndrome (APS), an infection, or a drug-induced hematologic disorder.

14. The method of claim 1, wherein the antigen-binding fragment is rapidly cleared, thereby sparing C1q activity outside a subject's blood space.

15. The method of claim 1, wherein the anti-C1q antibody or antigen-binding fragment thereof selectively inhibits C1q within a subject's blood space, thereby sparing C1q activity outside the subject's blood space.

16. The method of claim 14, wherein the blood space is confined within a blood vessel.

17. The method of claim 16, wherein the blood vessel is an artery, an arteriole, a capillary, a venule, or a vein.

18. The method of claim 14, wherein the blood space comprises serum, platelets, endothelial cells, blood cells, or hematopoietic cells.

19. The method of claim 14, wherein inhibiting C1q within the subject's blood space reduces tissue damage in a highly vascularized tissue.

20. The method of claim 19, wherein the highly vascularized tissue is kidney, alveoli, capillary bed, or glomerulus.

21. The method of claim 1, wherein the blood disorder is autoimmune thrombocytopenia, cold agglutinin hemolytic anemia (cold agglutinin disease), paroxysmal cold hemoglobinuria (PCH), warm autoimmune hemolytic anemia (WAIHA), or heparin-induced thrombocytopenia (HIT).

* * * * *

```
                    SEQUENCE LISTING


<160> NUMBER OF SEQ ID NOS: 85

<210> SEQ ID NO 1
<211> LENGTH: 245
<212> TYPE: PRT
<213> ORGANISM: Homo sapiens

<400> SEQUENCE: 1

Met Glu Gly Pro Arg Gly Trp Leu Val Leu Cys Val Leu Ala Ile Ser
1               5                   10                  15

Leu Ala Ser Met Val Thr Glu Asp Leu Cys Arg Ala Pro Asp Gly Lys
            20                  25                  30

Lys Gly Glu Ala Gly Arg Pro Gly Arg Arg Gly Arg Pro Gly Leu Lys
        35                  40                  45

Gly Glu Gln Gly Glu Pro Gly Ala Pro Gly Ile Arg Thr Gly Ile Gln
    50                  55                  60

Gly Leu Lys Gly Asp Gln Gly Glu Pro Gly Pro Ser Gly Asn Pro Gly
65                  70                  75                  80

Lys Val Gly Tyr Pro Gly Pro Ser Gly Pro Leu Gly Ala Arg Gly Ile
                85                  90                  95

Pro Gly Ile Lys Gly Thr Lys Gly Ser Pro Gly Asn Ile Lys Asp Gln
            100                 105                 110
```

```
Pro Arg Pro Ala Phe Ser Ala Ile Arg Arg Asn Pro Pro Met Gly Gly
        115                 120                 125

Asn Val Val Ile Phe Asp Thr Val Ile Thr Asn Gln Glu Glu Pro Tyr
    130                 135                 140

Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175

Ser Ser Ser Arg Gly Gln Val Arg Arg Ser Leu Gly Phe Cys Asp Thr
            180                 185                 190

Thr Asn Lys Gly Leu Phe Gln Val Val Ser Gly Gly Met Val Leu Gln
        195                 200                 205

Leu Gln Gln Gly Asp Gln Val Trp Val Glu Lys Asp Pro Lys Lys Gly
    210                 215                 220

His Ile Tyr Gln Gly Ser Glu Ala Asp Ser Val Phe Ser Gly Phe Leu
225                 230                 235                 240

Ile Phe Pro Ser Ala
                245


<210> SEQ ID NO 2
<211> LENGTH: 253
<212> TYPE: PRT
<213> ORGANISM: Homo sapiens

<400> SEQUENCE: 2

Met Met Met Lys Ile Pro Trp Gly Ser Ile Pro Val Leu Met Leu Leu
1               5                   10                  15

Leu Leu Leu Gly Leu Ile Asp Ile Ser Gln Ala Gln Leu Ser Cys Thr
            20                  25                  30

Gly Pro Pro Ala Ile Pro Gly Ile Pro Gly Ile Pro Gly Thr Pro Gly
        35                  40                  45

Pro Asp Gly Gln Pro Gly Thr Pro Gly Ile Lys Gly Glu Lys Gly Leu
    50                  55                  60

Pro Gly Leu Ala Gly Asp His Gly Glu Phe Gly Glu Lys Gly Asp Pro
65                  70                  75                  80

Gly Ile Pro Gly Asn Pro Gly Lys Val Gly Pro Lys Gly Pro Met Gly
                85                  90                  95

Pro Lys Gly Gly Pro Gly Ala Pro Gly Ala Pro Gly Pro Lys Gly Glu
            100                 105                 110

Ser Gly Asp Tyr Lys Ala Thr Gln Lys Ile Ala Phe Ser Ala Thr Arg
        115                 120                 125

Thr Ile Asn Val Pro Leu Arg Arg Asp Gln Thr Ile Arg Phe Asp His
    130                 135                 140

Val Ile Thr Asn Met Asn Asn Asn Tyr Glu Pro Arg Ser Gly Lys Phe
145                 150                 155                 160

Thr Cys Lys Val Pro Gly Leu Tyr Tyr Phe Thr Tyr His Ala Ser Ser
                165                 170                 175

Arg Gly Asn Leu Cys Val Asn Leu Met Arg Gly Arg Glu Arg Ala Gln
            180                 185                 190

Lys Val Val Thr Phe Cys Asp Tyr Ala Tyr Asn Thr Phe Gln Val Thr
        195                 200                 205

Thr Gly Gly Met Val Leu Lys Leu Glu Gln Gly Glu Asn Val Phe Leu
    210                 215                 220

Gln Ala Thr Asp Lys Asn Ser Leu Leu Gly Met Glu Gly Ala Asn Ser
225                 230                 235                 240
```

```
Ile Phe Ser Gly Phe Leu Leu Phe Pro Asp Met Glu Ala
                245                 250


<210> SEQ ID NO 3
<211> LENGTH: 245
<212> TYPE: PRT
<213> ORGANISM: Homo sapiens

<400> SEQUENCE: 3

Met Asp Val Gly Pro Ser Ser Leu Pro His Leu Gly Leu Lys Leu Leu
1               5                   10                  15

Leu Leu Leu Leu Leu Leu Pro Leu Arg Gly Gln Ala Asn Thr Gly Cys
            20                  25                  30

Tyr Gly Ile Pro Gly Met Pro Gly Leu Pro Gly Ala Pro Gly Lys Asp
        35                  40                  45

Gly Tyr Asp Gly Leu Pro Gly Pro Lys Gly Glu Pro Gly Ile Pro Ala
    50                  55                  60

Ile Pro Gly Ile Arg Gly Pro Lys Gly Gln Lys Gly Glu Pro Gly Leu
65                  70                  75                  80

Pro Gly His Pro Gly Lys Asn Gly Pro Met Gly Pro Pro Gly Met Pro
                85                  90                  95

Gly Val Pro Gly Pro Met Gly Ile Pro Gly Glu Pro Gly Glu Glu Gly
            100                 105                 110

Arg Tyr Lys Gln Lys Phe Gln Ser Val Phe Thr Val Thr Arg Gln Thr
        115                 120                 125

His Gln Pro Pro Ala Pro Asn Ser Leu Ile Arg Phe Asn Ala Val Leu
    130                 135                 140

Thr Asn Pro Gln Gly Asp Tyr Asp Thr Ser Thr Gly Lys Phe Thr Cys
145                 150                 155                 160

Lys Val Pro Gly Leu Tyr Tyr Phe Val Tyr His Ala Ser His Thr Ala
                165                 170                 175

Asn Leu Cys Val Leu Leu Tyr Arg Ser Gly Val Lys Val Val Thr Phe
            180                 185                 190

Cys Gly His Thr Ser Lys Thr Asn Gln Val Asn Ser Gly Gly Val Leu
        195                 200                 205

Leu Arg Leu Gln Val Gly Glu Glu Val Trp Leu Ala Val Asn Asp Tyr
    210                 215                 220

Tyr Asp Met Val Gly Ile Gln Gly Ser Asp Ser Val Phe Ser Gly Phe
225                 230                 235                 240

Leu Leu Phe Pro Asp
                245


<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Asn Lys Tyr
            20                  25                  30

Leu Ala Trp Tyr Gln Glu Lys Pro Gly Lys Thr Asn Lys Leu Leu Ile
        35                  40                  45
```

```
Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Ala Gly Thr Lys Leu Glu Leu Lys
            100                 105


<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ala Ser Lys Ser Ile Asn Lys Tyr Leu Ala
1               5                   10


<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Gly Ser Thr Leu Gln Ser
1               5


<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Gln His Asn Glu Tyr Pro Leu Thr
1               5


<210> SEQ ID NO 8
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Gln Gln Pro Gly Ala Glu Leu Val Lys Pro Gly Ala
1               5                   10                  15

Ser Val Lys Leu Ser Cys Lys Ser Ser Gly Tyr His Phe Thr Ser Tyr
            20                  25                  30

Trp Met His Trp Val Lys Gln Arg Pro Gly Gln Gly Leu Glu Trp Ile
        35                  40                  45

Gly Val Ile His Pro Asn Ser Gly Ser Ile Asn Tyr Asn Glu Lys Phe
    50                  55                  60

Glu Ser Lys Ala Thr Leu Thr Val Asp Lys Ser Ser Ser Thr Ala Tyr
```

```
65                  70                  75                  80

Met Gln Leu Ser Ser Leu Thr Ser Glu Asp Ser Ala Val Tyr Tyr Cys
                85                  90                  95

Ala Gly Glu Arg Asp Ser Thr Glu Val Leu Pro Met Asp Tyr Trp Gly
            100                 105                 110

Gln Gly Thr Ser Val Thr Val Ser Ser
        115                 120


<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Tyr His Phe Thr Ser Tyr Trp Met His
1               5                   10


<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Ile His Pro Asn Ser Gly Ser Ile Asn Tyr Asn Glu Lys Phe Glu
1               5                   10                  15

Ser


<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Arg Asp Ser Thr Glu Val Leu Pro Met Asp Tyr
1               5                   10


<210> SEQ ID NO 12
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

gatgtccaga taacccagtc tccatcttat cttgctgcat ctcctggaga aaccattact      60

attaattgca gggcaagtaa gagcattaac aaatatttag cctggtatca agagaaacct     120

gggaaaacta ataagcttct tatctactct ggatccactt tgcaatctgg aattccatca     180

aggttcagtg gcagtggatc tggtacagat ttcactctca ccatcagtag cctggagcct     240

gaagattttg caatgtatta ctgtcaacaa cataatgaat acccgctcac gttcggtgct     300

gggaccaagc tggagctgaa a                                               321
```

<210> SEQ ID NO 13
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
caggtccaac tgcagcagcc tggggctgag ctggtaaagc ctggggcttc agtgaagttg 60
tcctgcaagt cttctggcta ccatttcacc agctactgga tgcactgggt gaagcagagg 120
cctggacaag gccttgagtg gattggagtg attcatccta atagtggtag tattaactac 180
aatgagaagt tcgagagcaa ggccacactg actgtagaca aatcctccag cacagcctac 240
atgcaactca gcagcctgac atctgaggac tcggcggtct attattgtgc aggagagaga 300
gattctacgg aggttctccc tatggactac tggggtcaag gaacctcagt caccgtctcc 360
tca 363

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

```
Gln Val Gln Leu Val Gln Ser Gly Ala Glu Leu Lys Lys Pro Gly Ala
1               5                   10                  15

Ser Val Lys Val Ser Cys Lys Ser Ser Gly Tyr His Phe Thr Ser Tyr
```

```
            20                  25                  30

Trp Met His Trp Val Lys Gln Ala Pro Gly Gln Gly Leu Glu Trp Ile
        35                  40                  45

Gly Val Ile His Pro Asn Ser Gly Ser Ile Asn Tyr Asn Glu Lys Phe
    50                  55                  60

Glu Ser Lys Ala Thr Ile Thr Val Asp Lys Ser Thr Ser Thr Ala Tyr
65                  70                  75                  80

Met Gln Leu Ser Ser Leu Thr Ser Glu Asp Ser Ala Val Tyr Tyr Cys
                85                  90                  95

Ala Gly Glu Arg Asp Ser Thr Glu Val Leu Pro Met Asp Tyr Trp Gly
            100                 105                 110

Gln Gly Thr Ser Val Thr Val Ser Ser
        115                 120


<210> SEQ ID NO 32
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Val Gln Ser Gly Ala Glu Leu Lys Lys Pro Gly Ala
1               5                   10                  15

Ser Val Lys Val Ser Cys Lys Ser Ser Gly Tyr His Phe Thr Ser Tyr
            20                  25                  30

Trp Met His Trp Val Lys Gln Ala Pro Gly Gln Gly Leu Glu Trp Ile
        35                  40                  45

Gly Val Ile His Pro Asn Ser Gly Ser Ile Asn Tyr Asn Glu Lys Phe
    50                  55                  60

Glu Ser Arg Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Arg Asp Ser Thr Glu Val Leu Pro Met Asp Tyr Trp Gly
            100                 105                 110

Gln Gly Thr Thr Val Thr Val Ser Ser
        115                 120


<210> SEQ ID NO 33
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Val Gln Ser Gly Ala Glu Leu Lys Lys Pro Gly Ala
1               5                   10                  15

Ser Val Lys Val Ser Cys Lys Ser Ser Gly Tyr His Phe Thr Ser Tyr
            20                  25                  30

Trp Met His Trp Val Lys Gln Ala Pro Gly Gln Gly Leu Glu Trp Ile
        35                  40                  45

Gly Val Ile His Pro Asn Ser Gly Ser Ile Asn Tyr Asn Glu Lys Phe
    50                  55                  60

Glu Ser Arg Val Thr Ile Thr Val Asp Lys Ser Thr Ser Thr Ala Tyr
```

```
65                  70                  75                  80

Met Glu Leu Ser Ser Leu Arg Ser Glu Asp Thr Ala Val Tyr Tyr Cys
                85                  90                  95

Ala Gly Glu Arg Asp Ser Thr Glu Val Leu Pro Met Asp Tyr Trp Gly
            100                 105                 110

Gln Gly Thr Thr Val Thr Val Ser Ser
        115                 120


<210> SEQ ID NO 34
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Val Gln Ser Gly Ala Glu Leu Lys Lys Pro Gly Ala
1               5                   10                  15

Ser Val Lys Val Ser Cys Lys Ser Ser Gly Tyr His Phe Thr Ser Tyr
            20                  25                  30

Trp Met His Trp Val Arg Gln Ala Pro Gly Gln Gly Leu Glu Trp Ile
        35                  40                  45

Gly Val Ile His Pro Asn Ser Gly Ser Ile Asn Tyr Asn Glu Lys Phe
    50                  55                  60

Glu Ser Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Arg Asp Ser Thr Glu Val Leu Pro Met Asp Tyr Trp Gly
            100                 105                 110

Gln Gly Thr Thr Val Thr Val Ser Ser
        115                 120


<210> SEQ ID NO 35
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Val Gln Ile Thr Gln Ser Pro Ser Tyr Leu Ala Ala Ser Leu Gly
1               5                   10                  15

Glu Arg Ala Thr Ile Asn Cys Arg Ala Ser Lys Ser Ile Asn Lys Tyr
            20                  25                  30

Leu Ala Trp Tyr Gln Gln Lys Pro Gly Lys Thr Asn Lys Leu Leu Ile
        35                  40                  45

Tyr Ser Gly Ser Thr Leu Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Gln Gly Thr Lys Leu Glu Ile Lys
            100                 105
```

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

```
Asp Val Gln Ile Thr Gln Ser Pro Ser Ser Leu Ser Ala Ser Leu Gly
1               5                   10                  15

Glu Arg Ala Thr Ile Asn Cys Arg Ala Ser Lys Ser Ile Asn Lys Tyr
            20                  25                  30

Leu Ala Trp Tyr Gln Gln Lys Pro Gly Lys Ala Asn Lys Leu Leu Ile
        35                  40                  45

Tyr Ser Gly Ser Thr Leu Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Gln Gly Thr Lys Leu Glu Ile Lys
            100                 105
```

<210> SEQ ID NO 37
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

```
Asp Val Gln Ile Thr Gln Ser Pro Ser Ser Leu Ser Ala Ser Leu Gly
1               5                   10                  15

Glu Arg Ala Thr Ile Asn Cys Arg Ala Ser Lys Ser Ile Asn Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Gln Gly Thr Lys Leu Glu Ile Lys
            100                 105
```

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

```
Asp Ile Gln Leu Thr Gln Ser Pro Ser Ser Leu Ser Ala Ser Leu Gly
1               5                   10                  15

Glu Arg Ala Thr Ile Asn Cys Arg Ala Ser Lys Ser Ile Asn Lys Tyr
            20                  25                  30
```

```
Leu Ala Trp Tyr Gln Gln Lys Pro Gly Lys Ala Pro Lys Leu Leu Ile
        35                  40                  45

Tyr Ser Gly Ser Thr Leu Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Gln Gly Thr Lys Leu Glu Ile Lys
            100                 105


<210> SEQ ID NO 39
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Gln Ser Gly Ala Glu Leu Lys Lys Pro Gly Ala
1               5                   10                  15

Ser Val Lys Val Ser Cys Lys Ser Ser Gly Tyr His Phe Thr Ser Tyr
            20                  25                  30

Trp Met His Trp Val Lys Gln Ala Pro Gly Gln Gly Leu Glu Trp Ile
        35                  40                  45

Gly Val Ile His Pro Asn Ser Gly Ser Ile Asn Tyr Asn Glu Lys Phe
    50                  55                  60

Glu Ser Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Glu Arg Asp Ser Thr Glu Val Leu Pro Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr
225


<210> SEQ ID NO 40
<211> LENGTH: 214
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 40

```
Asp Val Gln Ile Thr Gln Ser Pro Ser Ser Leu Ser Ala Ser Leu Gly
1               5                   10                  15

Glu Arg Ala Thr Ile Asn Cys Arg Ala Ser Lys Ser Ile Asn Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47
<211> LENGTH: 327
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320
```

Leu Ser Leu Ser Leu Gly Lys
325

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Ser Ser Val Ser Ser Ser Tyr Leu His Trp Tyr Gln
1 5 10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Ser Thr Ser Asn Leu Ala Ser Gly Val Pro
1 5 10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

His Gln Tyr Tyr Arg Leu Pro Pro Ile Thr
1 5 10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Gly Phe Thr Phe Ser Asn Tyr Ala Met Ser Trp Val

```
1               5                   10


<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ile Ser Ser Gly Gly Ser His Thr Tyr Tyr
1               5                   10


<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Arg Leu Phe Thr Gly Tyr Ala Met Asp Tyr
1               5                   10


<210> SEQ ID NO 57
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Val Met Thr Gln Thr Thr Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Phe Tyr Ser Leu Thr Ile Ser Ser Met Glu
65                  70                  75                  80

Ala Glu Asp Asp Ala Thr Tyr Tyr Cys His Gln Tyr Tyr Arg Leu Pro
                85                  90                  95

Pro Ile Thr Phe Gly Ala Gly Thr Lys Leu Glu Leu Lys
            100                 105


<210> SEQ ID NO 58
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Lys Leu Glu Glu Ser Gly Gly Ala Leu Val Lys Pro Gly Gly
1               5                   10                  15

Ser Leu Lys Leu Ser Cys Ala Ala Ser Gly Phe Thr Phe Ser Asn Tyr
            20                  25                  30
```

```
Ala Met Ser Trp Val Arg Gln Ile Pro Glu Lys Arg Leu Glu Trp Val
        35                  40                  45

Ala Thr Ile Ser Ser Gly Gly Ser His Thr Tyr Tyr Leu Asp Ser Val
    50                  55                  60

Lys Gly Arg Phe Thr Ile Ser Arg Asp Asn Ala Arg Asp Thr Leu Tyr
65                  70                  75                  80

Leu Gln Met Ser Ser Leu Arg Ser Glu Asp Thr Ala Leu Tyr Tyr Cys
                85                  90                  95

Ala Arg Leu Phe Thr Gly Tyr Ala Met Asp Tyr Trp Gly Gln Gly Thr
            100                 105                 110

Ser Val Thr
        115
```

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

```
Thr Ala Ser Ser Ser Val Ser Ser Ser Tyr Leu His
1               5                   10
```

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

```
Ser Thr Ser Asn Leu Ala Ser
1               5
```

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

```
Asn Tyr Ala Met Ser
```

1 5

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Thr Ile Ser Ser Gly Gly Ser His Thr Tyr Tyr Leu Asp Ser Val Lys
1 5 10 15

Gly

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

Leu Phe Thr Gly Tyr Ala Met Asp Tyr
1 5

<210> SEQ ID NO 67
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

Gln Ile Val Leu Thr Gln Ser Pro Ala Ile Met Ser Ala Ser Leu Gly
1 5 10 15

Glu Arg Val Thr Met Thr Cys Thr Ala Ser Ser Ser Val Ser Ser Ser
20 25 30

Tyr Leu His Trp Tyr Gln Gln Lys Pro Gly Ser Ser Pro Lys Leu Trp
35 40 45

Ile Tyr Ser Thr Ser Asn Leu Ala Ser Gly Val Pro Ala Arg Phe Ser
50 55 60

Gly Ser Gly Ser Gly Thr Phe Tyr Ser Leu Thr Ile Ser Ser Met Glu
65 70 75 80

Ala Glu Asp Asp Ala Thr Tyr Tyr Cys His Gln Tyr Tyr Arg Leu Pro
85 90 95

Pro Ile Thr Phe Gly Ala Gly Thr Lys Leu Glu Leu Lys
100 105

<210> SEQ ID NO 68
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

Glu Val Met Leu Val Glu Ser Gly Gly Ala Leu Val Lys Pro Gly Gly
1 5 10 15

Ser Leu Lys Leu Ser Cys Ala Ala Ser Gly Phe Thr Phe Ser Asn Tyr

```
            20                  25                  30

Ala Met Ser Trp Val Arg Gln Ile Pro Glu Lys Arg Leu Glu Trp Val
        35                  40                  45

Ala Thr Ile Ser Ser Gly Gly Ser His Thr Tyr Tyr Leu Asp Ser Val
    50                  55                  60

Lys Gly Arg Phe Thr Ile Ser Arg Asp Asn Ala Arg Asp Thr Leu Tyr
65                  70                  75                  80

Leu Gln Met Ser Ser Leu Arg Ser Glu Asp Thr Ala Leu Tyr Tyr Cys
                85                  90                  95

Ala Arg Leu Phe Thr Gly Tyr Ala Met Asp Tyr Trp Gly Gln Gly Thr
            100                 105                 110

Ser Val Thr Val Ser Ser
        115
```

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

-continued

```
<400> SEQUENCE: 77

000


<210> SEQ ID NO 78

<400> SEQUENCE: 78

000


<210> SEQ ID NO 79

<400> SEQUENCE: 79

000


<210> SEQ ID NO 80

<400> SEQUENCE: 80

000


<210> SEQ ID NO 81

<400> SEQUENCE: 81

000


<210> SEQ ID NO 82

<400> SEQUENCE: 82

000


<210> SEQ ID NO 83

<400> SEQUENCE: 83

000


<210> SEQ ID NO 84

<400> SEQUENCE: 84

000


<210> SEQ ID NO 85

<400> SEQUENCE: 85

000
```